(12) United States Patent  
Caira et al.

(10) Patent No.: US 8,721,520 B2  
(45) Date of Patent: May 13, 2014

(54) INFLATABLE IMPLANT DELIVERY SYSTEM AND METHOD

(71) Applicant: Attenuex Technologies, Inc., Newton, MA (US)

(72) Inventors: Sheila Caira, Auburndale, MA (US); John Gillespie, Jr., Dover, MA (US); Peter Dayton, Charlestown, MA (US); Kevin G. Connors, Wellesley, MA (US)

(73) Assignee: AttenueX Technologies, Inc., Newton, MA (US)

( * ) Notice: Subject to any disclaimer, the term of this patent is extended or adjusted under 35 U.S.C. 154(b) by 0 days.

(21) Appl. No.: 13/925,659

(22) Filed: Jun. 24, 2013

(65) Prior Publication Data

US 2013/0289529 A1     Oct. 31, 2013

Related U.S. Application Data

(63) Continuation of application No. 12/625,508, filed on Nov. 24, 2009, now Pat. No. 8,574,146.

(60) Provisional application No. 61/200,147, filed on Nov. 25, 2008, provisional application No. 61/211,515, filed on Mar. 31, 2009.

(51) Int. Cl.  
*A61F 2/00* (2006.01)

(52) U.S. Cl.  
USPC ............................................................. 600/30

(58) Field of Classification Search  
USPC ......... 600/29–32, 37; 128/897, 898, DIG. 25; 606/1  
See application file for complete search history.

(56) References Cited

U.S. PATENT DOCUMENTS

| | | | |
|---|---|---|---|
| 2,849,001 | A | 8/1958 | Oddo |
| 3,841,304 | A | 10/1974 | Jones |
| 3,964,484 | A | 6/1976 | Reynolds et al. |
| 4,044,401 | A | 8/1977 | Guiset |
| 4,246,893 | A | 1/1981 | Berson |
| 4,311,146 | A | 1/1982 | Wonder |

(Continued)

FOREIGN PATENT DOCUMENTS

| | | |
|---|---|---|
| EP | 1813303 | 8/2007 |
| FR | 2774579 | 8/1999 |

(Continued)

OTHER PUBLICATIONS

A New Technique for Dynamic Analysis of Bladder Compliance, Robert F. Gilmore et al., The Journal of Urology, vol. 150, pp. 1200-1203, Oct. 1993.

(Continued)

*Primary Examiner* — Samuel Gilbert  
(74) *Attorney, Agent, or Firm* — Knobbe Martens Olson & Bear LLP

(57) ABSTRACT

An implant delivery system can be configured to deliver an inflatable implant into a bladder via a urethra. The delivery system can comprise an elongate tubular body, an inflation tube and an implant decoupler. The tubular body can comprise a central lumen configured to hold an inflatable implant in an initial un-inflated state for delivery of the implant into the bladder. A method of use can include passing a distal tip of the elongate tubular body into the bladder. The implant can be inflated and released into the bladder.

27 Claims, 64 Drawing Sheets

(56) References Cited

U.S. PATENT DOCUMENTS

| | | |
|---|---|---|
| 4,341,218 A | 7/1982 | Ü |
| 4,346,712 A | 8/1982 | Handa et al. |
| 4,364,392 A | 12/1982 | Strother et al. |
| 4,416,267 A | 11/1983 | Garren et al. |
| 4,416,663 A | 11/1983 | Hall |
| 4,441,495 A | 4/1984 | Hicswa |
| 4,517,979 A | 5/1985 | Pecenka |
| 4,545,367 A | 10/1985 | Tucci |
| 4,607,618 A | 8/1986 | Angelchik |
| 4,694,827 A | 9/1987 | Weiner et al. |
| 4,723,547 A | 2/1988 | Kullas et al. |
| 4,773,393 A | 9/1988 | Haber et al. |
| 4,802,479 A | 2/1989 | Haber et al. |
| 4,819,637 A | 4/1989 | Dormandy, Jr. et al. |
| 4,832,680 A * | 5/1989 | Haber et al. ............ 600/31 |
| 4,850,963 A | 7/1989 | Sparks et al. |
| 4,899,747 A | 2/1990 | Garren et al. |
| 4,925,446 A | 5/1990 | Garay et al. |
| 4,929,214 A | 5/1990 | Liebermann |
| 4,930,535 A | 6/1990 | Rinehold |
| 4,938,766 A | 7/1990 | Jarvik |
| 5,019,032 A * | 5/1991 | Robertson ............ 600/29 |
| 5,084,061 A | 1/1992 | Gau et al. |
| 5,144,708 A | 9/1992 | Pekar |
| 5,181,921 A | 1/1993 | Makita et al. |
| 5,222,970 A | 6/1993 | Reeves |
| 5,248,275 A | 9/1993 | McGrath et al. |
| 5,295,960 A * | 3/1994 | Aliahmad et al. ....... 604/103.11 |
| 5,304,123 A | 4/1994 | Atala et al. |
| 5,308,327 A | 5/1994 | Heaven et al. |
| 5,356,430 A | 10/1994 | Nadol, Jr. |
| 5,389,217 A | 2/1995 | Singer |
| 5,403,123 A | 4/1995 | Walters |
| 5,411,475 A | 5/1995 | Atala et al. |
| 5,433,216 A | 7/1995 | Sugrue et al. |
| 5,437,603 A | 8/1995 | Cerny et al. |
| 5,479,945 A | 1/1996 | Simon |
| 5,501,669 A | 3/1996 | Conway et al. |
| 5,513,659 A | 5/1996 | Buuck et al. |
| 5,564,143 A | 10/1996 | Pekar et al. |
| 5,588,438 A | 12/1996 | McKnown et al. |
| 5,588,556 A | 12/1996 | Sancoff et al. |
| 5,603,685 A | 2/1997 | Tutrone, Jr. |
| 5,617,876 A | 4/1997 | Van Duyl |
| 5,667,520 A | 9/1997 | Bonutti |
| 5,695,741 A | 12/1997 | Schutt et al. |
| 5,720,938 A | 2/1998 | Schutt et al. |
| 5,755,239 A | 5/1998 | Baltierra |
| 5,779,672 A | 7/1998 | Dormandy, Jr. |
| 5,782,812 A | 7/1998 | Hart et al. |
| 5,830,228 A | 11/1998 | Knapp et al. |
| 5,830,780 A | 11/1998 | Dennison et al. |
| 5,868,141 A | 2/1999 | Ellias |
| 5,916,198 A | 6/1999 | Dillow |
| 5,964,806 A | 10/1999 | Cook et al. |
| 5,989,180 A | 11/1999 | Norton |
| 5,992,419 A | 11/1999 | Sterzer et al. |
| 5,992,700 A | 11/1999 | McGlothlin et al. |
| 6,021,781 A | 2/2000 | Thompson et al. |
| 6,027,442 A | 2/2000 | Von Iderstein |
| 6,045,498 A | 4/2000 | Burton et al. |
| 6,095,969 A | 8/2000 | Karram et al. |
| 6,102,848 A | 8/2000 | Porter |
| 6,119,697 A | 9/2000 | Engel et al. |
| 6,127,010 A | 10/2000 | Rudy |
| 6,171,298 B1 | 1/2001 | Matsuura et al. |
| 6,240,968 B1 | 6/2001 | Bigonzi-Jaker et al. |
| 6,251,138 B1 | 6/2001 | Nadol et al. |
| 6,293,923 B1 | 9/2001 | Yachia et al. |
| 6,311,689 B1 | 11/2001 | Tihon |
| 6,372,195 B1 | 4/2002 | Schutt et al. |
| 6,398,718 B1 * | 6/2002 | Yachia et al. ............ 600/29 |
| 6,398,738 B1 | 6/2002 | Millar |
| 6,463,332 B1 | 10/2002 | Aldrich |
| 6,544,287 B1 | 4/2003 | Johnson et al. |
| 6,682,473 B1 | 1/2004 | Matsuura et al. |
| 6,736,793 B2 | 5/2004 | Meyer et al. |
| 6,746,421 B2 | 6/2004 | Yachia et al. |
| 6,849,061 B2 | 2/2005 | Wagner |
| 6,976,950 B2 | 12/2005 | Connors et al. |
| 6,976,951 B2 | 12/2005 | Connors et al. |
| 6,988,983 B2 | 1/2006 | Connors et al. |
| 7,074,178 B2 | 7/2006 | Connors et al. |
| 7,083,626 B2 | 8/2006 | Hart et al. |
| 7,112,185 B2 | 9/2006 | Hart et al. |
| 7,150,853 B2 | 12/2006 | Lee et al. |
| 7,374,532 B2 | 5/2008 | Connors et al. |
| 7,390,317 B2 | 6/2008 | Taylor et al. |
| 7,470,228 B2 | 12/2008 | Connors et al. |
| 7,484,510 B2 | 2/2009 | Connors et al. |
| 7,540,876 B2 | 6/2009 | Connors et al. |
| 7,691,051 B2 | 4/2010 | Connors et al. |
| 7,766,814 B2 | 8/2010 | Walsh |
| 7,771,395 B2 | 8/2010 | Hart et al. |
| 7,811,221 B2 | 10/2010 | Gross |
| 8,016,740 B2 | 9/2011 | Connors et al. |
| 8,025,064 B2 | 9/2011 | Connors et al. |
| 2002/0026226 A1 | 2/2002 | Ein |
| 2002/0055730 A1 | 5/2002 | Yachia et al. |
| 2002/0082551 A1 | 6/2002 | Yachia et al. |
| 2002/0165427 A1 | 11/2002 | Yachia et al. |
| 2004/0111006 A1 | 6/2004 | Alferness et al. |
| 2004/0143319 A1 | 7/2004 | Schwartz et al. |
| 2004/0260272 A1 | 12/2004 | Friedman et al. |
| 2005/0070995 A1 | 3/2005 | Zilla et al. |
| 2006/0264697 A1 | 11/2006 | Timm et al. |
| 2007/0202151 A1 | 8/2007 | Lee et al. |
| 2008/0086082 A1 | 4/2008 | Brooks |
| 2008/0086149 A1 | 4/2008 | Diamant et al. |
| 2008/0275428 A1 | 11/2008 | Tegg et al. |
| 2009/0105527 A1 | 4/2009 | Connors et al. |
| 2009/0240277 A1 | 9/2009 | Connors et al. |
| 2010/0222802 A1 | 9/2010 | Gillespie, Jr. et al. |

FOREIGN PATENT DOCUMENTS

| | | |
|---|---|---|
| GB | 2023405 | 1/1980 |
| JP | 1285263 | 11/1989 |
| JP | 5049690 | 3/1993 |
| JP | 2000-325328 | 11/2000 |
| JP | 2007-190430 | 8/2007 |
| WO | WO 90/13321 | 11/1990 |
| WO | WO 91/03267 | 3/1991 |
| WO | WO 99/24106 | 5/1999 |
| WO | WO 00/27405 | 5/2000 |
| WO | WO 00/54701 | 9/2000 |
| WO | WO 00/54702 | 9/2000 |
| WO | WO 01/02042 | 1/2001 |
| WO | WO 01/57093 | 8/2001 |
| WO | WO 01/64145 | 9/2001 |
| WO | WO 01/66052 | 9/2001 |
| WO | WO 01/78576 | 10/2001 |
| WO | WO 02/38038 | 5/2002 |
| WO | WO 02/065894 | 8/2002 |
| WO | WO 02/100300 | 12/2002 |
| WO | WO 03/015673 | 2/2003 |
| WO | WO 2004/091592 | 10/2004 |
| WO | WO 2004/096071 | 11/2004 |
| WO | WO 2005/058203 | 6/2005 |
| WO | WO 2006/086627 | 8/2006 |
| WO | WO 2007/050546 | 5/2007 |
| WO | WO 2007/059160 | 5/2007 |
| WO | WO 2007/103809 | 9/2007 |

OTHER PUBLICATIONS

The Effect of Urinary Bladder Shape on its Mechanics During Filling, Margot S. Damasar et al., Pergamon, vol. 6, pp. 725-732, 1995.

Difference in Bladder Compliance with Time and Associations of Bladder Management with Compliance in Spinal Cord Injured Patients, Kyle J. Weld et al., The Journal of Urology, vol. 163, pp. 1228-1233, Apr. 2000.

(56) References Cited

OTHER PUBLICATIONS

Visco-elastic Properties of Isolated Detrusor Smooth Muscle, A. Wagg et al., Scandinavian Journal of Urology Nephoral, Suppl. 201, pp. 12-18, 1999.
Decreased Elastin Gene Expression in Noncompliant Human Bladder Tissue: A Competitive Reverse Transcriptase-Polymerase Chain Reaction Analysis, Bob Djavan et al., Journal of Urology, vol. 160, pp. 1658-1662, Nov. 1998.
Molecular, Cellular and Experimental Morphology, Narinder Dass et al., Journal of Anatomy, vol. 195, Part 3, pp. 447-453, Oct. 1999.
Design of Miniaturized Ultrasonic Bladder Volume Monitor and Subsequent Preliminary Evaluation on 41 Enuretic Patients, IEEE Transactions on Rehabilitation Engineering, vol. 6, No. 1, pp. 66-74, Mar. 1998.
Temporal Expression of Elastic Fiber Components in Bladder Development, H.P. Koo et al., Connective Tissue Research, vol. 3701-20, pp. 1-11, 1998.
Voiding Dysfunction in Ileal Neobladder, Naohito Mikuma et al., The Journal of Urology, vol. 158 pp. 1365-1367, Oct. 1997.
Interstital Cystitus: Bladder Training with Intravesical Oxybutynin, George A. Barballas et al., The Journal of Urology, vol. 163, pp. 1818-1822, Jun. 2000.
Noninvasive Evaluation of Bladder Compliance in Children Using Ultrasound Estimated Bladder Weight, Osamu Ukimura et al., The Journal of Urology, vol. 160 pp. 1459-1462, Oct. 1998.
Surgical Complications of Bladder Augmentation: Comparison Between Various Enterocystoplasties in 133 Patients, Bijan Shekarriz et al., Elsevier Science Inc., Pediatric Urology 55, pp. 123-128, 2000.
Elastic Fibers and Their Role in Bladder Extracellular Matrix, Joel Rosenbloom et al., Muscle, Matrix and Bladder Function, vol. 385, pp. 161-184, 1995.
Effect of Spinal Versus General Anesthesia on Bladder Compliance and Intraabdominal Pressure During Transurethral Procedures, David Olsfanger et al., Journal of Clinical Anesthesia, vol. 11, pp. 328-331, 1999.
Structure of the Lymphatic Microcirculation in the Human Urinary Bladder with Different Intraluminal Pressure and Distension, R. Scelsi et al., Lymphologyu, pp. 60-66, 1996.
Boston Scientific Target Detachable Silicone Balloon, Product Information (Part No. ES-05827 Rev. A); published by Boston Scientific and Target Therapeutics at Fremont, CA or Natick,MA; relevant pages consist of the entire document (total of 24 pages); print-out in 2 pages from the USPTO's Trademark Electronic Search System identifying the date of first used in commerce of on or about Aug. 1998.
Urge Incontinence and the Unstable Bladder, Practical Urogynecology, Chapter 8—Incontinence and the Unstable Bladder, pp. 191-214, Oct. 1, 1993.
Abstract, Surgical treatment for stress urinary incontinence associated with valsalva induced detrusor instability., S.R. Serets et al. Website PubMed, Mar. 2000.
Abstract, Identifying patients who require urodynamic testing before surgery for stress incontinence based on questionnaire information and surgical history., G.E. Lemack et al., Website PubMed, Apr. 2000.
Abstract, Ambulatory urodynamics: do they help clinical management?, E. Gorton et al., Website PubMed, Mar. 2000.
Abstract, The effect of bladder filling on changes in ultrasonography parameters of the lower urinary tract in women with urinary stress incontinence., A. Martan et al., Website PubMed, Jan. 2000.
Abstract, Urodynamic protocol and central review of data for clinical trials in lower urinary tract dysfunction., P. Lewis et al., Website PubMed, Mar. 2000.
Abstract, New data on the diagnosis and treatment of urinary stress incontinence in women., J. Colin et al., Website PubMed, Feb. 2000.
Abstract, Office evaluation of the patient with an overactive urinary bladder., .J. Kowalcyzk, Website PubMed, Mar. 2000.
Abstract, Surgical and medical treatment options for urge incontinence., J.M. Lonsway, Website PubMed, Mar. 2000.
Abstract, Experimental development of a fixed volume, gravity draining, prosthetic urinary bladder., M.J. Gleeson et al., Website PubMed, Jul. 1990.
Abstract, Urodynamics of normal and disordered miction., U. Jonas, Website PubMed, Oct. 1979.
Abstract, Whole bladder mechanics during filling., M.S. Damaser, Website PubMed, Oct. 1999.
Abstract, A mathematical micturition to restore simple flow recordings in healthy and symptomatic individuals and enhance uroflow interpretation., F.A. Valentini et al., Website PubMed, 2000.
Abstract, Barometers and bladders: a primer on pressures., D.A. Bloom et al., Website PubMed, Mar. 2000.
Die Detrusormyektomie (Autoaugmentation) in der Behandlung der Hyperreflexiven Low-compliance-Blasé, M. Stohrer et al., Der Urologe [A], pp. 30-37, 1999.
Effect of aging on bladder function and the response to outlet obstruction in female rats, A.D. Kohan et al., Urol Res. 2000, 28: pp. 33-37.
European Search Report for European Patent Application No. EP 01 92 7115 dated Nov. 2, 2004 in 3 pages.
Fluid Transients in Systems by Wylie et al., Prentice Hall (1993) pp. 59-70.
PCT Search Report and Written Opinion dated Aug. 16, 2007 in 6 pages.
Supplementary European Search Report for European Application No. 03770516.7 dated Aug. 6, 2007 in 3 pages.
Extended European Search Report for European Application No. 07015011.5 dated Sep. 4, 2007 in 6 pages.
International Search Report and Written Opinion for International Application No. PCT/US2009/065815, Notification mailed Jan. 26, 2010.

* cited by examiner

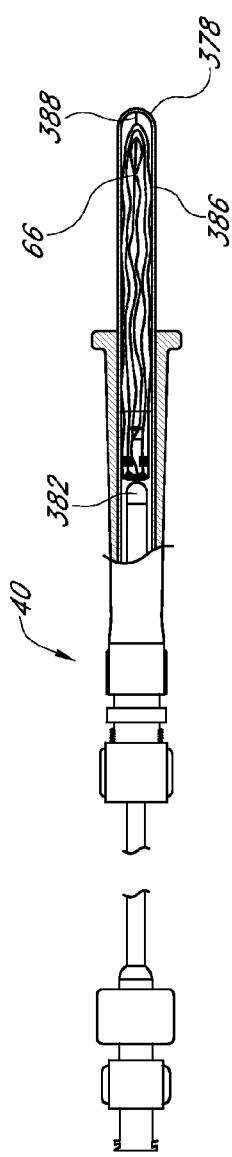
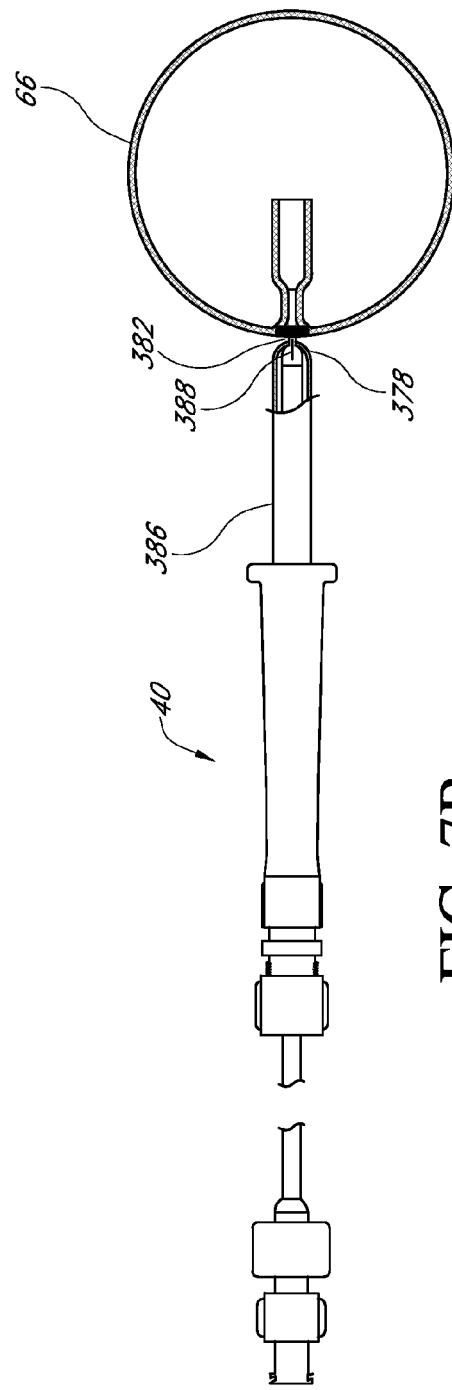
FIG. 7A
FIG. 7B

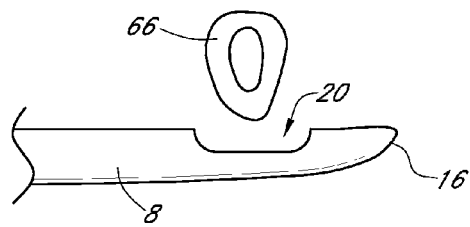
FIG. 10A
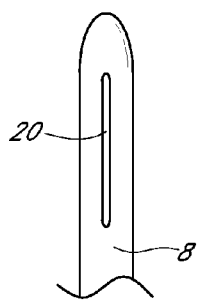
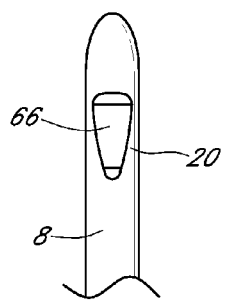
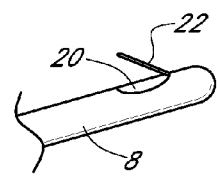
FIG. 10B  FIG. 10C  FIG. 10D
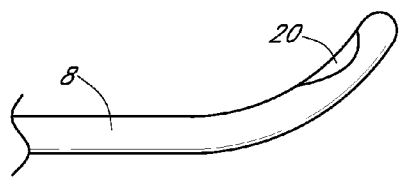
FIG. 10E

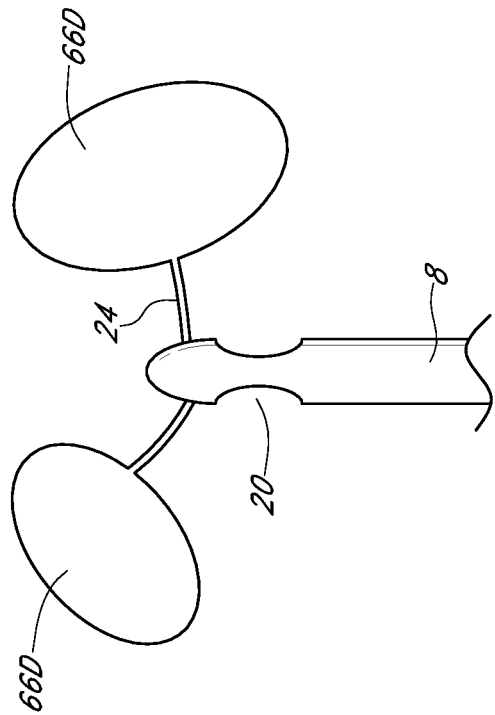
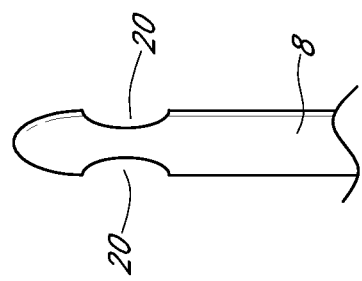
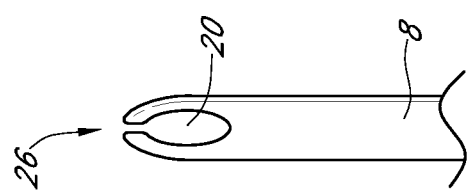
FIG. 11C
FIG. 11B
FIG. 11A

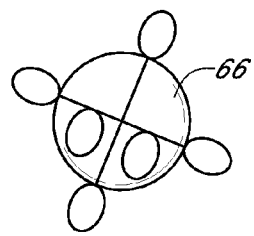 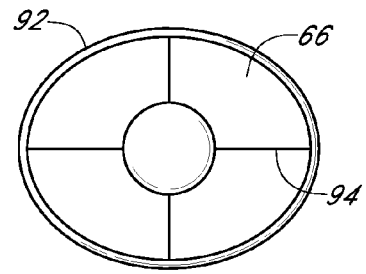
FIG. 23E FIG. 23F
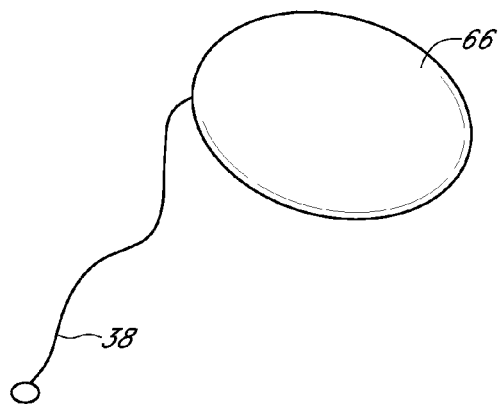 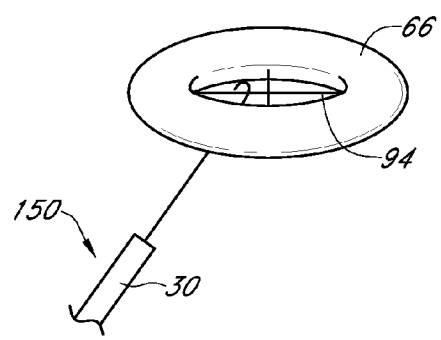
FIG. 23G FIG. 23H

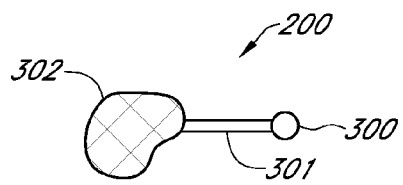
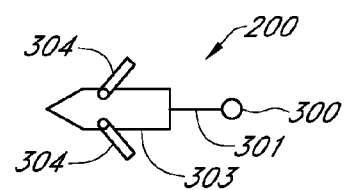
FIG. 47A  FIG. 47B
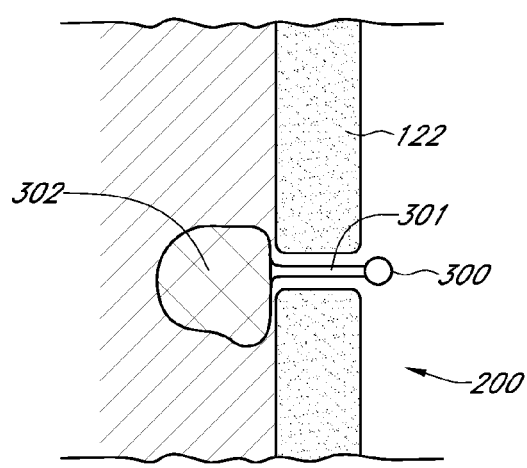
FIG. 47C

INFLATABLE IMPLANT DELIVERY SYSTEM AND METHOD

CROSS-REFERENCE TO RELATED APPLICATION

This application is a continuation of U.S. patent application Ser. No. 12/625,508 filed Nov. 24, 2009, which claims priority to U.S. Provisional Patent Appl. Nos. 61/200,147, filed Nov. 25, 2008, and 61/211,515, filed Mar. 31, 2009. The disclosures of the aforementioned applications are hereby incorporated in their entirety herein by reference. Any and all priority claims identified in the Application Data Sheet, or any correction thereto, are hereby incorporated by reference under 37 CFR 1.57.

This application is also related to U.S. patent application Ser. No. 12/343,120 filed Dec. 23, 2008, now U.S. Pat. No. 8,298,132; U.S. patent application Ser. No. 10/391,448 filed Mar. 17, 2003, now U.S. Pat. No. 7,470,228; U.S. patent application Ser. No. 10/391,446, filed Mar. 17, 2003, now U.S. Pat. No. 6,976,950; U.S. Provisional Patent Appl. No. 60/415,949, filed Oct. 3, 2002; U.S. patent application Ser. No. 09/723,309, filed on Nov. 27, 2000, now U.S. Pat. No. 6,682,473; and U.S. Provisional Patent Appl. No. 60/197,095, filed Apr. 14, 2000. The disclosures of the aforementioned applications are hereby incorporated in their entirety herein by reference.

BACKGROUND OF THE INVENTION

The present invention relates generally to medical devices and methods and apparatus related thereto for use within the body. The medical devices can include pressurized therapeutic devices, implants, implant delivery devices, implant retrieval devices, expandable membrane enclosures or balloons, sponges, attenuators, space occupying members, space creating devices, drug delivery devices, data collection devices, nerve stimulation devices, wave producing devices, vibration producing devices, pressure sensing devices, chemical sensing devices, volume sensing devices, and therapeutic devices. The medical devices can be used for many different purposes and in many places within the body including, but not limited to the following systems of the human body: cardiovascular, pulmonary, renal/urological, gastrointestinal, hepatic/biliary, gynecological, neurological, musculoskeletal, otorhinolaryngical and ophthalmic, as well as in and around organs of the body and in intra- and inter-organ space.

In some embodiments, methods and devices for maintenance of inflated implants within the body over time is discussed. In some embodiments, methods and devices for space creation or expansion within the body is discussed. In some embodiments, the treatment of disorders or pathological symptoms of the urinary tract caused by sudden fluctuations of intravesical pressure is discussed.

An example of a problem where there is a need for improved medical devices and methods is dealing with pressure events in the body. Pressure changes are known to propagate through incompressible or compressible fluids in various organs of the body. These pressure events or changes may be caused by a number of events including events within the body, such as a beating heart, breathing in the lungs, peristalsis actions in the GI tract, movement of the muscles of the body, or events such as coughing, laughing, external trauma to the body, and movement of the body relative to gravity. As the elasticity, or compliance, of the surrounding tissues and organs decreases, the propagation, magnitude, or amplitude of these pressure changes, waves, or events increases. These pressure events have many undesirable effects ranging from discomfort, to stress on the organs and tissue, to fluid leakage such as urinary incontinence, to renal failure, stroke, atherosclerosis, heart attack and blindness.

SUMMARY OF THE INVENTION

Embodiments of the medical devices, apparatus and methods described herein seek to overcome various problems in the medical field, including those described above. From this disclosure it will be appreciated that although certain examples are provided, the methods and devices herein can be used to provide similar or different treatments at the same or other sites within or in pressure communication with the body.

Certain embodiments comprise a method of treating a condition affecting the bladder. The method can include the steps of implanting a device into a human or animal body. The condition affecting the bladder can comprise: urinary incontinence, urinary tract cancer, an infection affecting the bladder, or an inflammatory, condition affecting the bladder.

Different embodiments of delivery systems can be configured to deliver an implant into a bladder. Some delivery systems can comprise a guide body, an implant advancer at least partially within the guide body and a syringe. The guide body can comprise a transurethral body sized to guide the delivery system through a urethra and a depth stop surface at a proximal end of the transurethral body. The syringe can have a conduit with a distal end of the conduit configured to couple to an implant, wherein at least a portion of the conduit is within the implant advancer. The implant advancer and the syringe can be configured to slide relative to the guide body after the transurethral body has been inserted into the urethra to thereby deliver an implant into the bladder. In some embodiments, the transurethral body has a lateral opening operable to deliver said implant away from a trigone region.

An implant delivery system can be configured to deliver an inflatable implant into a bladder via a urethra. The delivery system can comprise an elongate tubular body, an inflation tube and an implant decoupler. The tubular body can comprise a central lumen configured to hold an inflatable implant in an initial un-inflated state for delivery of the implant into the bladder. A method of use can include passing a distal tip of the elongate tubular body into the bladder. The implant can be inflated and released into the bladder.

A method of delivering an implant within a bladder according to certain embodiments can include the following steps. Inserting a transurethral body into a urethra. The transurethral body can be part of an implant delivery system having a guide body having the transurethral body and a meatal stop and an advancer. Placing the meatal stop against a meatus. Inserting a distal tip of the transurethral body within a bladder. Injecting liquid PFC into said implant. Moving an implant into the bladder with the advancer. Inflating an implant with air. Releasing the implant from the delivery system. Removing the delivery system from the bladder.

Some methods can further comprise additional steps such as: identifying a back wall of the bladder, wherein releasing the implant further comprises releasing the implant in a direction away from the trigonal area, wherein injecting further comprises injecting the liquid PFC into the implant prior to the step of moving the implant into the bladder, and wherein injecting further comprises injecting the liquid PFC into the implant prior to releasing the implant from the delivery system.

An additional method of delivering an implant within a bladder can comprise the steps of: inserting a cannulated delivery device within a urethra; passing a distal tip of said delivery device beyond a bladder sphincter into the bladder; causing or allowing an implant to expand out of a lateral aspect of said delivery device wherein said expansion occurs in a direction substantially opposite to that of a trigone region of the bladder and wherein said expansion is operable to open a flap or aperture of said aspect; disengaging said implant from said removal device; and removing said delivery device.

According to some embodiments, an implant delivery system can be configured to deliver an inflatable implant into a bladder via a urethra. The delivery system can comprise an elongate tubular body, an inflation tube and an implant decoupler. The elongate tubular body can be sized to pass through a urethra into a bladder. The tubular body can comprise a central lumen configured to hold an inflatable implant in an initial un-inflated state for delivery of the implant into the bladder and a lateral opening operable to deliver the inflatable implant from the central lumen into the bladder away from a wall of the bladder. The inflation tube can be positioned within the central lumen of the tubular body, the inflation tube configured to couple with the inflatable implant to allow inflation of the inflatable implant from within the tubular body. The implant decoupler can be positioned within the central lumen of the tubular body around the inflation tube. The implant decoupler can be configured to decouple the inflatable implant from the inflation tube after inflation of the inflatable implant from the un-inflated state to an inflated state.

In some embodiments, a method of delivering an inflatable implant into a bladder via a urethra can include one or more steps. The one or more steps can include the at least one of the following. Inserting an elongate tubular body of a delivery device within a urethra, the elongate tubular body comprising a central lumen holding an inflatable implant in an initial un-inflated state for delivery of the implant into a bladder. Passing a distal tip of the elongate tubular body into the bladder. Inflating the implant and thereby advancing the implant from within the central lumen to outside of the central lumen and into the bladder. Disengaging the inflatable implant within the bladder from said delivery device. Removing the delivery device from the bladder.

According to some embodiments, the method may include one or more of the following additional steps. Inflating the implant can further comprise expanding the implant out of a lateral opening of the elongate tubular body. Expanding can further comprise expanding the implant out of the lateral opening in a direction substantially opposite to that of a trigone of the bladder. Expanding can further comprise expanding the implant out of the lateral opening in a direction towards a dome of the bladder.

Further features and advantages of the present invention will become apparent to those of skill in the art in view of the detailed description of preferred embodiments which follows, when considered together with the attached drawings and claims.

BRIEF DESCRIPTION OF THE DRAWINGS

In order to better understand the disclosure and to see how it may be carried out in practice, some preferred embodiments are next described, by way of non-limiting examples only, with reference to the accompanying drawings, in which like reference numerals denote corresponding though not necessarily identical features consistently throughout the embodiments in the attached drawings.

FIG. 7A is an elevated side view of one embodiment of a delivery system.

FIG. 7B is an elevated side view of the delivery system of FIG. 7B with the implant ejected.

FIGS. 10A-E show different embodiments of a tip or end portion of a transurethral body for a delivery system.

FIGS. 11A-C show an additional embodiment of a tip or end portion of a transurethral body for a delivery system with a dumbbell shaped implant.

FIGS. 13A-E show different embodiments of different shaped needle or conduit cross-sections taken along line A-A of FIG. 13.

FIGS. 23A-H illustrate different shapes and configurations of implants designed to enhance retrieval.

FIGS. 47A-F show various tissue and bone anchor embodiments having inflatable membrane enclosures.

DETAILED DESCRIPTION OF THE PREFERRED EMBODIMENT

Figure 1:
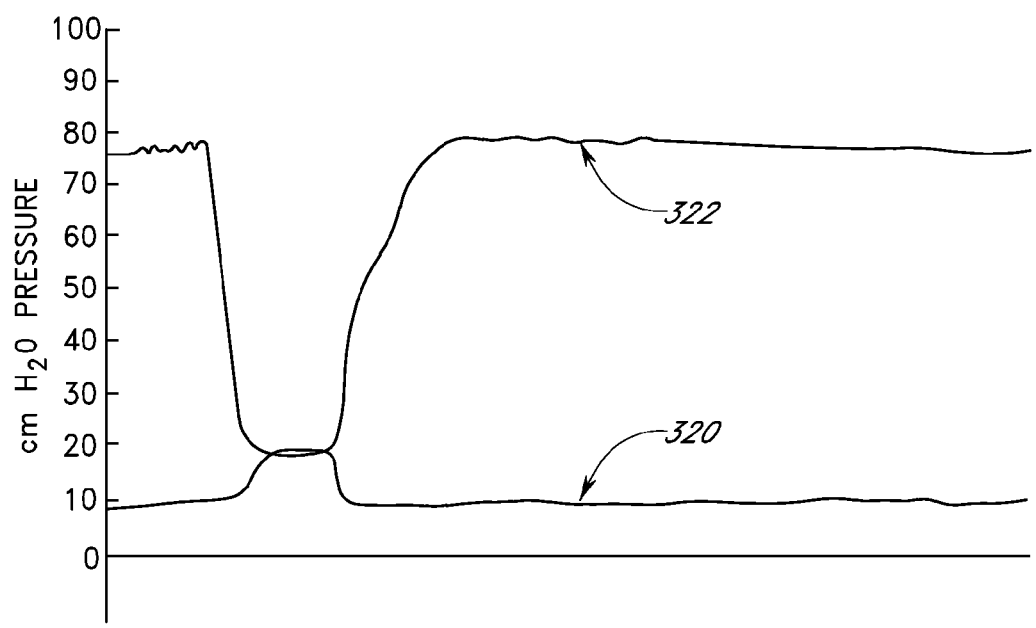
FIG. 1 illustrates maximum urethral pressure against intravesical pressure during normal voiding.

Medical devices, methods, and apparatus related thereto for use within the body are disclosed. The medical devices can include pressurized therapeutic devices, implants, implant delivery devices, implant retrieval devices, expandable membrane enclosures or balloons, sponges, attenuators, space occupying members, space creating devices, drug delivery devices, data collection devices, nerve stimulation devices, wave producing devices, vibration producing devices, pressure sensing devices, chemical sensing devices, volume sensing devices, and therapeutic devices. The medical devices can be used for many purposes and in many places within the body including, but not limited to the following systems of the human body: cardiovascular, pulmonary, renal/urological, gastrointestinal, hepatic/biliary, gynecological, neurological, musculoskeletal, otorhinolaryngical and ophthalmic, as well as in and around organs of the body and in intra- and inter-organ space.

In one particular aspect, the disclosure relates generally to the field of urology and gynecology, and in particular to the treatment of disorders of the urinary tract caused by sudden fluctuations of intravesical pressure. More specifically, in this aspect methods and devices are provided for the diagnosis and treatment of urinary disorders such as incontinence, urgency, frequency, interstitial cystitis, irritable bladder syndrome and neurogenic bladders.

Various embodiments of pressurized therapeutic devices that maintain a given pressure and or volume over time despite gaseous exchange are provided, other embodiments inflate or deflate over a given time period and further embodiments provide a constant force against, within or between a tissue, vessel, organ, or body cavity. Certain embodiments are designed to maintain inflation in oxygen depleted environments.

Various instruments and implants are provided herein for the implantation of medical devices within the bladder via the urethra, open surgery or percutaneously through the abdomen, back, vagina, bowel, rectum, or perineum. Certain embodiments of the implantable medical device may comprise one or more expandable membrane enclosure or balloon, sponge, attenuator, space occupying member, drug delivery device, data collection device, nerve stimulation device, wave producing device, vibration producing device, pressure sensing device, chemical sensing device, volume sensing device, or a therapeutic device. From this disclosure it will be appreciated that although the examples provided deal primarily with intravesical applications the methods and devices herein can be used to provide treatment at sites adjacent the bladder or between layers of bladder tissue. Further, the devices and methods herein may be used or applied within or proximal to other organs and sites in the body such as the heart, lung, cranium, cardiovascular system, breasts, abdominal area or cavity, eye, testicles, intestines, stomach, or other organs or tissues.

Some embodiments are directed to methods and apparatus for measuring and/or attenuating and/or baffling transient pressure waves in relatively incompressible materials in organs of the body. Illustrative embodiments discussed below relate generally to the fields of urology and gynecology, and in particular to the treatment of disorders of the urinary tract exacerbated by sudden fluctuations in intravesical pressure. However, as will be readily understood by those skilled in the art, and as described below, the devices and methods are not limited to the fields of urology and gynecology and methods and apparatuses of embodiments disclosed herein may be used in other organs of the body as well to attenuate and/or baffle pressure transients or reversibly occupy intraorgan or interorgan space.

Certain embodiments dampen transient intravesical pressure including pressure spikes experienced by the urinary tract. During a transient pressure event, the bladder becomes a relatively non-compliant environment due to a number of factors including the pelvic skeletal structure, the compressive loads of contracting tissues bounding the bladder or the decreased compliance of the musculature, incompressible behavior of urine, nerve or connective tissue of the bladder. Factors contributing to the reduced compliance of the bladder are aging, anatomic abnormalities or trauma to the structures of the pelvis and abdomen.

Urine is primarily composed of water and is virtually incompressible in the typical pressure ranges present within the human bladder. The relationship between the maximum urethral pressure and the intravesical pressure for normal voiding of the bladder is well defined. With reference to FIG. 1, relaxation of the urethra occurs before the detrusor muscle contracts to cause the intravesical pressure 320 to exceed the urethral pressure 322 during normal voiding. As would be obvious to one skilled in the art, the pressures discussed herein are gauge or relative pressures except where absolute pressures and/or atmospheric pressures are specifically mentioned.

Figure 2:
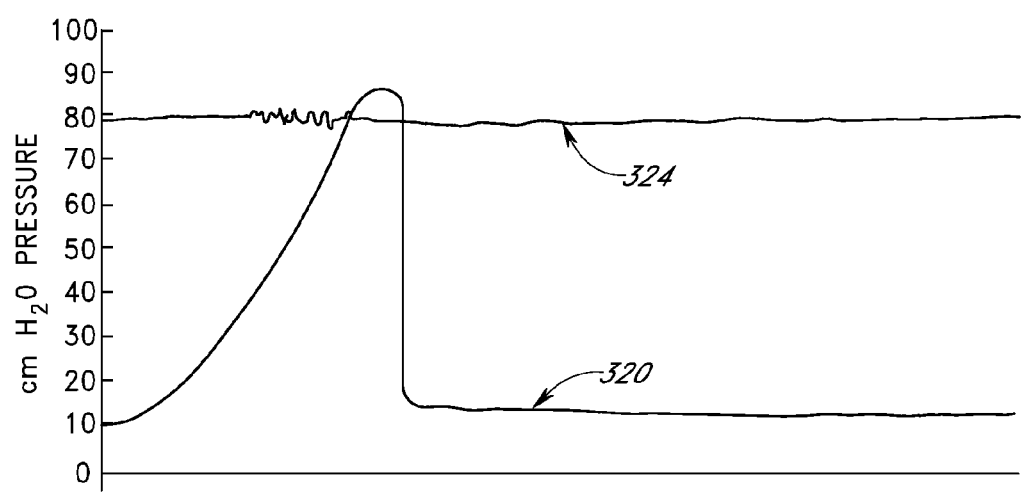
FIG. 2 illustrates the intravesical pressure exceeding the maximum urethral pressure in a noncompliant bladder.

The bladder serves two mechanical functions: 1) low-pressure storage and 2) high-pressure voiding. During the storage or filling phase, the bladder receives urine from the kidneys. Compliance of the bladder is defined as the ratio of the change in volume to the change in pressure, and the static compliance of the bladder is measured during a typical urodynamic evaluation. The static compliance index is measured by filling the bladder to cystometric capacity and allowing the pressures to equilibrate for a time period of approximately sixty seconds. The static compliance index is calculated by dividing the bladder capacity by the detrusor pressure at the end of filling. A normal bladder will typically exhibit static compliance between 15 and 30 ml/cm $H_2O$. A low static compliance bladder typically will have a compliance index of less than 10 ml/cm $H_2O$. With reference to FIG. 2 which illustrates different pressures for a non-compliant bladder, a low static compliance bladder typically is poorly distensible and has a high end-filling pressure. The intravesical pressure 320 increases to higher levels to exceed the maximum urethral pressure 324. The steady state or static compliance of the bladder is used to diagnose patients with neuropathic problems such as damage to the lower motor neurons, upper motor neurons, or multiple sclerosis. In addition, the steady state compliance of the bladder is also used, in some cases, to attempt to diagnose problem of incontinence, including urgency, frequency and cystitis.

In general, intravesical pressure spikes result from volumetric tissue displacement in response to gravity, muscular activity or rapid acceleration. The lack of compliance of the bladder and the urine contained in the bladder with respect to events of high frequency, result in minimal fluidic pressure attenuation of the higher frequency pressure wave(s) and results in high intravesical pressures that are directly transmitted to the bladder neck and urethra, which may or may not cause detrusor contractions. Under these conditions, the urethra may act as a volumetric pressure relief mechanism allowing a proportional volume of fluid to escape the bladder, to lower the intravesical pressure to a tolerable level. The urethra has a maximum urethral pressure value, and when the intravesical pressure exceeds the maximum urethral pressure, fluid will escape the bladder. Under these conditions, nerve receptors in the bladder and/or bladder neck and/or trigone trigger a detrusor contraction that may lead to micturition (frequency) or may subside without micturition (urgency) or may lead to the intravesical pressure exceeding the maximum urethral pressure resulting in fluid escaping the bladder (incontinence). Under these conditions, waves hitting and/or expanding the bladder wall, may cause a patient with cystitis to exhibit significant pain.

Incontinence is common in males who have undergone radical prostatectomy, particularly where the sphincter has been compromised. In these patients, attenuation in the bladder reduces the intravesical peak pressures, resulting in less urine leakage. The attenuation requirements in these patients can include short duration pressure changes—such as, for example, 50 to 400 ms—and long duration pressure changes—such as, for example, greater than 500 ms—depending on the magnitude of damage to the urinary sphincter.

The inventors of the present application have recognized that for the vast majority of patients suffering from problems of urinary tract disorders such as frequency, urgency, stress and urge incontinence and cystitis, the cause and/or contributor to the bladder dysfunction is a reduction of overall dynamic bladder compliance rather than steady state bladder compliance. These patients may often have bladders that are compliant in steady state conditions, but have become non dynamically compliant when subjected to external pressure events having a short duration of, for example, less than 5 seconds or in some cases less than 2 seconds or even less than 0.01 seconds. Reduction in dynamic compliance of the bladder is often caused by some of the same conditions as reduction of steady state compliance including aging, use, distention, childbirth and trauma. The anatomical structure of the bladder in relation to the diaphragm, viscera, and uterus (for women) causes external pressure to be exerted on the bladder during talking, walking, laughing, sitting, moving, turning, and rolling over.

Figure 3:
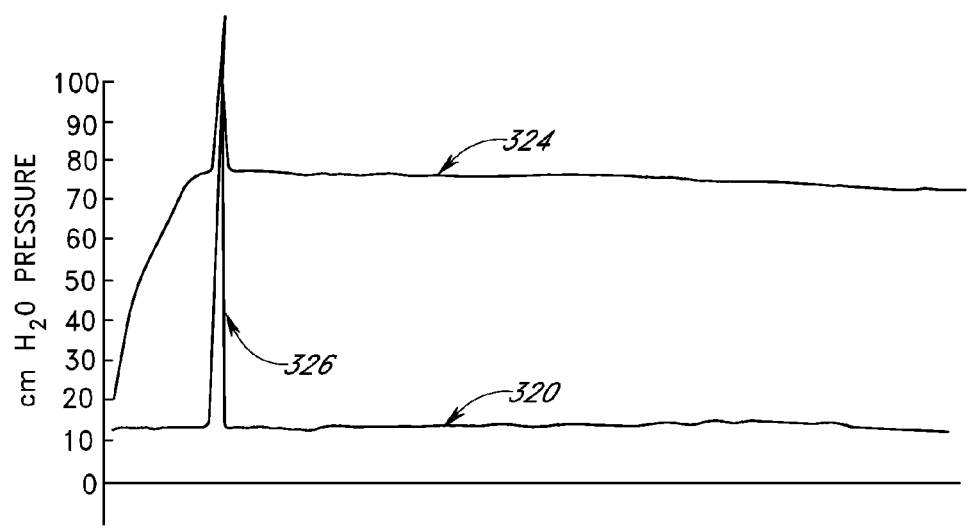
FIG. 3 illustrates an intravesical pressure spike exceeding the maximum urethral pressure during stress incontinence.

The relationship between intravesical pressure 320 and the maximum urethral pressure 324 for a patient suffering from stress incontinence due to lack of dynamic compliance in the bladder is illustrated in FIG. 3. When the patient coughs (or some other stress event occurs), a spike 326 will occur in the intravesical pressure. Intravesical pressure spikes in excess of 120 cm $H_2O$ have been urodynamically recorded during coughing, jumping, laughing or sneezing. When the intravesical pressure exceeds the maximum urethral pressure value, leakage occurs. In order to retain urine during an intravesical pressure spike, the urinary retention resistance of the continent individual needs to exceed the pressure spike. Urinary retention resistance can be simplified as the sum total of the outflow resistance contributions of the urethra, bladder neck and meatus. In female patients, it is generally believed that the largest resistance component is provided by the urethra. One measure of urinary resistance is the urodynamic measurement of urethral leak pressure. The incontinent individual typically has a urethral leak pressure less than 80 cm $H_2O$. The decline of adequate urinary retention resistance has been attributed to a number of factors including reduced blood flow in the pelvic area, decreased tissue elasticity, neurological disorders, deterioration of urethral muscle tone and tissue trauma.

In practice, the urethral leak point pressure is determined by filling the bladder with a known amount of fluid and measuring the intravesical and abdominal pressures when there is a visible leak from the urethra while the patient is "bearing-down" (valsalva). With an attenuation device in the bladder, the measured intravesical leak point pressure typically increases due to the absorption of some the abdominal energy by the attenuation device. In this case, the patient has to push harder to achieve the same intravesical pressure. Since the abdominal muscles and muscles surrounding the urethra both contract simultaneously during a valsalva maneuver, the measured intravesical leak point pressure and urethral resistance increases when the attenuation device is in the bladder.

Figure 4A:
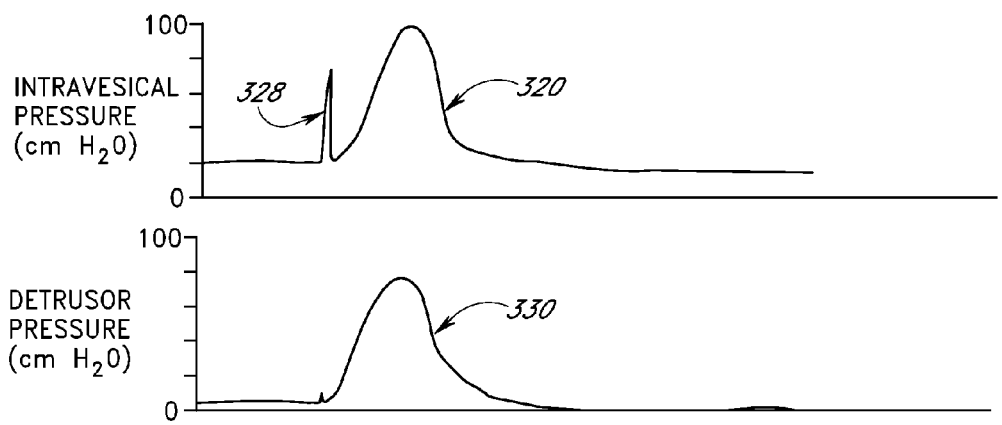
FIG. 4A illustrates the relationship between intravesical pressure and detrusor pressure during cough-induced urgency or frequency.
Figure 4B:
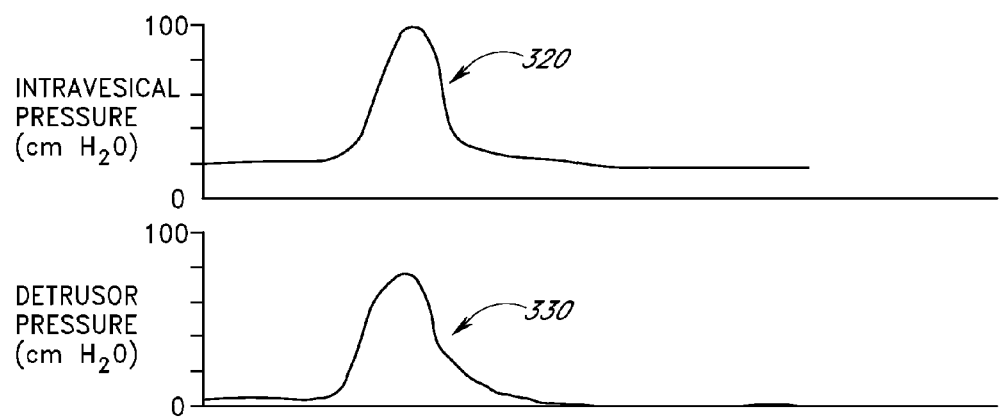
FIG. 4B illustrates the relationship between intravesical pressure and detrusor pressure during non-cough-induced urgency or frequency.

Urinary disorders, such as urgency, frequency, otherwise known as overactive bladder, and interstitial cystitis are caused or exacerbated when rapid pressure increases or rapid volume increases or other irritable conditions within the bladder cause motor neurons to send signals to the brain to begin the cascade of events necessary for urination. External pressure exerted on the bladder may result in a detrusor contraction that may result in urgency, frequency or incontinence. See FIG. 4A (cough-induced urgency/frequency) and 4B (non-cough-induced urgency/frequency). With reference to FIG. 4A, a coughing event 328 induces increased intravesical pressure 320 which results in increased detrusor pressure 330. An increase in the detrusor pressure 330 generally is associated with increased urgency, frequency, or incontinence. Urinary disorders such as interstitial cystitis or irritable bladder conditions are a chronic inflammatory condition of the bladder wall, which includes symptoms of urgency and/or frequency in addition to pain. Therefore, the problem of a pressure spike in the functionally noncompliant bladder can be further exacerbated by a nearly simultaneous contraction of the bladder and a relaxation of the urethra.

Some embodiments provide methods and devices for treating and/or compensating for reduced dynamic compliance of the bladder. In one embodiment, a device having a compressible element is placed within the human urinary bladder, in a manner that allows the compressible element to act as a pressure attenuator to attenuate transient pressure events. The term attenuator refers generally to devices that attenuate pressure, force, or energy by dissipating or dampening the pressure, force, or energy. Gases, such as atmospheric air, carbon dioxide, nitrogen, and certain perfluorocarbons (PFC) are very compressible in the pressure ranges typically encountered in the human bladder, and may be used in attenuation devices inserted in the bladder. Furthermore, when compared to the tissues encompassing urine, gases are significantly more compliant than the immediate environment. The addition of a volume of gas acts as a low rate spring in series with the native fluidic circuit of the urinary tract.

In accordance with one embodiment, an attenuation device is placed within the human urinary bladder. The attenuation device can be a pressurized container. The container can take many forms including a sphere. The attenuation device is intended to be untethered in the bladder and is intended to remain in the bladder for between several hours and one year, between one week and six months, or between one day and three months. The attenuation device is a small elastomeric gas cell with a relaxed (unstretched) volume of between 1 and 500 cc, more preferably between 10 and 180 cc and more preferably still, between 25 and 60 cc. The attenuation device is a unitary component but can be comprised of two or more subcomponents. The attenuation device can be made with or without a seam. The attenuation device has a substantially uniform wall thickness of between 0.25 inch to 0.0001 inch, more preferably between 0.0005 inch and 0.005 inch, but could vary greatly, and still perform the intended function. In the embodiment described above, attenuation devices having gas cells that are free-floating in the bladder have been described. In other embodiments, gas cells or similar attenuation devices could be surgically affixed to the bladder wall through the use of suture, staples and other accepted methods or placed submucosally or intramuscularly within the bladder wall. Other embodiments could also include attenuation devices with programmable, variable and adjustable buoyancy by using ballasting, specific inflation/deflation solutions, alternative materials of construction or by other means.

Figure 5:
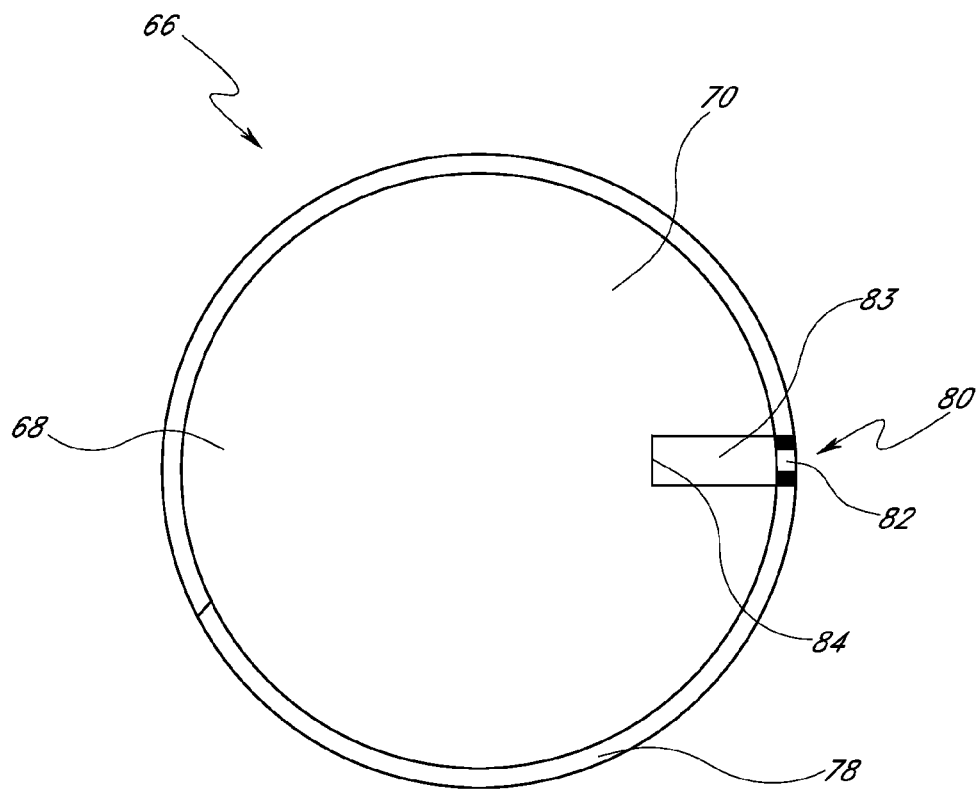
FIG. 5 is a schematic top plan view of an implant.
Figure 5A:
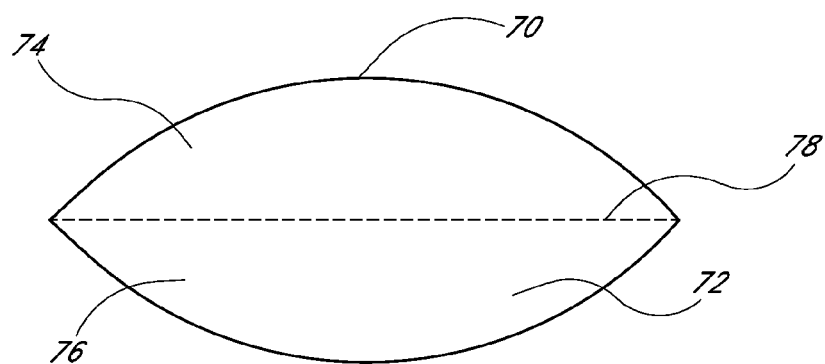
FIG. 5A is a side elevational view of FIG. 5.
Figure 5B:
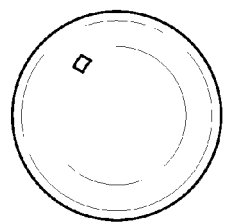
FIGS. 5B-G show various types and shapes of implants.
Figure 5C:
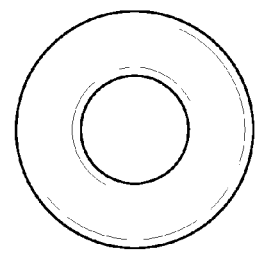
Figure 5D:
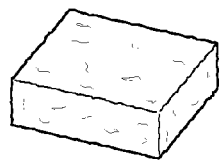
Figure 5E:
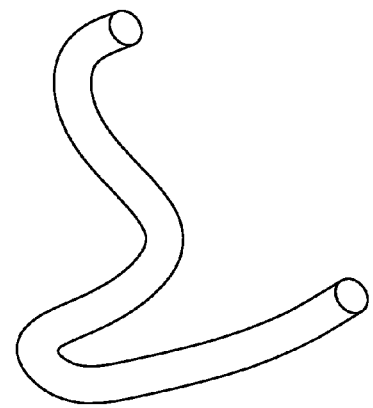
Figure 5F:
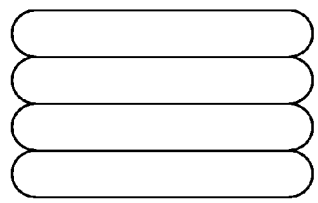
Figure 5G:
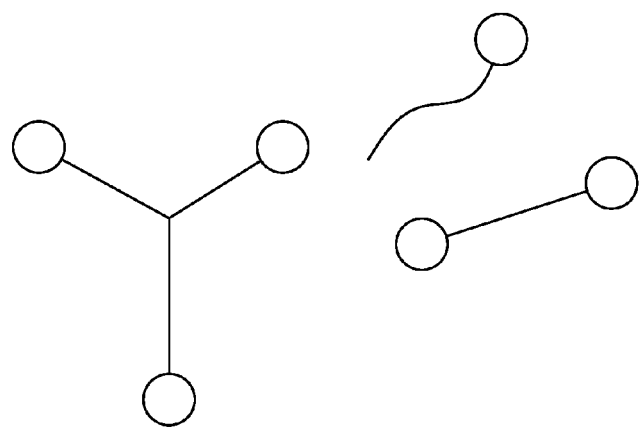

Referring to FIGS. 5 and 5A, one embodiment of attenuation device 66 is illustrated which comprises a moveable wall such as on an inflatable container 68. The inflatable container 68 is illustrated as having a generally circular profile, although other profiles may be utilized. The diameter of the inflatable container 68 may be varied within the range of from about 0.25 inches to about 6 inches in an embodiment involving the implantation of only a single attenuation device. Many embodiments of the inflatable containers 68 will have a diameter within the range from about 1 inch to about 3 inches, with a total volume within the ranges recited above. In general, the specific dimensions and configuration of the inflatable container 68 are selected to produce an attenuation device having a desired volume and a desired dynamic compression range, and may be varied from spherical to relatively flat as will be apparent to those of skill in the art based upon the disclosure herein. In certain embodiments, two or more discreet inflatable containers 68 are utilized. The sum of the volumes of the multiple containers will equal the desired uncompressed displacement.

The inflatable container 68 illustrated in FIGS. 5 and 5A comprises a flexible wall 70, for separating the contents of the attenuation device 66 from the external environment. Flexible wall 70 comprises a first component 74 and second component 76 bonded together such as by a seam 78. In the illustrated embodiment, the first component 74 and second component 76 are essentially identical, such that the seam 78 is formed on the outer periphery of the inflatable container 68.

Seam 78 may be accomplished in any of a variety of manners known in the medical device bonding arts, such as heat bonding, adhesive bonding, solvent bonding, RF or laser welding, or others known in the art.

The flexible wall 70, formed by a bonded first component 74 and second component 76, defines an interior cavity 72. As is discussed elsewhere herein, interior cavity 72 preferably comprises a media that can include a compressible component, such as gas, or foam. Other media or structures capable of reduction in volume through a mechanism other than strict compression may also be used. For example, a material capable of undergoing a phase change from a first, higher volume phase to a second, lower volume phase under the temperature and pressure ranges experienced in the bladder may also be used. In one embodiment, the media can comprise a liquid that forms a solid or foam after implantation. In some embodiments the media comprises a solid.

In order to minimize trauma during delivery of the attenuation device 66, the attenuation device is preferably expandable from a first, reduced cross-sectional configuration to a second, enlarged cross-sectional configuration. The attenuation device 66 may thus be transurethrally deployed into the bladder in its first configuration, and enlarged to its second configuration once positioned within the bladder to accomplish the pressure attenuation function. Preferably, a crossing profile or a greatest cross-sectional configuration of the attenuation device 66 when in the first configuration is no greater than about 24 French (8 mm), and, preferably, no greater than about 18 French (6 mm). This may be accomplished, for example, by rolling a deflated inflatable container 68 about a longitudinal axis, while the interior cavity 72 is evacuated. Once positioned within the bladder, the interior cavity 72 is filled with the media to produce a functional attenuation device 66.

To facilitate filling the interior cavity 72 following placement of the attenuation device 66 within the bladder, the inflatable container 68 is preferably provided with a valve 80. In the illustrated embodiment, valve 80 is positioned across the seam 78, and may be held in place by the same bonding techniques utilized to form the seam 78. Valve 80 may be omitted in an embodiment in which the attenuation device 66 is self-expandable.

Valve 80 generally comprises an aperture 82, for receiving a filling tube therethrough. Aperture 82 is in fluid communication with the interior cavity 72 by way of a flow path 83. At least one closure member 84 is provided for permitting one way flow through flow path 83. In this manner, a delivery system and filling device can be utilized to displace closure member 84 and introduce compressible media into the interior cavity 72. Upon removal of the filling device, the closure member 84 prevents or inhibits the escape of compressible media from the interior cavity 72 through the flow path 83.

Thus, the closure member 84 is preferably movable between a first orientation in which it obstructs effluent flow through the flow path 83 and a second position in which it permits influent flow through the flow path 83. Preferably, the closure member 84 is biased in the first direction. Thus, forward flow may be accomplished by either mechanically moving the closure member 84 into the second position such as using a filling tube, or by moving the closure member 84 into the second position by exerting a sufficient pressure on the compressible media in flow path 83 to overcome the closure bias. Any of a wide variety of valve designs may be utilized in the implant 66 as will be apparent to those of skill in the art in view of the disclosure herein.

Various coatings may be used to enhance the biocompatibility of the implantable devices and associated insertion or removal devices described herein. Lubricating coatings, substances, and substrates may be used to facilitate insertion or removal. In one embodiment, the device incorporates biocompatible coatings or fillers to minimize irritation to the bladder wall and mucosa and/or to inhibit the formation of mineral deposits (encrustation) or biofilm formation. Such device treatments may also inhibit films, deposits or growths within or on the surface of the device. Materials can be coated onto the surface or incorporated within the wall of the device. Biocompatible lubricating substances may be used to facilitate the placement of the attenuation device/fill tube within a lumen of an introducer.

FIGS. 5B-5G show various other types of implants. The implants shown can be used as attenuation devices or for other therapeutic, aesthetic, and/or medicinal purposes as discussed herein. Shapes and types of implants can include a sphere, toroid, hemi-toroid, egg-shaped, sponge, snake, cylindrical coil, coiled, tethered, disc-like, rod, flat envelope (i.e., two sheets with a seam around the edge), chain of beads, etc.

In certain other embodiments the cross-section of the implant is non circular such as oval, triangular, rectangular, or any other geometric shape. In another embodiment the cross-section is wavy, variable, irregular, repeating such as repeating series of linked spheres in fluid communication with each other. In yet another embodiment the implant is initially provided in the form of a rod, either solid or partially inflatable, that forms a short but wide spiral, or spring like device having one or more coils. This embodiment is particularly useful in environments wherein the transverse size or shape, e.g., diameter, of the treatment region is not certain or changes over time because the coil will tend to expand or contract accordingly.

Figure 5I:
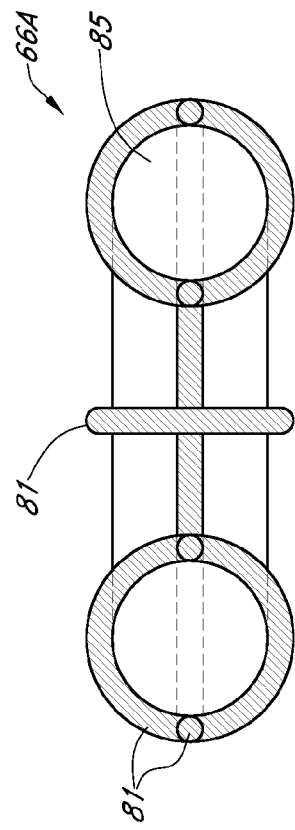
FIGS. 5H-I show a top and cross-sectional view of an implant.
Figure 5H:
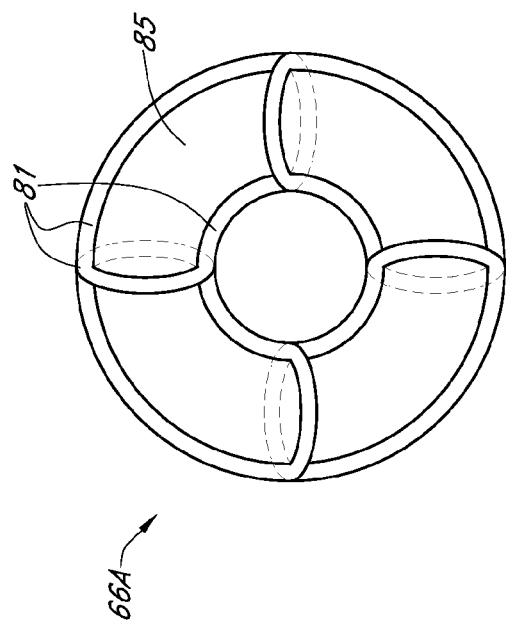

In some embodiments the implant is at least partially solid. For example, solid portions 81 can be added to an implant 66. The solid portions can serve many functions such as, structural support, drug delivery, expansion or compression limiters, etc. In some embodiments, the solid portions 81 can comprise a drug delivery device, such as a built-up drug deposit. For example, FIGS. 5H and 5I show an implant 66A in the shape of a toroid. The implant 66A can be an inflatable implant defining an enclosure 85. The enclosure 85 can be flexible. In some embodiments, the enclosure 85 can assume a first deflated configuration and a second expanded and inflated configuration. The implant 66A can be an attenuation device. The implant 66A can have solid portions 81 surrounding the device. As shown, the solid portions can be ribs on the enclosure 85 or ribs that at least partially surround the enclosure 85.

In some embodiments an implant can be configured to include one or more chambers or segments to serve specific functions. The chambers can contain various substances and can be for various purposes such as, for containing combinations of gases, liquids, and/or therapeutic agents.

Figure 5J:
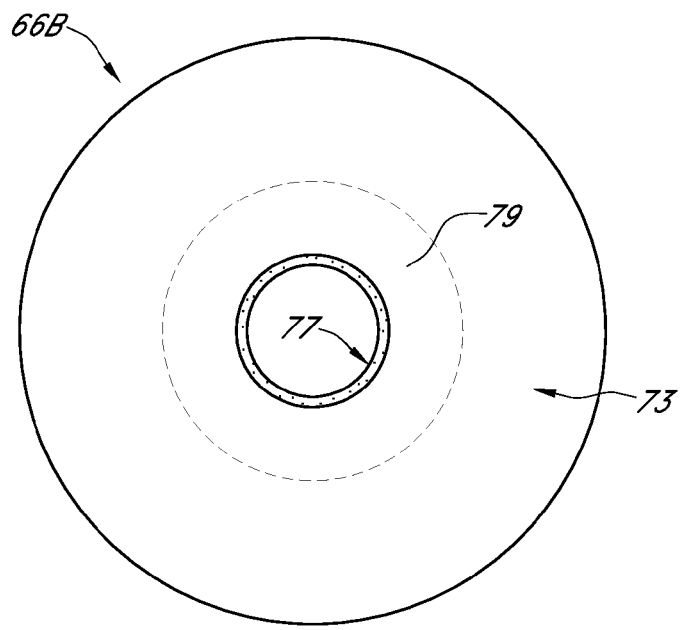
FIGS. 5J-K show a top and cross-sectional view of an implant.
Figure 5K:
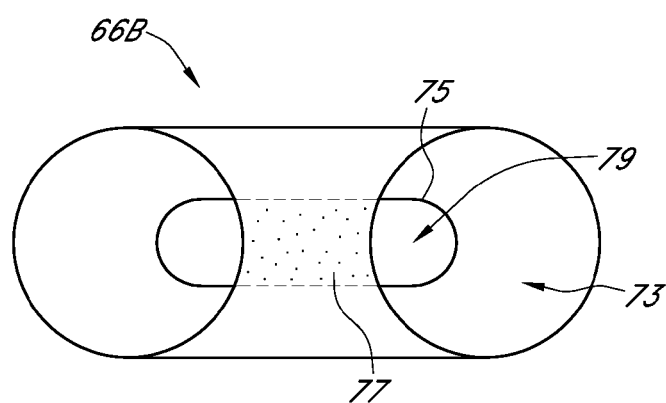

For example, FIGS. 5J and K show a toroid shaped implant 66B with two chambers 73, 79. In one embodiment one chamber 79 is filled with a drug and the other 73 is filled with an inflating media. The chambers 73, 79 can be separated by a wall 75. One or both of the chambers can be used as a drug delivery device. For example, chamber 79 can have holes 77 on the outer surface of the implant 66B to allow a drug to diffuse through the chamber wall into the implant's 66B surroundings. The size and density of the holes 77 in the film can be used to control the rate of drug flow from the chamber 79 to the bladder or other bodily region. In some embodiments, the outer surface or portions of the outer surface of the implant are permeable to certain substances such as, air or water. This can allow the substance to enter and leave the chamber. When the substance leaves the chamber it can take a drug or other chemical with it to the surroundings of the implant 66B.

Pressure on the inside of the implant 66 can also be used to control the rate of drug diffusion. In another embodiment, material selection and thickness is used to control the rate of drug release. In other embodiments, barrier layers and multilayered structures are used to obtain the desired diffusion rate. For example, the outside surface of the implant 66 can be configured to have barrier layers or be multilayered. Barrier layer selection can be used in addition to, or without coatings to control the diffusion rates of chemicals and gases within the implant. Finally, in certain other embodiments a spring and chamber, or piston can be used to create a near constant pressure on the drug and control the rate of release.

Figure 5L:
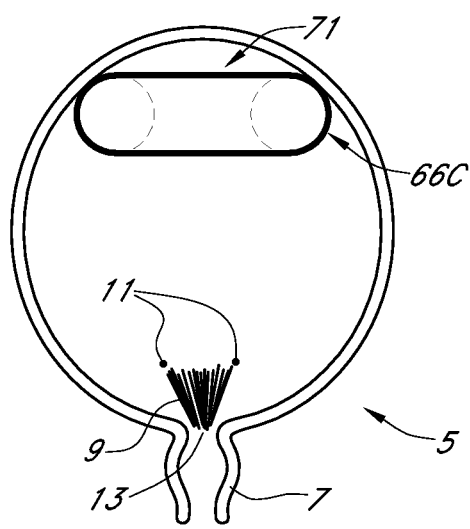
FIG. 5L shows a toroidal implant within the bladder when the bladder is full.

The human urinary bladder is a solid, muscular, and distensible organ that sits on the pelvic floor. It collects urine excreted by the kidneys prior to disposal by urination. Urine enters the bladder 5 via the ureters 11 and exits via the urethra 7 (FIG. 5L).

The walls of the bladder are mostly comprised of muscle tissue. This muscle tissue is known as the detrusor muscle, and is a layer of the urinary bladder wall made of smooth muscle fibers arranged in spiral, longitudinal, and circular bundles. When the bladder is stretched, nerves are activated which signals to the parasympathetic nervous system to contract the detrusor muscle. This encourages the bladder to expel urine through the urethra. For the urine to exit the bladder, both the internal sphincter and the external sphincter need to open. The urinary bladder can contain a wide range of urine volumes, from 0 to as much as 600 ml of urine. Typically, in a female, bladder urine volumes in the bladder range from 0 to 300 ml. Typically, in a female, a full bladder will contain 250 to 300 ml.

The neck of the bladder 13 is the area immediately surrounding the urethral opening; it is the lowest and most fixed part of the organ. In the male it is firmly attached to the base of the prostate, a gland that encircles the urethra. The bladder neck 13 is commonly more or less funnel-like in shape. The angle of inclination of the sides of this funnel varies based on the degree to which the bladder is full, and also varies during filling and emptying of the bladder. A very full distended bladder will have a bladder neck 13 with more oblique walls, and a bladder that is emptying or empty will be more acute. The posterior portion of the bladder neck 13 that is contiguous with the base of the bladder has a region containing a high density of sensory nerves. This region is triangular in shape and is known as the trigone region 9. This inverted triangle defined by the urethra 7 (the vertex of the triangle) and the ureteral orifices 11 at each corner of the base of the triangle. The ureteral orifices are the locations where the ureters enter the bladder.

The highest concentration of sensory nerve receptors in the bladder can be found in the trigone region 9. Anything that causes pressure, friction, or irritation on this region can cause a number of morbidities, including urgency, frequency, pain and/or irritation. The bladder neck 13 contains stretch receptors, and anything that lodges in or otherwise stretches the bladder neck will likewise be very uncomfortable. When designing a device that is to reside in whole or in part in the bladder, the comfort of that device will be significantly impacted by the device's ability to minimize or avoid contact with these two particularly sensitive areas.

In addition, the bladder does not contract or expand uniformly. For example, when the bladder is full it is quasi-spheroid or ovoid in shape. Its muscular walls are stretched out. During micturition, as the bladder empties, the superior and inferolateral walls contract. Wrinkles, or rugae, form in these walls as they shrink. The bladder neck and trigone area is more firmly anchored to underlying tissue and does not shrink as significantly or form rugae. Consequently the shrinkage of the bladder is not uniform and most of the reduction in size comes from the shrinkage of the superiolateral and inferolateral walls, and from the superior wall, or dome, becoming convex as it collapses towards the trigone and bladder neck area Accordingly, intravesical implants can preferably be configured to avoid, or not be capable of entering the bladder neck 13 and trigone area 9. This can reduce or eliminate irritation to these sensitive areas containing the majority of the pain receptors in the bladder. Also, recognizing the non-uniform contraction of the bladder as it empties, other embodiments can include devices that reside in the folded perimeter of the bladder and/or comprise an open center (such as a toroid) or perforated center (i.e. a central region that permits flow through) that does not contact the sensitive trigone area, and optionally can remain in a relatively fixed location.

If the implant gets too large, then it can occupy too much of the volume of the bladder and diminish its capacity to the point where the patient will need to urinate more frequently. Such a device will diminish the "functional capacity" of the bladder. Accordingly, one or more embodiments of devices are adapted to not occupy more than 10% of a typical functional capacity which corresponds to 25 to 30 ml in women, and up to twice that amount in men. In other embodiments, the volume of the implant can be as high as 20%-50% of functional capacity or in extreme cases at or beyond functional capacity.

One or more implants provided herein may be suitable for providing a platform for an intravesical device comprising a drug delivery device, data collection device, attenuation device, nerve stimulation device, wave producing device, vibration producing device, pressure sensing device, chemical sensing device, volume sensing device, pH sensing or a therapeutic device.

Figure 5M:
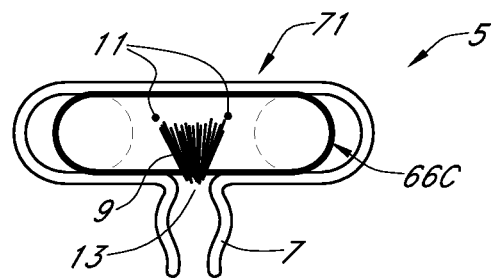
FIGS. 5M-N show a toroidal implant within the bladder when the bladder is empty.
Figure 5N:
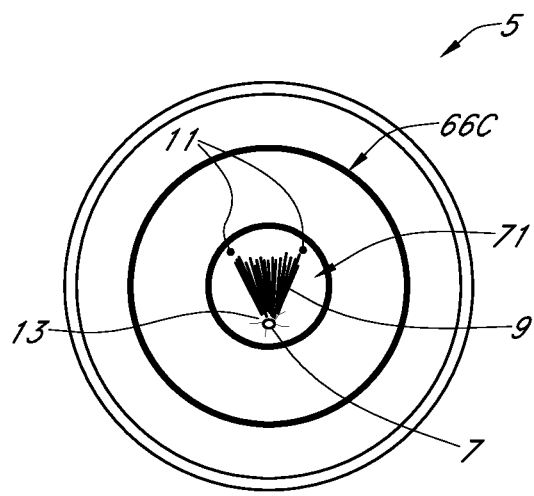

In one embodiment, an implant 66C is ring or toroid shaped, as shown in FIG. 5L. The implant 66C can be adapted within the bladder 5 such that after implantation it resides above the trigone region 9 and bladder neck 13 and is incapable of entering the trigone region 9 and bladder neck 13 when the bladder is full (FIG. 5L), empty (FIGS. 5M and N) or in the process of being filled.

In one or more embodiments the outer diameter of a ring, toroid, or coiled implant can be around 1 inch to 6 inches, and more preferably 2.5 inches to 4.5 inches. The cross sectional diameter of the implant can vary from about 0.050 inches to about 1 or 2 inches. In certain embodiments, the implant can define a central region or void 71. The central region 71 can be configured to minimize contact with sensitive regions of the body, such as the trigone 9, bladder neck 13, etc. The central region 71 can allow for the passage of urine out through the urethra and to not interfere with normal urination. The selection of the size of the central region 71, such as the inner diameter of a toroid shaped implant, can be critical in avoiding contact of the intravesical device with the trigone region or bladder neck when the bladder is empty or nearly empty. Given the typical size of the trigone; toroid, ring, coiled devices, or other shaped devices can have an inner opening of about 0.1 inches to 5.5 inches, more preferably about 1.5 inches to 4 inches, or more preferably greater than about 1 inch.

In another embodiment, the central region of the implant is traversed by one or more extensions that may further define a central hub. In certain other embodiments, the central area comprises a membrane that is porous or comprises one or more holes that allow for the passage of bodily fluids. The inner area can be a membrane that can serve as a "platform" of sorts. The area can be perforated in any pattern to allow urine to pass through and also serve as a platform for other components such as an infuser, transducer, or coating. The components can be used for, pressure monitoring, drug delivery, electrical pulse delivery, pressure wave delivery etc. The ring itself, hub, central regions or extensions can contain or deliver therapeutic agents and further comprise a pump, infuser, or other dosing system as provided infra. Alternatively, components of the implant can comprise a transducer, or serve as a platform for any of the intravesical devices described herein.

As discussed previously, an implant can be at least partially expandable. Expansion facilitates delivery by allowing the implant to assume a first delivery profile for passage through the urethra or surgical opening in the bladder and to assume a second expanded profile operable to prevent the implant from entering the trigone region. In some embodiments, the expanded implant can be characterized by one or more dimensions greater than the smallest cross-section distance of the trigone region.

Delivery

One aspect of the disclosure relates to the delivery of an implant. Various instruments and implants are provided herein for the implantation of medical devices within the bladder via the urethra, open surgery or percutaneously through the abdomen, back, vagina, bowel, or perineum. In certain embodiments, the implantable medical device may comprise one or more expandable membrane enclosure or balloon, sponge, attenuator, space occupying member, drug delivery device, data collection device, nerve stimulation device, wave producing device, vibration producing device, pressure sensing device, chemical sensing device, volume sensing device, or a therapeutic device. From this disclosure it will be appreciated that although the examples provided deal primarily with delivery of an implant into the bladder, the methods and devices herein can be used to provide treatment at sites in other areas of the body as well. For example, devices can be placed within or proximal to other organs and sites in the body such as the heart, lung, cranium, cardiovascular system, breasts, abdominal area or cavity, eye, testicles, intestines, stomach, etc.

Figure 6:
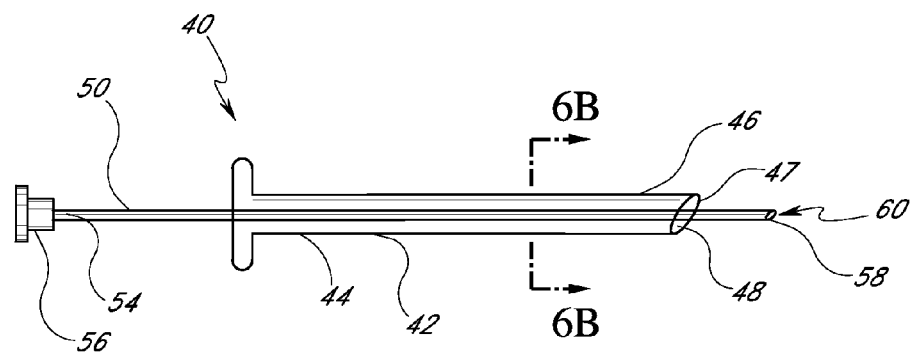
FIG. 6 is a side elevational schematic view of a delivery system for deploying an implant.

Referring to FIG. 6, there is illustrated one delivery system for deploying an implant, such as, an attenuation device, into a treatment site, such as, for example, the bladder. In general, the delivery system 40 is configured to advance the implant 66 (not illustrated) transurethrally into the bladder while in a first, reduced cross-sectional configuration, and to thereafter inflate or enlarge or permit the expansion of the implant to a second, implanted orientation. The particular configuration and functionality of the delivery system 40 will therefore be governed in large part by the particular design of the implant 66. Thus, as will be apparent to those of skill in the art in view of the disclosure herein, various modifications and adaptations may become desirable to the particular delivery system disclosed herein, depending upon the construction of the corresponding implant.

The delivery system 40 comprises an elongate tubular body 42 having a proximal end 44 and a distal end 46. Tubular body 42 is dimensioned to transurethrally access the bladder. Thus, the tubular body 42 preferably has an outside diameter of no more than about 8 mm, and, preferably, no more than about 3-6 mm. The length of the tubular body 42 may be varied, depending upon the desired proximal extension of the delivery system 42 from the urethra during deployment. In general, an axial length of tubular body 42 within the range of from about 1" to about 10" for adult female patients and from about 4" to about 30" for adult male patients is currently contemplated.

The tubular body 42 is provided with at least one central lumen 48 extending axially therethrough. Central lumen 48 axially slideably receives a filling tube 50, for filling the attenuation device 66. Filling tube 50 is a tubular body 52 having a proximal end 54 and a distal end 58. An inflation lumen 60 extends throughout the length of the tubular body 52, and is in fluid communication with a proximal hub 56. Hub 56 comprises a connector such as a standard luer connector for coupling to a source of inflation media.

The tubular body 52 has an axial length which is sufficiently longer than the axial length of tubular body 42 to allow the proximal hub 56 to remain accessible to the clinician and accomplish the functions of deploying and filling the implant 66. In one embodiment, an outer tubular sheath (not illustrated) is slideably carried over the tubular body 42, and is spaced radially apart from the tubular body 52 to define an annular cavity for receiving a rolled attenuation device 66 therein. In this manner, the deflated implant 66 can be rolled around a distal portion of the tubular body 52 and carried within the tubular sheath during transurethral placement. Once the delivery system 40 has been properly positioned, proximal retraction of the outer sheath with respect to the tubular body 52 exposes the deflated implant 66. A source of inflation media is coupled to the proximal hub 56, and media is introduced distally through central lumen 60 to inflate the implant 66. Following inflation of the implant 66, the delivery system 40 is disengaged from the implant 66, such as by retracting the filling tube 50 with respect to the tubular body 42. A distal stop surface 47 on tubular body 42 prevents proximal movement of the implant 66 as the filling tube 50 is proximally retracted. Delivery system 40 is thereafter removed from the patient, leaving the inflated implant 66 within the bladder.

Figure 6A:
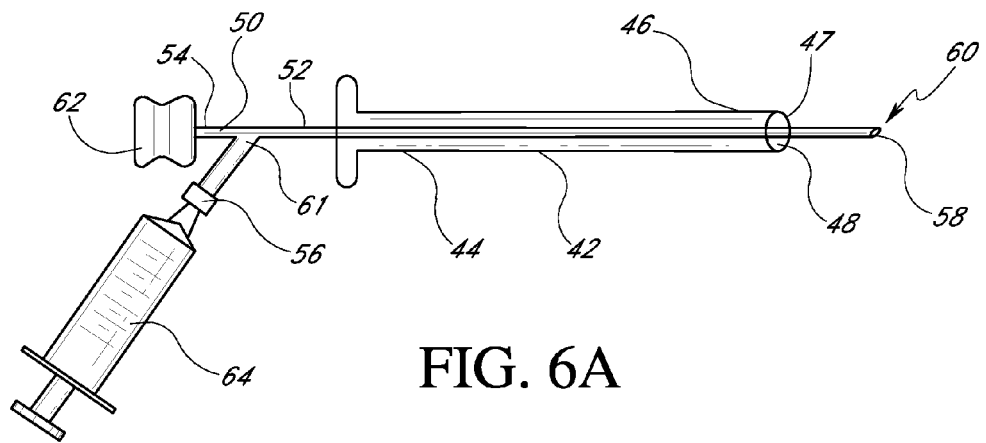
FIG. 6A is a side elevational schematic view of another delivery system.
Figure 6B:
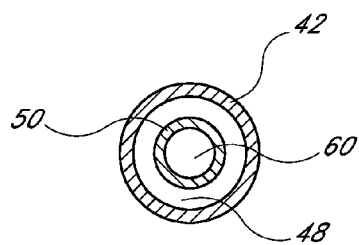
FIG. 6B is a cross-section through the line 6B-6B in FIG. 6.

With reference to FIGS. 6A and 6B, there is illustrated a modified version of the delivery system 40. In this embodiment, a control 62 is placed at the proximal end 54 of the tubular body 52. The control 62 may be in any of a variety of forms, such as a handle, knob or pistol grip. The control 62 may be grasped by the clinician, and utilized to axially advance or retract the filling tube 50 within the tubular body 42. The proximal hub 56 is connected to the tubular body 52 by way of a bifurcation 61. As will be appreciated by those of skill in the art, the central lumen 60 extends from the proximal hub 56 to the distal end 58. An inflation source 64 such as a syringe filled with a predetermined volume of a gas, liquid or other media may be connected to the proximal hub 56.

For patient comfort, the introducer is suitably sized to easily pass through the urethra (approximately 1 to 8 mm diameter). Visual feedback is provided to the clinician by means of insertion depth indicators along the longitudinal length of the introducer. The introducer may also have a fixed or adjustable depth stop that allows the clinician to pre-set the desired insertion depth. One can also determine whether the introducer has reached the bladder via urine reflux through the introducer, visually via intraoperative imaging, or via inflating a distal locator balloon after the introducer has been inserted a selected distance and pulling back on the introducer until the balloon resists further backward travel through the bladder neck. The distal locator balloon can be carried within or along the introducer and inflated via a separate lumen.

Locator balloon, buckling or accordion-like expandable systems can be used as part of any delivery systems described herein. Once the delivery system has been inserted into the urethra to the desired depth the introducer is then kept in a fixed position and the attenuation device mounted on the distal end of the fill tube is then extended in the lumen of the bladder. The attenuation device is then filled with the indicated volume of media from the attached syringe or similar device. Once properly inflated, the attenuation device is released from the fill tube using the tip of the introducer as an opposing force disengaging the attenuation device valve from the fill tube. The fill tube is then retracted completely into the lumen of the introducer and the entire delivery system is then withdrawn from the patient. The attenuation device is left in place for the clinically indicated period of time.

One aspect of the present disclosure relates to the delivery of a very flexible, thin walled device. Delivery of an attenuation device is typically accomplished via a suitably sized introducer or possibly through the working channel of an endoscope or cystoscope. However, in certain instances the columnar strength of an attenuation device may make it difficult to be pushed through such channels. In many situations it will be desired that the delivery system be atraumatic, and not pose a threat of tissue damage.

To facilitate the deployment of the implant, it may be desirable to compact the implant to fit into a cannulated device or transurethral sheath. This can be done by folding, compressing, rolling, etc. For example, folding the implant can shorten the effective length of the delivery system and compress the implant along one or more axis. As the implant is filled, it can unfold and assume its intended dimensions. Also, the folds can preferably be oriented such that the initially opening side or flap opens upward away from the trigone or is oriented to open in the direction of the dome.

In one example, the implant 66 is folded in half and then in half again. Thus the implant is one quarter of the original size. The folded implant can then be pulled, pushed, rolled, surrounded and/or otherwise placed within and/or connected to a delivery system.

The implant is normally folded on itself along its diameter in order to present a low profile for insertion into, for example, a patient's bladder transurethrally. The implant can be wound, rolled-up, compressed, or otherwise folded, all in one or more directions, to decrease the size of the implant for the delivery procedure. Following insertion the implant can be inflated via an inflation tube to which it is pre-mounted. After inflating the inflation tube is detached and the implant is freed.

With reference to the embodiment illustrated in FIGS. 7A and 7B, a delivery system 40 for delivering an implant 66 into the bladder is shown. The implant 66 can be an attenuation device to attenuate pressure waves in the bladder. The delivery system 40 shown comprises an attenuation device containment tube 386, an inflation tube 382 and an atraumatic tip 378. The attenuation device containment tube 386 is a simple open-ended cylinder. The attenuation device 66 is folded as described previously and inserted into the containment tube 386. An open end of the containment tube 386 would present a potentially traumatic edge to the urethra. In order to prevent such trauma, the open end of the containment tube 386 in this instance has a rounded atraumatic tip 378. This tip 378 contains slits 388 which, on sliding the inflation tube 382 and attenuation device 380 forward allows the tip 378 to open and deploys the attenuation device 66 from the containment tube 386 into the bladder.

In use the distal end of the delivery system 40 is inserted through the urethra to an appropriate depth. The attenuation device 66 is advanced using the inflation tube 382 and releases easily from the containment tube 386. The attenuation device 66 is inflated, released from the inflation tube, and floats freely in the bladder. Guidance using ultrasound or other imaging modality or position feedback system can also be employed to help guide the delivery system into the bladder.

In one embodiment, a removable delivery system is used to deliver, deploy, and fill an attenuation device. The delivery system can take the form of the system taught by U.S. Pat. No. 5,479,945, titled "Method and a Removable Device which can be Used for the Self-Administered Treatment of Urinary Tract Infections or Other Disorders," issued Jan. 2, 1996, the disclosure of which is incorporated in its entirety herein by reference.

Figure 8A:
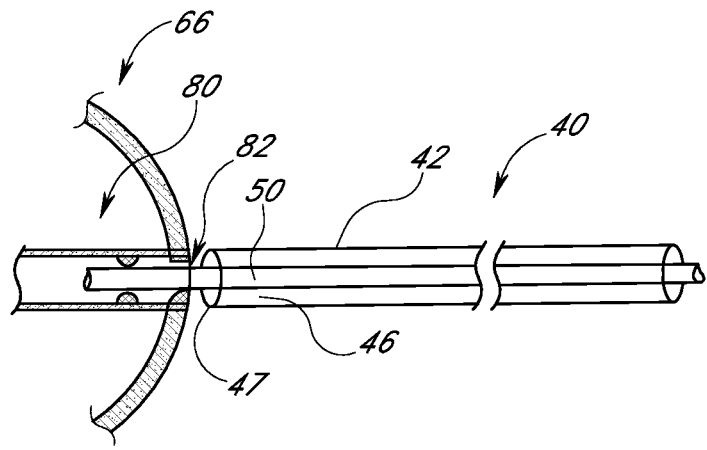
FIG. 8A is a detail schematic view of the filling tube of a delivery system engaged within the valve of an implant.
Figure 8B:
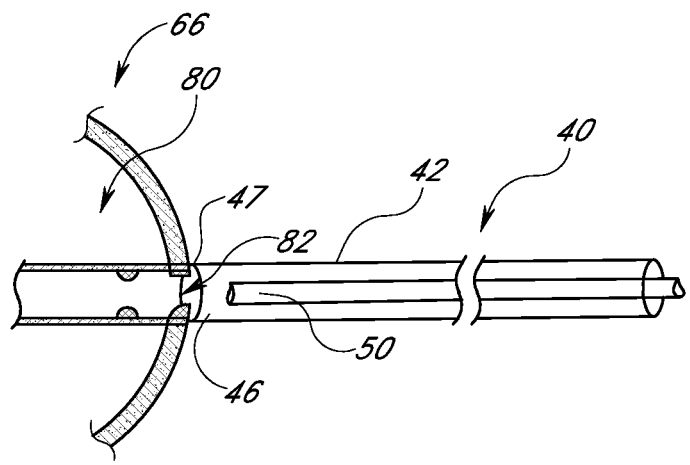
FIG. 8B is a detail schematic view as in FIG. 7A, with the filling tube proximally retracted from the valve.

With reference to FIGS. 8A and 8B, there is illustrated one disengagement sequence for deploying an inflatable attenuation device 66 from a delivery system 40. As illustrated in FIG. 8A, the delivery system 40 is initially configured with the filling tube 50 positioned within the valve 80. The distal end 46 of outer tubular body 42 is dimensioned such that it will not fit through the aperture 82 of valve 80. Once the attenuation device 66 has been positioned within the bladder, the attenuation device 66 is inflated through filling tube 50.

With reference to FIG. 8B, the filling tube 50 is proximally retracted following inflation so that it disengages from the valve 80. This is accomplished by obstructing proximal movement of the attenuation device 66 by stop surface 47 on the distal end 46 of tubular body 42. The attenuation device 66 is thereafter fully disengaged from the delivery system 40, and the delivery system 40 may be removed.

Figure 9:
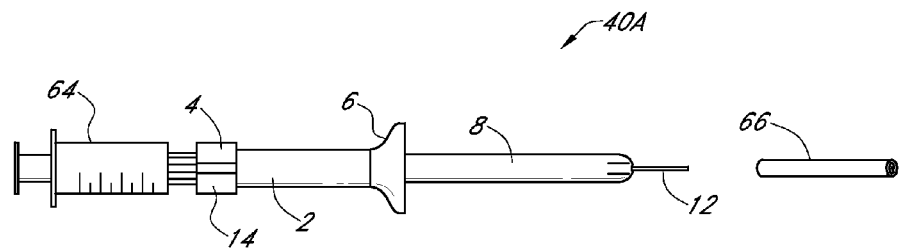
FIG. 9 is a side view of another embodiment of a delivery system.

FIG. 9 presents another embodiment of a delivery system 40A. The delivery system 40A can be used with many different types of implants 66, including an attenuation device. As shown, the attenuation device 66 has been rolled in preparation for delivery. The attenuation device 66 can also be prepared in other ways as discussed above, such as being be wound, rolled-up, compressed, or otherwise folded, all in one or more directions, to decrease the size of the implant for the delivery procedure. The attenuation device 66 in a preferred embodiment is a spherical balloon with a one-way valve.

Figure 9A:
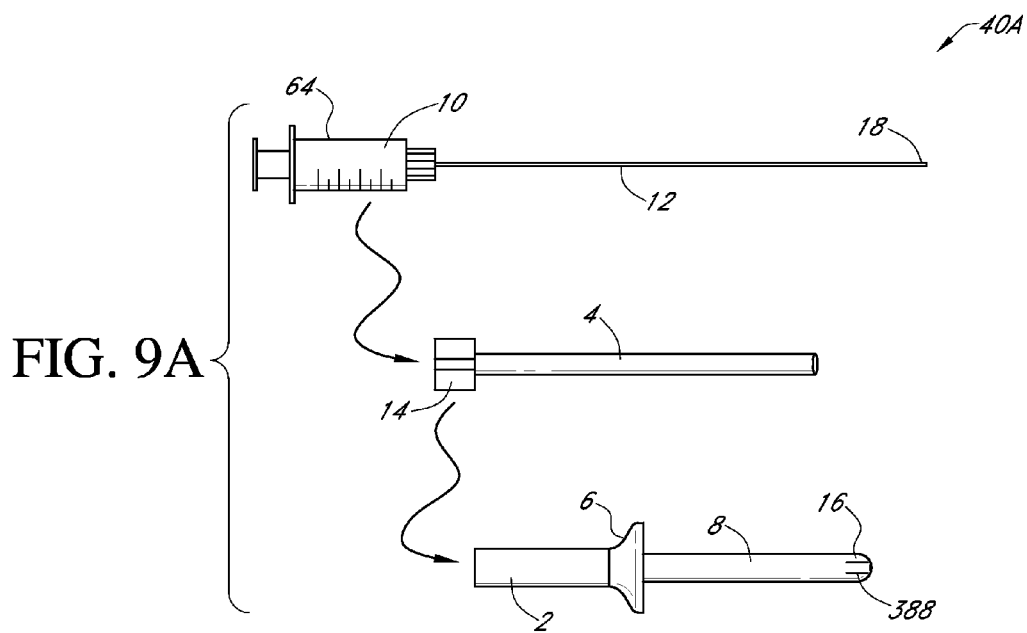
FIG. 9A is a side view of the delivery system of FIG. 9 showing separable components thereof.

The delivery instrument or system 40A, shown in FIGS. 9 and 9A comprises a guide body 2, syringe 64, implant decoupler or advancer 4, meatal stop surface 6 and transurethral body 8. The syringe or other suitable inflation or injection mechanism 64 may comprise a barrel 10 and a needle or conduit 12. The needle 12 can be connected to the barrel 10 by a luer connection or other connection mechanism known in the art. The needle 12 can be slidably inserted within or along an implant advancer or decoupler 4. The implant 66 can then be connected to the needle 12. In use, the decoupler 4 disengages the implant 66 from the needle 12. Both the needle 12 and decoupler 4 may be slidably carried by or within the guide body 2. When connected to the guide body 2, the decoupler 4 has an exposed portion 14. The guide body 2 further comprises an adjustable or fixed meatal stop surface 6 and a hollow transurethral body 8 terminating in a tip 16. The tip 16 can be an atraumatic tip. The tip 16 can also have slits or perforations 388.

In one embodiment, the implant decoupler 4 is a feature within or along the transurethral body 8 that prevents an implant 66 from being retracted into the instrument or move in a direction other than distally away from the delivery instrument 40A. In another embodiment, the decoupler 4 is advanceable and advances the implant 66 out of, or relative to, the transurethral body 8 and/or needle 12. The needle 12 terminates in a tip 18. The implant 66 can be coupled to the needle tip 18 via an engagement mechanism. The engagement mechanism can comprise a valve, such as the valves shown in FIGS. 5-5A, which can be mated to the needle tip 18. At least a portion of the implant 66 may be carried within or alongside of the transurethral body 8.

The delivery system 40 can impart columnar strength to the implant 66. In some embodiments, for example where the implant is a flexible body, increased columnar strength can be desirable to facilitate delivery of the implant in to the body. In some embodiments, the transurethral body 8 can impart columnar strength to the implant 66. In certain embodiments, the implant 66 is compressed or folded along one or more axis. In some embodiments, the implant 66 is wound, wrapped, coiled, spun, twisted, or spiraled within the transurethral body 8 and/or about the needle 12 or advancer 4 to impart columnar strength allowing it to be expelled out of or relative to the transurethral body 8.

In FIGS. 10A-G and 11A-C, other examples of portions of transurethral bodies 8 of various delivery instruments 40 are provided. In FIG. 10A, a transurethral body 8 comprises a tubular, cylindrical, hollow or cannulated member with a lateral opening, window or port 20 and a curved, rounded, or blunt distal tip 16. The opening 20 can be oval (FIG. 10A), circular, rectangular, slit-like (FIG. 10B), oblong (FIG. 10C), teardrop shaped, biased and can further comprise a flap, door or retractable cover 22 (FIG. 10D).

In some embodiments (not shown), the transurethral body 8 is formed as a wrap covering the implant 66. The wrap can be shrunk around the implant 66, wound around the implant 66, or the wrap can be applied as a coating. In some embodiments, the implant 66 is the transurethral body 8, in this embodiment the implant 66 can be compressed to create a small profile and be comprised of a lubricious material to facilitate transurethral or percutaneous travel.

The tip curve can be biased (FIG. 10E) or symmetrical (FIG. 10A). At least a portion of the transurethral body 8 itself and instrument elements carried within or along it can be rigid, flexible, curved or have multiple curves to facilitate placement within and beyond the urethra to deliver to different sites within the bladder such as the back wall, dome, rugae of mucosa tissue, trigonal area, ureteral openings, internal or external urethral openings, and internal or external urethral sphincters. Also shown are transurethral body members 8 having oblong windows 20 providing for the preferential or biased opening or expansion of an implant 66. In one embodiment, the opening 20 biases the distal expansion of a balloon implant 66 such that the implant 66 is delivered laterally and distally at the same time.

In another embodiment, a portion of the transurethral body 8 and/or decoupler 4 is comprised of a shape memory material that when heated by the human body after insertion assumes a second shape, such as, bent or curved. The transurethral body 8 and/or decoupler 4 can also be operable to deliver the implant 66 within the upper or domed section of the bladder or deflect off of the back wall of the bladder.

As shown in FIGS. 11A-C, a transurethral body 8 can have double or multiple openings 20. Shown are two openings 20 at a distal portion of the transurethral body 8 and an optional connector passage 26 for a coupled implant. The implants 66D shown are two balloons coupled by a connector 24 forming the shape of a dumbbell. The connector 24 may simply be an extension of the balloon membrane, suture, or a fluid or gas conduit.

Figure 12A:
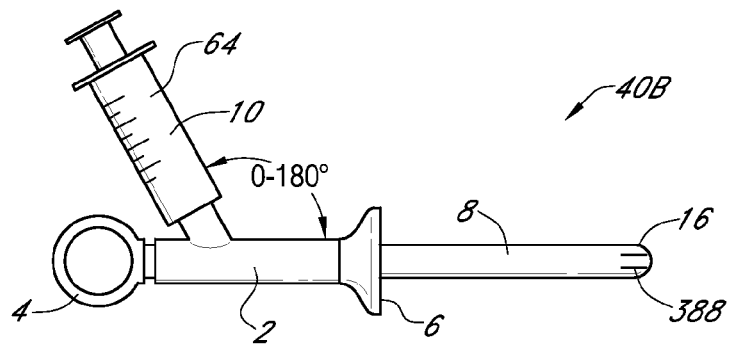
FIG. 12A is a side view of an embodiment of a delivery system with an angularly offset syringe.
Figure 12B:
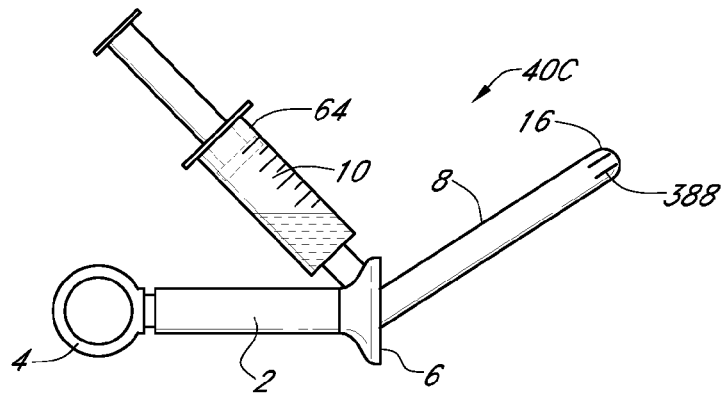
FIG. 12B is a side view of an embodiment of a delivery system with an angularly offset syringe and transurethral body.
Figure 12C:
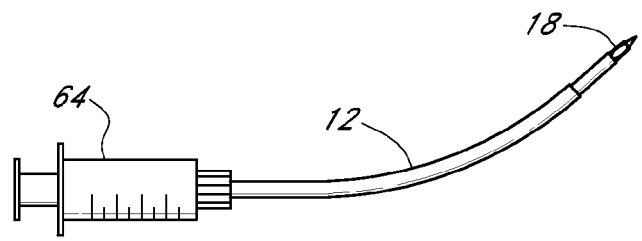
FIG. 12C is a side view of part of an embodiment of a delivery system with a syringe having a flexible conduit and a rigid tip.

Turning to FIGS. 12A-C, various syringe 64 and transurethral body 8 elements are presented oriented in different positions relative to the guide body 2 of the delivery instruments 40B, 40C. Angling the syringe 64 offset to the guide body 2 may be advantageous to provide for a more vertical syringe barrel 10 orientation during delivery.

For example, in some embodiments it is desired to inject a media having a gas component and a liquid component into the implant 66. The liquid component can be very small compared to the gas component. In some embodiments, the media can comprise 0.5 cc liquid PFC and 25 cc of air. In the orientations shown, the liquid portion will tend to reside proximate the needle or conduit 12 and be delivered first into the implant and then followed by the air or other gas component remaining in the barrel. This feature can be critical when delivering small amounts of liquid relative to the volume of gas.

In the embodiment of FIG. 12C, the barrel of the syringe is coupled to a flexible conduit 12 terminating in a tip or implant coupling mechanism 18 which may be flexible or rigid. In some embodiments, the syringe and flexible conduit is used in the configurations of FIGS. 12A and B.

Figure 13:
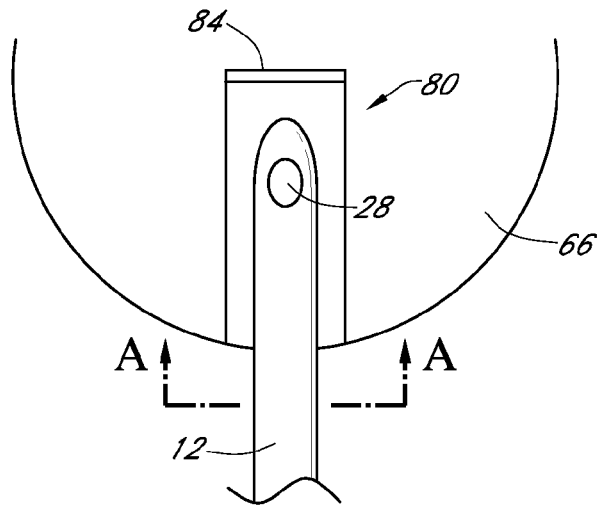
FIG. 13 is a schematic representation of a delivery system needle or conduit tip within a valve of an inflatable implant.
Figure 13E:
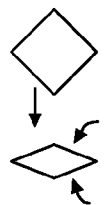
Figure 14A:
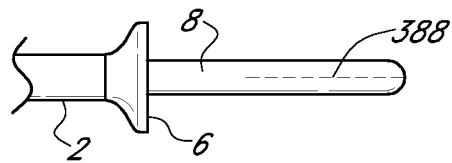
FIGS. 14A-C are side views of different embodiments of transurethral bodies of a delivery system.
Figure 14B:
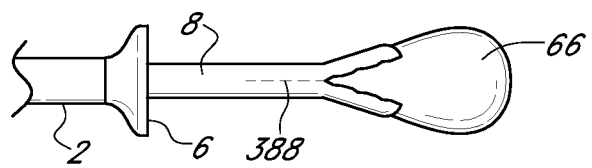

Various tip or implant coupling mechanism 18 profiles are presented in FIGS. 13-13E. The tips can be mated with corresponding female portions of implant valves. FIG. 13 shows the needle 12 in the valve 80 of the implant 66. An opening 28 in the needle tip is also shown. FIGS. 13A-E are taken along line A-A to show the cross-section of the needle 12. As can be seen, the cross-section can be any of many shapes, including, circular, flat, oval, rectangular, rounded rectangular, and other polygons. In some embodiments, the needle tip can assume a first shape and a second shape such as that shown in FIG. 13E. The first shape can be used when inflating the implant 66 and needle tip can assume the second shape after inflation or upon sealing of the valve 80. The needle 12 tip can further comprise a raised rib or coupler mated to the balloon to prevent backflow during inflation or a groove or recess operable to accept an adhesive, polymer, or flexible material such as silicone to form a compliant fit with the balloon Turning now to FIGS. 14A and B, an embodiment of transurethral body 8 and distal tip 16 is shown. Implants 66 may be advanced out of or through the transurethral body 8 at various points along its long axis or distal end. In some embodiments the tip 16 is open, perforated, pointed, blunt, and/or rounded. One or more perforation, slit, window, door, flap, port, and may be positioned along the transurethral body 8 to facilitate the expulsion or expansion of the implant 66 within or carried by the transurethral body 8. In various embodiments the implant 66 is expelled from the transurethral body 8; in other embodiments the implant 66 expands and breaks or parts the perforations 388 along the transurethral body 8 or expands a slit 388 or elastic opening.

Figure 14C:
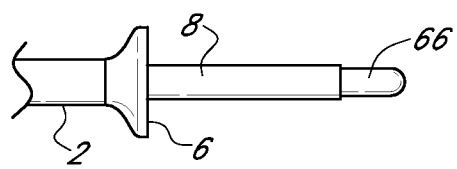

In FIG. 14C, a transurethral body 8 is shown wherein the implant 66 is at least partly exposed to form a tip. As explained previously, the implant 66 can be compressed or wound and may be coated, lubricated or built up with a biodegradable substance to ease insertion into the bladder.

Figure 15A:
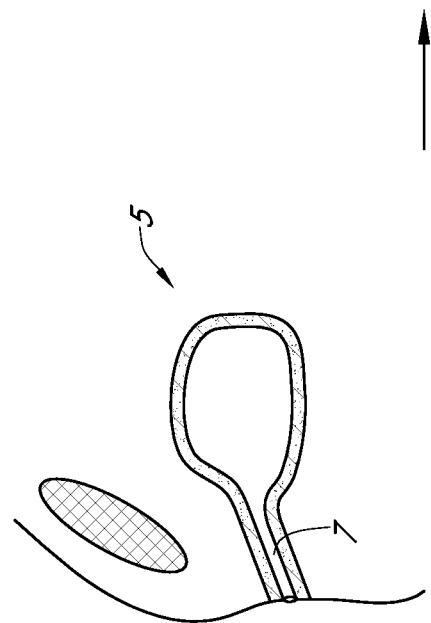
FIGS. 15A and B are representations of the shape of the bladder with different levels of fluid and relating to part of a delivery method.
Figure 15B:
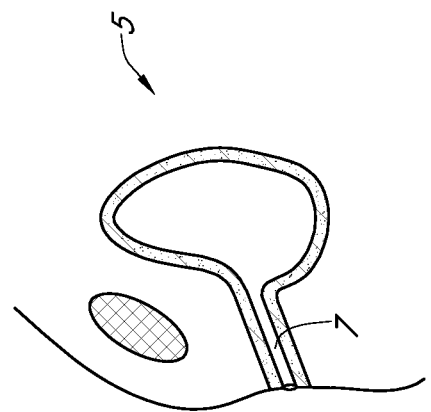

With reference to FIGS. 15A-18C, various steps of a delivery sequence are shown, including optional steps to improve the outcome of the delivery. As an initial step, the amount of fluid in the bladder may be determined. This may be done, for example, cystoscopically, via imaging, or via a catheter. In FIG. 15A, a relatively empty bladder 5 is shown. Preferably, there will be at least 100-500 cc of fluid present within the bladder 5 for implantation. In some embodiments, there will be a minimum of 200 cc of fluid in the bladder 5. According to some embodiments, liquid or gas is added to the bladder 5 to ensure that at least 100-500 cc of liquid and/or gas is present within the bladder 5 during implantation (FIG. 15B).

Optionally, a cystoscope or probe can then used to determine the length of the urethra 7 and/or the distance from the internal urethral opening to the back wall of the bladder. The adjustable meatal stop surface 6 of the guide body 2 is adjusted such that the transurethral body 8 will extend beyond the inner urethral opening to a select depth. Alternatively, a device having a fixed meatal stop feature may be appropriately selected from among multiple sized devices based on the patient's anatomy.

A delivery system 40, such as those depicted in FIGS. 9-14, may be used in the delivery procedure. The delivery system 40 may optionally comprise a syringe 64 containing a gas such as air and a small amount of liquid perfluorocarbon (PFC) or other liquid with a high vapor pressure and/or therapeutic agent. The use of an implant with PFCs and/or other liquids with a high vapor pressure is explained in more detail below.

Figure 16B:
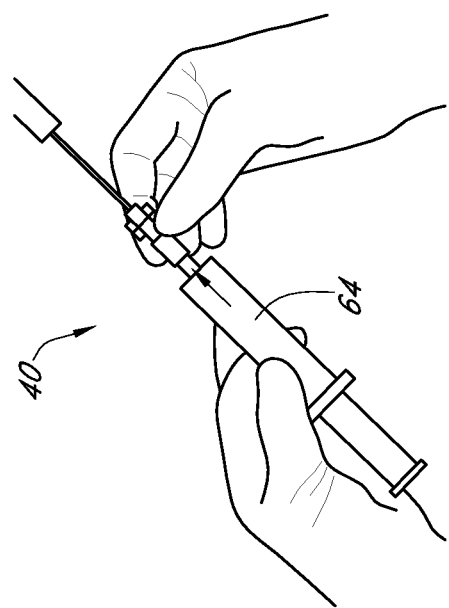
FIGS. 16A and B show certain method steps for preparing a delivery system to deliver an implant.
Figure 16A:
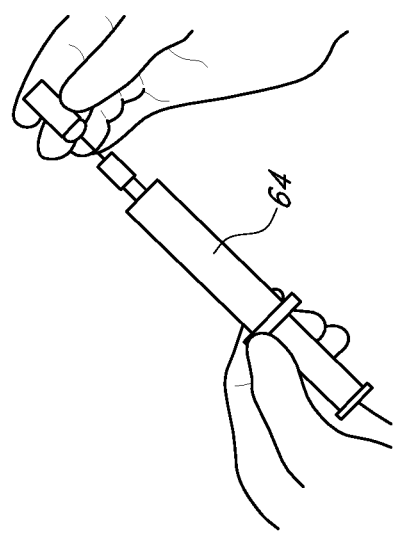

The delivery system 40 can be prepared by filling the syringe 64 with the desired amount of fluid and/or gas (FIG. 16A). In some embodiments, the syringe can be filled with a certain amount of liquid PFC and a certain amount of air. In some embodiments, the amount of air can comprise about 1-100 cc. In some embodiments, the amount of air can comprise about 15-25 cc. In some embodiments the amount of fluid PFC can comprise about 0.1-2 cc. In some embodiments, the amount of fluid PFC can comprise about 0.5-1 cc.

After the syringe is prepared, it can be connected to or inserted into the rest of the delivery system 40 (FIG. 16B). In some embodiments, such as that shown in FIG. 9, the delivery system 40 and implant 66 can be prepackaged and assembled. The syringe 64 can be disconnected so that it may more easily be filled. The filled syringe 64 can then be connected to the needle or conduit 12 via a luer connection in preparation for implantation of the implant 66.

Figure 17A:
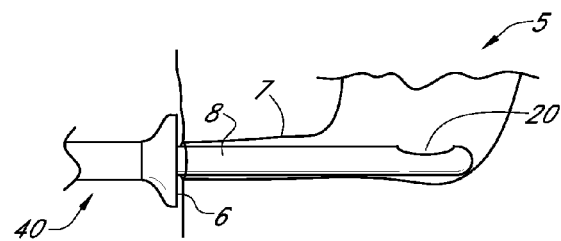
FIGS. 17A-D are side views of different embodiments of transurethral bodies of a delivery system within the bladder and urethra.
Figures 17B, 17C:
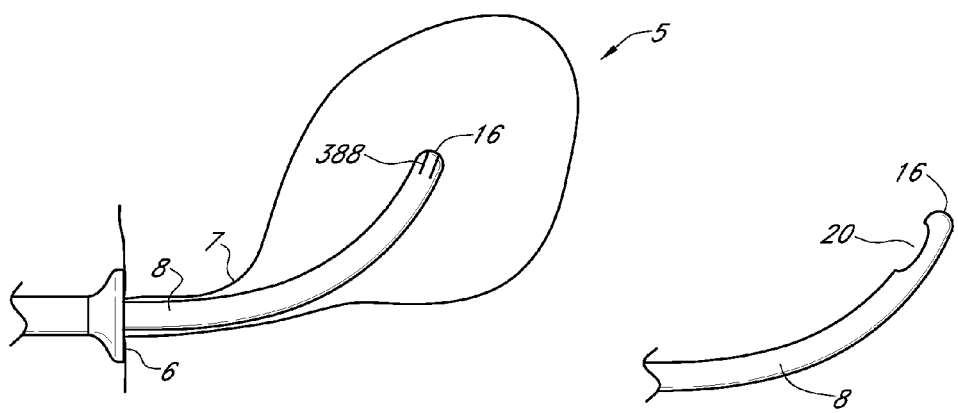

As shown in FIG. 17A, the transurethral body 8 is then inserted into the urethra. In some embodiments, the meatal stop 6 will abut the meatus to determine how far the transurethral body 8 will advance into the bladder 5. In other embodiments, such as delivery systems 40 without a meatal stop 6, the physician may use markings on the side of the device or other devices to determine how far to advance the transurethral body 8. The tip 16 of the transurethral body 8 can be deflected off of the back wall of the bladder (FIG. 17A) or the length of the transurethral body 8 can be dimensioned such that the tip 16 is incapable of reaching the wall. Alternatively the transurethral body 8 can be curved (FIG. 17B-C), bent, biased, flexible, articulable or comprised of a shape memory material such that upon full insertion the distal end extends upward toward or within the dome of the bladder.

Once the desired implant location is reached, some embodiments of delivery system 40 may optionally be oriented such that the distal tip 16 or opening 20 is in a desired direction or position relative to the bladder to release and inflate the implant 66. This may include rotating or tilting the device 40. For example, with an opening 20, shown in FIG. 17C, the implant can be delivered in a way that is away from the back wall of the bladder or from tissue in the dome area.

Figure 17D:
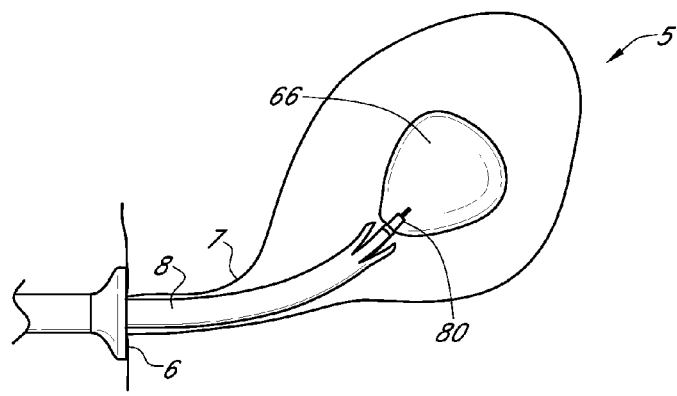
Figure 18B:
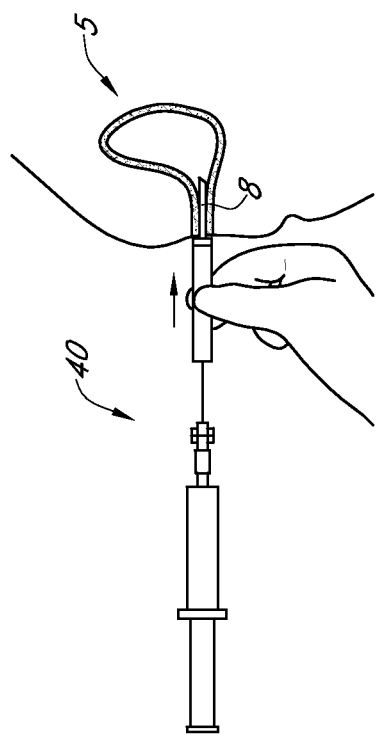
FIGS. 18A-D show method steps for inserting an implant according to one embodiment.
Figure 18A:
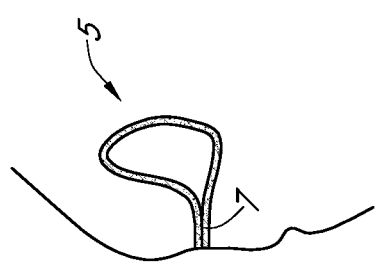
Figure 18C:
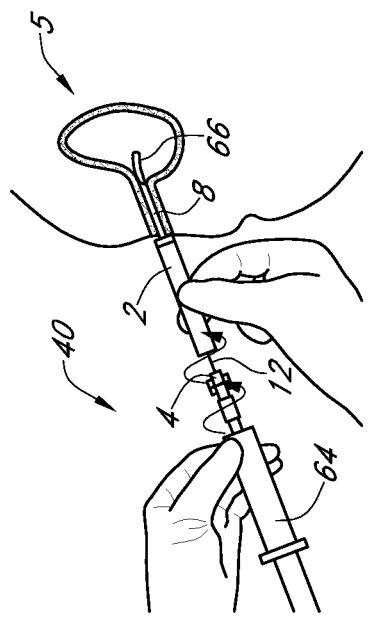
Figure 18D:
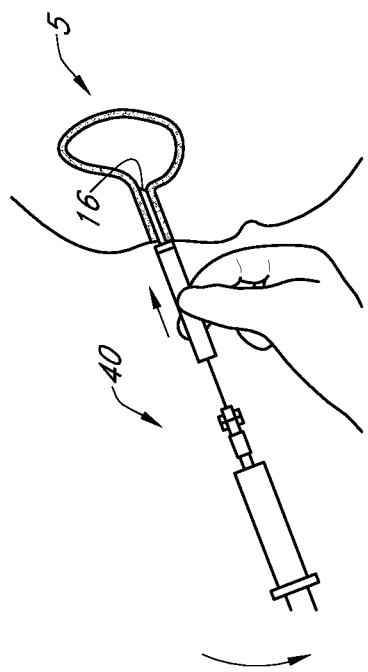
Figure 18F:
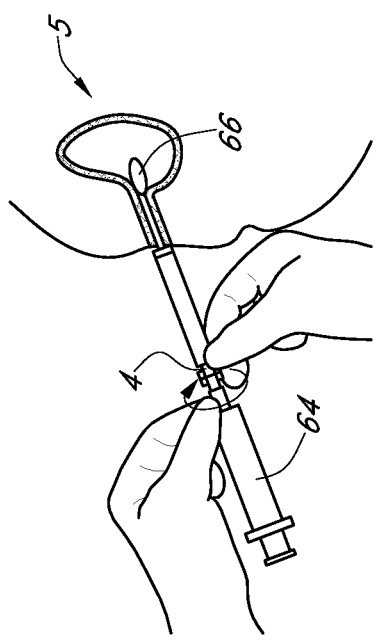
FIGS. 18F-H illustrate methods of releasing an implant from a delivery system.
Figure 18E:
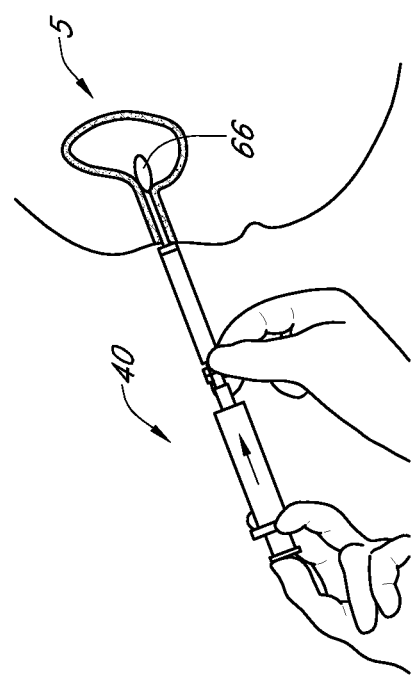
FIG. 18E illustrates a method step of inflating an implant.
Figure 18H:
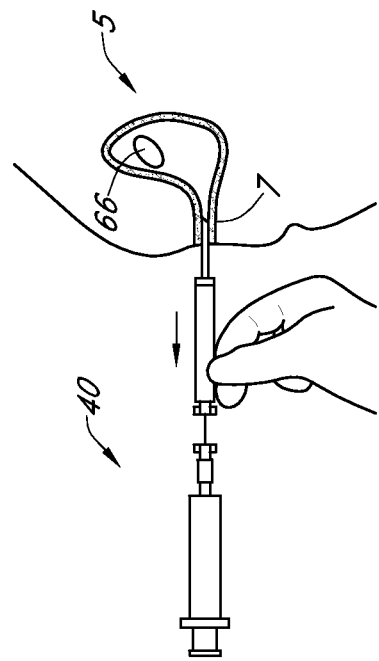
Figure 18G:
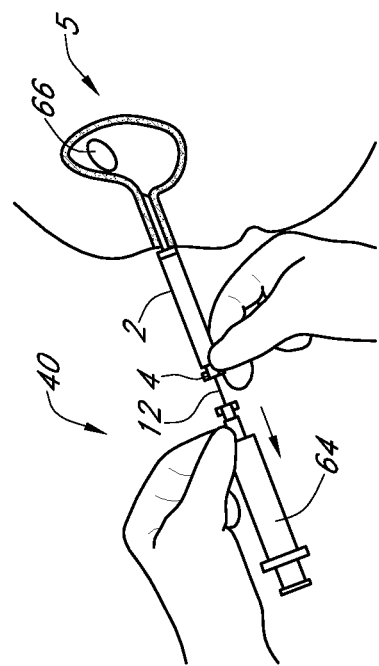

Once in the proper position and/or orientation, the implant 66 can be advanced into the bladder 5. This can be done in many different ways as will be shown. In some embodiments, such as with the delivery device 40 of FIG. 9, the advancer 4, syringe 64, needle or conduit 12 and implant 66 can be advanced within the guide body 2 and transurethral body 8. This advancement can break or opening the slits or perforations 388 on the tip to allow the implant 66 to exit the delivery instrument 40 (FIG. 17D). In some embodiments, the implant 66 can exit the tip 16 through an opening 20. The plunger of the syringe 64 is then depressed, to deliver the media, such as fluid and gas, into the inflatable device 66. The conduit or needle 12 is then retracted, thereby disengaging and releasing the implant 66 into the bladder. The valve 80 of the implant 66 in which the needle 12 had been inserted also closes and retains the media within the implant enclosure.

In some embodiments, the implant 66 may or may not be advanced. Inflating the implant 66 can cause the implant 66 to expand and can force the implant to exit the transurethral body 8. In this way, the inflatable device or implant 66 can exit the window 20 or slit 388 in the tip 16. Also the perforations 388 can be forced open along the transurethral body 8 by expanding the implant 66.

In some embodiments, inflating the implant 66 causes the implant to separate from the delivery instrument 40. In some embodiments, relative movement of the advancer 4 and needle or conduit 12 (either moving forward or backward relative to the other) causes the implant 66 to disengage and the implant valve 80 closes. Once the implant has been released, the delivery instrument 40 can be withdrawn from the bladder and the urethra.

In certain embodiments, the implant 66 can be dislodged from the delivery instrument 40 by relative motion of needle or conduit 12 to which the implant 66 is attached and the advancer 4 encompassing the needle 12 in a shearing motion.

In another embodiment, the implant 66 can be deployed as a long, straight tube which coils as it leaves the deployment sheath due to a pre-set pattern, set in either the shell of the implant or a stiffening member with shape memory.

In another embodiment, in which the inflation media is comprised of a liquid-gas mixture, a pre-loaded syringe 64 or forward filling of the needle or conduit 12 is provided. The liquid portion can be pushed through the gas portion of the mixture. Also, the liquid can be kept in the open flow path with the use of a flexible adapter or valve that prevents the liquid from falling out of the conduit 12 if the syringe 64 is removed to fill with gas in a two step sequence.

In yet another embodiment, a flexible implant 66 is compressed, accordion-style and is operable to spring forward during deployment, inflation of the implant 66, or release of a compressing member.

In a further embodiment, an implant 66 is deployed and partially inflated with a small portion of liquid. In this embodiment, the liquid has the ability to create a negative vapor pressure gradient which would, over time, force gas from the external liquid environment into the implant 66, thus inflating it.

With reference to FIGS. 18A-H, one particular non limiting delivery method will be explained. Other embodiments can comprise one or more of the steps outlined below. Each step A-H refers to the corresponding FIG. 18A-H. In step A, the bladder is checked to ensure that a minimum of 200 cc of fluid is in the bladder 5. Additional fluid is added if necessary. Air and water are examples of the fluid. Other embodiments can include different amounts of fluid. In step B, the transurethral body 8 is lubricated and inserted into the urethra 7. In step C, the deliver system 40 is tilted down such that the tip 16 is pointed upwards at the dome of the bladder. In step D, the advancer 4, syringe 64, implant 66 and needle 12 are advanced while rotating clockwise and the guide body 2 and transurethral body 8 are maintained in a stationary position. This inserts the implant 66 into the bladder 5.

In step E, media is injected into the implant 66, expanding the implant 66. In this embodiment, the media includes an amount of liquid PFC and about 15 cc of air. In step F, the advancer 4 is disconnected from the syringe 64 and needle or conduit 12. In this embodiment, the advancer 4 is connected to the syringe via a luer connection, thus rotating the syringe 64 while holding the advancer 4 stationary can disconnect the luer connection. In step G, the advancer 4 and guide body 2 are held stationary while the syringe 64 and needle or conduit 12 are retracted. Here they are retracted about one inch. This releases the implant 66 from the delivery instrument 40 into the bladder 5. Finally, the delivery instrument 40 is removed from the urethra 7 and discarded in step H.

Some delivery methods can include delivering the implant 66 away from the trigonal area. This can include identifying the back wall of the bladder to ensure that the implant 66 is not delivered in the trigone. This can also include expanding or unfolding the implant away from the trigone. This can also include ensuring that a minimum amount of fluid is in the bladder so that a buoyant implant, such as an inflatable implant, will naturally move away from the trigone.

Suitable materials for the guide body 2, transurethral body 8, conduit 12, needle 12, and tip 16 can include: stainless steel, titanium, plastic, nitinol, PEEK, polyimide, polysulphone, fluorinated polymers (PTFE, PFA, FEP, ETFE, PVDF, CTFE), polyethylene (high or low density), polyether block amide, polyester terethalate or elastomers of PET or PBT, ABS, other impact modified styrenics, polycarbonate or copolymers of polycarbonate, braided forms of any of these, reinforced forms of any of these, etc.

Coatings or impregnation agents may also be applied to or integrated into the material above to improve the delivery or treatment outcome. Alternatively such agents can reside in an enclosure or a reservoir and elute out of the device over time. Such agents can include: silver, PET, silicone, active biologic compounds, aqueous hydrogels, butyl rubbers, metal coatings, nano crystallized silver based antimicrobial coating, polyvinylpryrrolidone based coatings, drug coatings including duloxetine hydrochloride, nerotranmitters mediating drugs, analgesics, antiseptics, antibiotics, incontinence treatment drugs, anti-cancer drugs, cystitis treating drug, oxybutynin, anti microbial agent, lubricious agent, anti-incontinence drug, etc.

The diameter of the transurethral body 8 can range from about 2-8 mm or 6-24 french. The length of the transurethral body can range from to 2-8 cm in females and longer for males. The angular offset of the transurethral body 8 relative to the guide body 2 can range from 0 to 180 degrees preferably about 0-30 degrees. The angular offset of the transurethral body relative to the syringe barrel 10 can range from 0-180 degrees preferably 70-110 degrees.

The delivery instrument 40 used for males may optionally have a bent tip to aid in navigating through the urethra as it passes through the prostate. Generally it is desirable to have a more flexible delivery device for men because of the longer urethral length and the fact that the urethra "bends" proximal the prostate. Preferred systems benefit from the ability to "flex" while bending around corners, and resist "kinking." This can be accomplished by a combination of wall thickness and/or having a coiled spring in the wall or a braided structure.

As discussed, an implantable pressure attenuation device can inflate from a first, deflated configuration to a second, at least partially inflated configuration. Various transformable mediums can be used to inflate the housing of the attenuation device from a deflated configuration to at least a partially inflated configuration. In some embodiments, the device is self-inflating.

Removal

The implant 66 is preferably removable from the implanted site, such as the bladder. Removal may be accomplished in any of a variety of ways, depending upon the construction of the implant. Preferably, removal from the bladder is accomplished transurethrally.

Generally, methods of removal from the bladder will include one or more the following steps: identifying the location of the implant 66 within the bladder; engaging the implant; in some embodiments, compromising the integrity of the implant 66 to remain inflated and deflating the implant 66; compressing the implant 66; and removing or allowing the implant 66 to be passed out of the bladder. Alternatively, the implant 66 may be absorbed, dissolved or degraded within or by the bladder or urine.

Figure 19C:
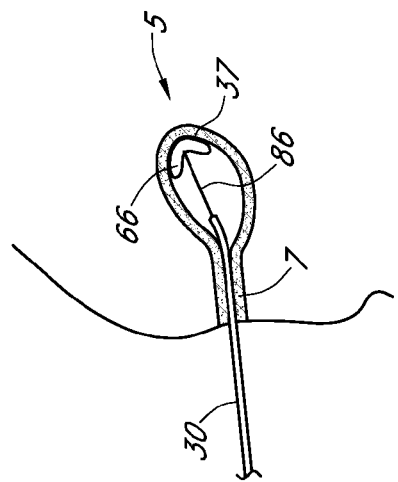
FIGS. 19A-E show methods of removing an implant from the bladder.
Figure 19B:
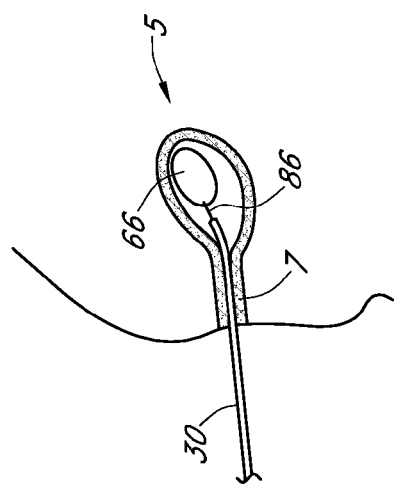
Figure 19A:
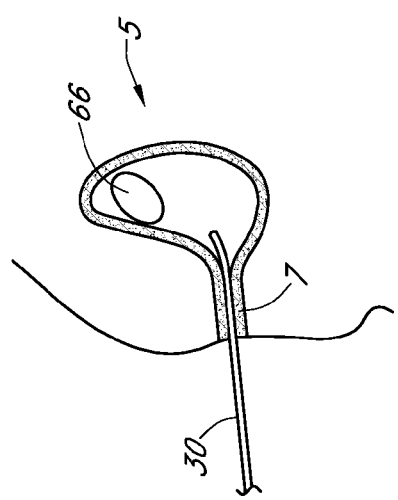
Figure 19D:
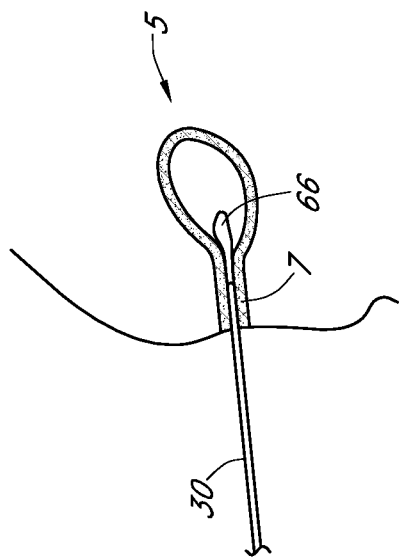
Figure 19E:
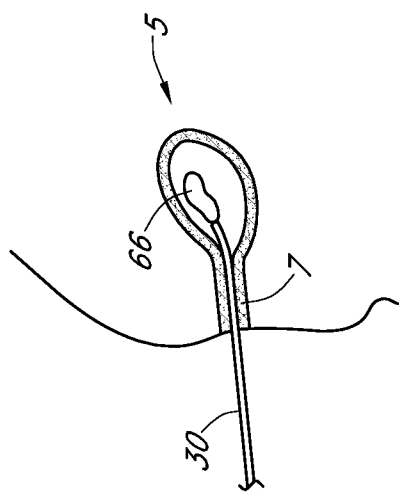

For example, according to some methods the following steps are taken to remove an inflated implant or balloon 66 from the bladder with reference to FIGS. 19A-E. First, a cystoscope is inserted into the bladder. The bladder is drained and the implant is visually located (FIG. 19A). Then a retrieval device, such as any of those described below, is inserted into the cystoscope to engage the balloon 66 (FIG. 19B). The balloon 66 is then deflated by squeezing or compressing the balloon 66 with the retrieval device while pressing the balloon against the wall of the bladder (FIG. 19C). Next, retract the retrieval device and the balloon to the end of the cystoscope (FIG. 19D). Finally, the cystoscope and the balloon are removed together (FIG. 19E).

Various steps and related treatment and retrieval devices will now be discussed.

Locating the Treatment Device

Locating an implant 66, such as an intravesical treatment device within the bladder, can be an active or passive process. For example, the surgeon actively searches for the treatment device 66 visually or blindly, probes around the bladder and receives tactile or other feedback from an instrument. Alternatively, a magnetic element of the implant 66 or a vacuum device can be used to blindly locate the device 66.

A preferred method for inspecting the bladder to locate the implant 66 involves the use of a cystoscope. A cystoscope generally has a working channel for inserting other instruments such as a forceps or grasper. Instead of a cystoscope, a cannula, sheath, or tube may be used. Such an instrument can be fitted with or carry a photo-sensor that can be used to provide visual feedback. For example a sheath can carry optical forceps or a grasper instrument with a distal mounted photo sensor. The photo sensor may be built into the end of the device such as a CMOS or CCD sensor or it may be at the proximal end of the device or separate from the device with the use of a fiber optic pathway.

In one embodiment the implant 66 comprises stripes, dots, geometric shapes, characters or other non-anatomical pigmentation (pink, red, and white) to improve its visibility within the bladder. Further embodiments may comprise surfaces with reflective or shiny elements or infrared, ultraviolet, fluorescent signature colors to facilitate visual recognition by the person removing the device. Alternative embodiments of the implant 66 may optionally include enhancements that may be detected or located with appropriate instrumentation. Such implant enhancements can include an RFID chip or transmitter, radio opaque element, charged surface or portion, selected electrical resistance different than bladder tissue or urine, magnetized surface or portion, or comprise a ferrous material.

Figure 20A:
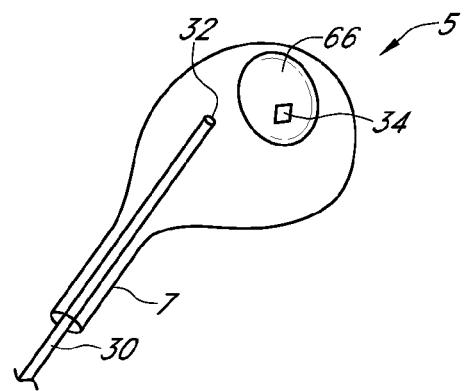
FIGS. 20A-C relate to methods of locating an implant for retrieval, where A uses an optical instrument, B uses suction and in C the implant is tethered to a body structure.

FIG. 20A, illustrates the step of locating an implant 66 with a cystoscope or other cannulated instrument 30. A photo sensor or optical element 32 is shown that can be used to locate the implant 66 within the bladder. The implant 66 can also include an enhancement or distinctive feature 34, as described above which can help the physician to find the implant.

Rather than actively searching for the device to locate it, other methods can be employed to cause the device to migrate to or remain in a selected location. In this way, the implant 66 would necessarily be where the surgeon inserts an instrument. For example, emptying or filling the bladder with liquid and or gas such that the device floats or sinks to a known location. Alternatively, the implant 66 can be compressed proximal to or adjacent the urethra or trigonal region when the bladder is completely voided. Also a tether or anchor could be used.

In another embodiment, the bladder is completely evacuated with a vacuum or suction device. Alternatively, the vacuum device can be used to draw in the implant 66 to the suction device. The tip of some embodiments of a suction device can comprise a cage or filter. The cage can be dome or spherical shaped. The cage can prevent bladder tissue from entering the suction device but permit at least a portion of an intravesical device 66 to enter the suction device. The suction device may optionally include a piercing element such as a needle or heating element to deflate implant.

Figure 20B:
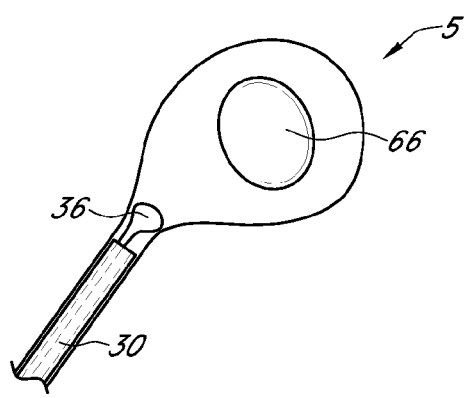

In some embodiments, as shown in FIG. 20B, a vacuum or suction tube 36 is passed through a cystoscope or cannulated device 30. Upon locating the implant 66 the suction tube 30 engages the implant 66 with suction force. When more suction is applied the implant 66 is brought into contact with the tip of the suction tube 36 or cannula 30 causing the implant 66 to tear. The content of the implant 66 is then suctioned followed by the implant 66 which either passes through the suction tube 36 or is engaged by it. The suction tube 36 and implant 66 are then retracted within the cannula 30 out of the urethra.

Figure 20C:
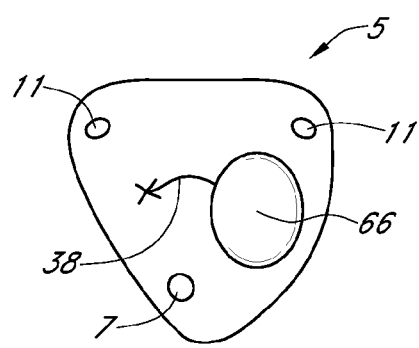

In another embodiment, an implant 66 is anchored or tethered to a selected site along or within the wall of the bladder (FIG. 20C), ureters or urethra. In this instance, the surgeon need only return to the implantation site and retrieve the implant. FIG. 20C further shows a tether or anchor 38 connected to an implant 66 deployed in the bladder just beyond the neck of the bladder in the trigonal region.

In yet another embodiment, the tether 38 can optionally be placed partially within the urethra or extend outside the body beyond the urethra. In yet another embodiment, a tether 38 is retracted within or encapsulated into the wall, surface, or mass of the implant and then released at approximately the desired time of removal to facilitate retrieval of the device. The release of the tether can be timed using a bioabsorbable polymer casing, an electronic timed device, or in response to an external stimulus such as radiofrequency energy, x-rays or other radiation. The tether 38 can be used solely as a means to capture, locate or withdraw the implant 66 or it have a dual function whereby tension or force applied to the tether can first cause the device to deflate or otherwise collapse, compress or take on a configuration that will facilitate removal; and then later be used as a handle to locate, capture and/or remove the implant 66.

Deflating or Compressing the Implant

Certain intravesical treatment devices comprise expanded or inflated components to provided flotation, fixation, and attenuation, as drug delivery platforms or to prevent the device from migrating into certain regions of the urethra or bladder such as the trigone region.

Piercing or destroying the capacity of the implant to remain inflated or hold a gas or liquid can involve the step of breaking, stretching, disrupting, melting, burning, decomposing, or altering the chemical structure of at least a portion of the implant. Such techniques might employ a needle, barb, cutting blade, hooked probe, auger, morcellator, wetjet, laser, RF emitter, suction tube, ultrasonic instrument, microwave, or thermal or cryogenic element.

Figure 21:
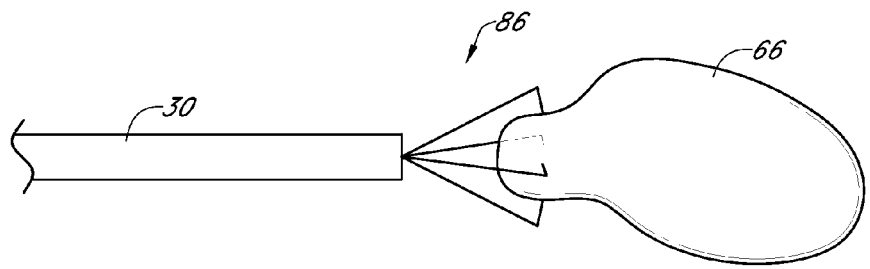
FIG. 21 is an embodiment of a retrieval instrument engaging an implant.

In one method a retrieval tool 86 is fit through the working channel of a cystoscope, catheter or other cannulated device 30, as in FIG. 21. The retrieval tool 86 may comprise an elongate shaft terminating in a handle at one end and one or more engagement members at the opposing end. The handle may comprise one or more actuators such as a finger ring, trigger, lever, or button for controlling one or more engagement members such as a pincher, grasper, tine, or blade element, grasper-like hand tool, forceps, pronged, electrode or hooked device. The engagement members may be opposable, sharpened, hooked, barbed, serrated, or have an adhesive or magnetic site. The actuators may be linked to the engagement members via a direct mechanical linkage, fluid pressure (pneumatic, hydraulic or other) or through circuitry or other modality carried by or along the shaft. In one embodiment, such as that shown in FIG. 21, the engagement member assembly may be passable through the cannula 30. In another embodiment, a retractable sleeve is mounted at the distal end of the elongated shaft. In any of these embodiments, the engagement members may be compressed or shielded prior to deployment out of the catheter, hollow shaft, or sleeve. The shaft of the removal device can also comprise a camera or working channel for delivering other instruments, passing or draining fluids and/or gases.

Teeth or similar structures of a retrieval tool or grasper 86 can be used to bite, tear, cut, puncture, rip, and/or otherwise disturb the mechanical integrity of the implant material. The teeth, hooks, prong or prongs of the grasper 86 can be drawn along the surface of the implant 66 to score, rip, or otherwise compromise the ability of the device to remain inflated. Two or more graspers 86 can engage the implant 66 and can then be advanced in opposing directions, or one relative to the other, to tear open the implant 66.

Figure 22A:
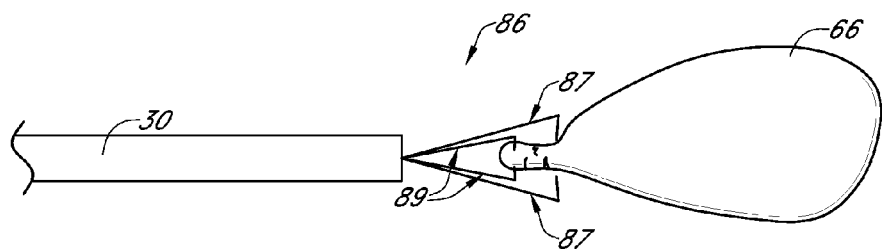
FIG. 22A is an embodiment of a retrieval instrument engaging an implant having independently movable sets of prongs.

Graspers 86 can have separate shafts or be two, two-prong graspers 87, 89 that have independent motion. Alternatively, graspers may have singular control but move at different rates or one or more grasper can be stationary while one moves, as in FIG. 22A. In one embodiment involving four graspers, all four graspers could initially grab the balloon. Upon retraction, two of the graspers move faster than the other two thereby creating relative motion and ripping the balloon. Several other designs are envisioned where there is at least two independently controlled features or, alternatively, two features that exhibit relative motion with singular control.

Alternatively, the grasper 86, while engaged to the inflated device 66 may be retracted into the cannula 30 such that the implant 66 is sheared open against the outer edge of the cannula 30. The implant 66 may then be further retracted into the cannula 30 such that the distal tip of the cannula 30 acts as a fulcrum and is operable to at least partially fold or compress and at least partially deflate the implant 66 as it is retracted within. The cannula 30 may alternatively comprise an extendable or fixed needle or barb 88 proximal its tip whereby advancement of the cannula 30 or needle 88 will puncture the implant 66.

Alternatively, the shaft of the retrieval tool 86 itself may be used as a fulcrum such that the retraction of the tool head into the shaft causes the implant 66 to become compromised. In any of these cases the end of the shaft, working channel or cannula may be optimized for deflating the implant 66. For instance, the end of the shaft may be sharpened, cut at an angle or both to facilitate penetration of the implant 66. The leading edge can also be serrated, heated, or rotated to facilitate penetration.

Figure 22B:
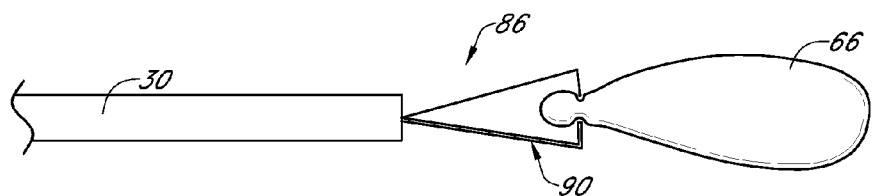
FIG. 22B is an embodiment of an implant retrieval instrument with a vacuum engaging an implant.
Figure 23A:
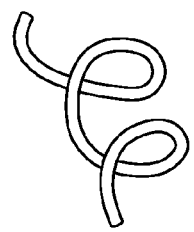
Figure 23B:
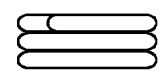
Figure 23C:
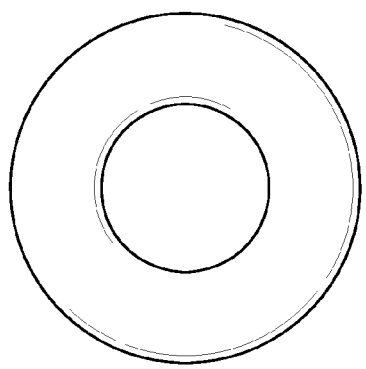
Figure 23D:
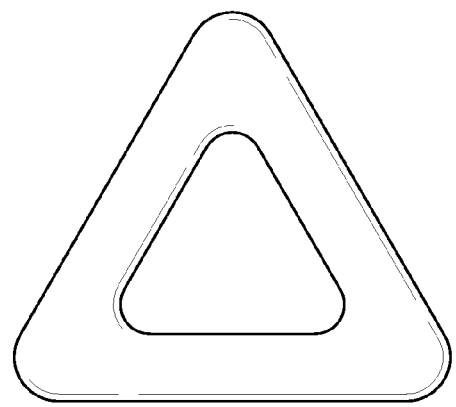

In another embodiment, the prongs for the grasper 86 may be cannulated 90 so that attaching a vacuum source to the prongs facilitates the removal of the media from the implant 66. For example, as shown in FIG. 22B, a cannulated prong 90 can have a sharp end to cut the implant 66 and then a vacuum can be applied through the cannulated prong 90 to drain the media from within the implant 66. In another embodiment, suction is applied to the shaft of the removal device. In this case, the removal tool head grabs and tears the implant 66, bringing it into contact with the removal tool shaft. Suction is applied to the shaft to remove the media from the implant 66.

In another embodiment, suction is applied to the entire bladder through a working channel or tube. In a further embodiment, a mechanical basket or cage, that may also capture or engage the implant 66, is contracted or reconfigured to compress the implant 66 along one or more axis. The mechanical cage can have a needle at the distal end pointed proximally to puncture the implant 66 as the cage is pulled into the device shaft. A hollow needle would allow deflation therethrough during compression.

As will be explained in more detail below, some embodiments provide a removal instrument that uses electrical energy to melt or burn the implant 66 to thereby deflate the device. For example, the instrument can include a resistive element to heat the implant 66. Suitable devices for performing these tasks can be fit through the working channel of a cystoscope or other similar single or multi-lumen device 30, inserted separately through the urethra, or inserted percutaneously from outside the body through adjacent tissues and through the bladder wall. Such devices can be carried in, along, or mounted along or at an end of a cystoscope, probe, hand tool, guide body, cannula, tube, hose, or other instrument described herein.

An alternative embodiment for destroying the capacity of the implant 66 to remain inflated would involve instilling into the bladder a liquid chemical that causes all or a portion of the implant 66 to dissolve and thereby facilitate its deflation, and/or compression.

Similarly, in another embodiment, an inflated implant 66 captured with a "lasso" or loop device can be compressed with the tightening of the loop. Optionally, in this embodiment, the lasso or loop can contain a needle pointing into the center of the loop to puncture and/or apply vacuum to speed the deflation of the implant 66. Finally, in yet another embodiment, the doctor or clinician presses within the vagina against the bladder to actively expel the contents of the implant 66. Similarly the doctor or other clinician can use a tool or instrument to press upon the implant 66 to compress it and expel its contents.

Once the integrity of the implant 66 to hold liquid or gas has been compromised, the implant 66 can be left or allowed to deflate over time or actively caused to at least partially deflate by compression or by vacuum with the removal device. Thereafter the device can be withdrawn within or carried by the removal device. Thereafter both devices can then be withdrawn together out of the bladder and urethra.

Implant Enhancements to Facilitate Retrieval

Implant retrieval can be a function of location, access, and ease of engagement. Accordingly, implant shape and surface pliability may be optimized for grasping, engaging, and/or puncturing. Though some intravesical implants described herein may be lubricated, or adapted to rotate or deflect off of folds in the bladder, other features described herein may enhance a surgeon's ability to retrieve the device. FIGS. 23A-F show various implants with optimized features including: a spiral (FIG. 23A) or coil (FIG. 23B) shaped implant, a toroidal (FIG. 23C) or triangular (FIG. 23D) shaped implant, a implant that comprises a magnetic or ferrous element, an implant with one or more loops or tabs for hooking the implant (FIG. 23E), a implant with an outer ring 92 and spokes 94 (FIG. 23F), an implant with a tail or tether (FIG. 23G), and an implant with an anchor that is anchored to a selected site within the bladder (FIG. 20C).

In another embodiment, shown in FIG. 23H, the implant 66 can be shaped as a toroid with interconnected central spokes 94. A removal device 150 is used wherein a hooked probe is extended out of a working channel of a catheter 30. The hooked probe can engage one of the spokes 94. Upon retraction of the hook, the implant 66 is forced into contact with either the cannula 30 or the bladder wall. This force can cause a portion of the implant to break open, initiating deflation of the implant 66. The implant 66 is then left behind within the bladder to naturally pass or is retracted through the catheter 30 as described herein.

In certain embodiments, the intravesical implant 66 may first be deflated and then retrieved by a grasper, suction, loop, hook or other device that would otherwise not be able to engage the implant in its inflated state.

Implant Enhancements to Facilitate Deflation

Implants having a predetermined dwell time after which they are automatically voided advantageously eliminate the need for a removal procedure. Such temporary implants 66 can be manufactured in a variety of ways, such as through the use of bioabsorbable or permeable materials. One or more embodiments of implants 66 provided herein can be comprised at least partially of a biodegradable material such that after a certain time period lapses the device deflates and is passed or totally degrades in the bladder. For example, the implant 66 can have a wall, seam, valve and/or other parts thereof made from an absorbable material. As used herein "absorbable" means any material which will dissolve, degrade, absorb or otherwise dissipate, regardless of the chemical mechanism, to achieve the purpose recited herein. As soon as one or more "fuse" components of the implant 66 is absorbed, the implant 66 will deflate through the resulting opening and can be expelled during normal voiding.

Alternatively, light, energy, or a chemical or agent such as a solvent can be injected into the bladder to react with the implant 66 and cause a portion of it to degrade or come apart, e.g. unseal a seam or flap, thereby allowing the gas within to escape. Similarly, the pH of the bladder can be changed via the delivery of a chemical or agent in the bladder to cause at least a potion of the implant 66 to degrade or come apart and cause deflation. Alternatively, the agent or application of energy can cause a flap to release a loop, tether, or engagement or retrieval member so the implant 66 can be more easily retrieved.

The resulting deflated components from any of the foregoing time limited embodiments can thereafter either be expelled during normal voiding, or can remain in the bladder in a deflated state until removed using a removal system.

In one embodiment, the material or portion of the inflatable container 68 (FIG. 5) is made from a gas permeable material. Over time gas dissipates from the inflatable container and the container's likelihood to pass through the urethra and be spontaneously voided increases. In one embodiment, the attenuation device is filled with approximately 20 ml of gas and the attenuation device's material allows approximately 15 ml of gas to permeate out of the attenuation device over certain time intervals, such as, for example, one, three, six, or twelve months. Once the volume remaining is less than approximately 5 ml, the attenuation device is normally voided.

The predetermined dwell time within the bladder can be influenced by a variety of design factors, including the formulation of the absorbable material and the physical shape, thickness and surface area of the absorbable component. A variety of absorbable polymers which can be used are known in the absorbable suture arts. As will be further discussed, the use of a high vapor pressure media element can be used to provide a predetermined dwell time or programmed deflation for various devices described herein.

The ideal material or device can be optimized through routine experimentation taking into account the attenuation device design and the desired indwelling time period. Attenuation devices may be time rated, such as 15 days, 30 days, 45 days, 90 days, 180 days or other as may be desired. The deflated and or partially dissolved attenuation device will be transurethrally expelled within a few days of the expiration of the rated time period from the time of implantation.

Other embodiments might employ a programmable device that over time causes failure of the intravesical implant's 66 ability to remain inflated. In other embodiments the implant 66 responds to an external signal and deflates or changes shape. Such implants 66 can comprise MEMS, RF devices, and other electronic devices known in the art.

Further details and embodiments of retrieval devices and methods will now be described.

One or more embodiments of retrieval tools described herein may be optimized to better transmit linear and rotational force, provide tactile feedback, and function in the working channel of a cystoscope. Bending stiffness, torsional stiffness, coefficient of friction of the shaft outer surface and the inner surface in contact with a pull cable (where a cable is used), and column strength should be considered in designing such instruments. One method for designing higher torsional stiffness with less effect on bending stiffness is to use metal braid in an elastomeric shaft. The braid can absorb torsional stresses while adding less to bending stiffness than, for example, using at stiffer shaft material. Selecting instrument components with low coefficients of friction (COF) is useful in lowering the forces required to operate the device and lessen the requirements of column strength and torsional rigidity. The coefficient can be lowered by using low COF materials either as the whole of the shaft or as a coating on the inside diameter, outside diameter or both. Low COF materials known to impart these desired properties include the fluorinated polymers, polyethylene, and hydrophilically coated polymers. Braid materials can include stainless steel, titanium, nitinol aramid or other high tensile modulus material (Young's Modulus greater than 500,000 psi). Shaft materials can include, PEEK, polyimide, polysulphone, fluorinated polymers (PTFE, PFA, FEP, EPTFE, PVDF, CTFE etc.), polyethylene (high or low density), polyether block amide, other copolymers of polyamide, polyamide 11, polyamide 12, polyester terethalate or elastomers of PET or PBT, ABS, other impact modified styrenics, polycarbonate or copolymers of polycarbonate, braided forms of any of these, reinforced forms of any of these, combinations of any of these. The ideal flexural modulus for the shaft would be in the range from 20,000 psi to 600,000 psi.

EXAMPLE 1

Retrieval Loop

Figure 24:
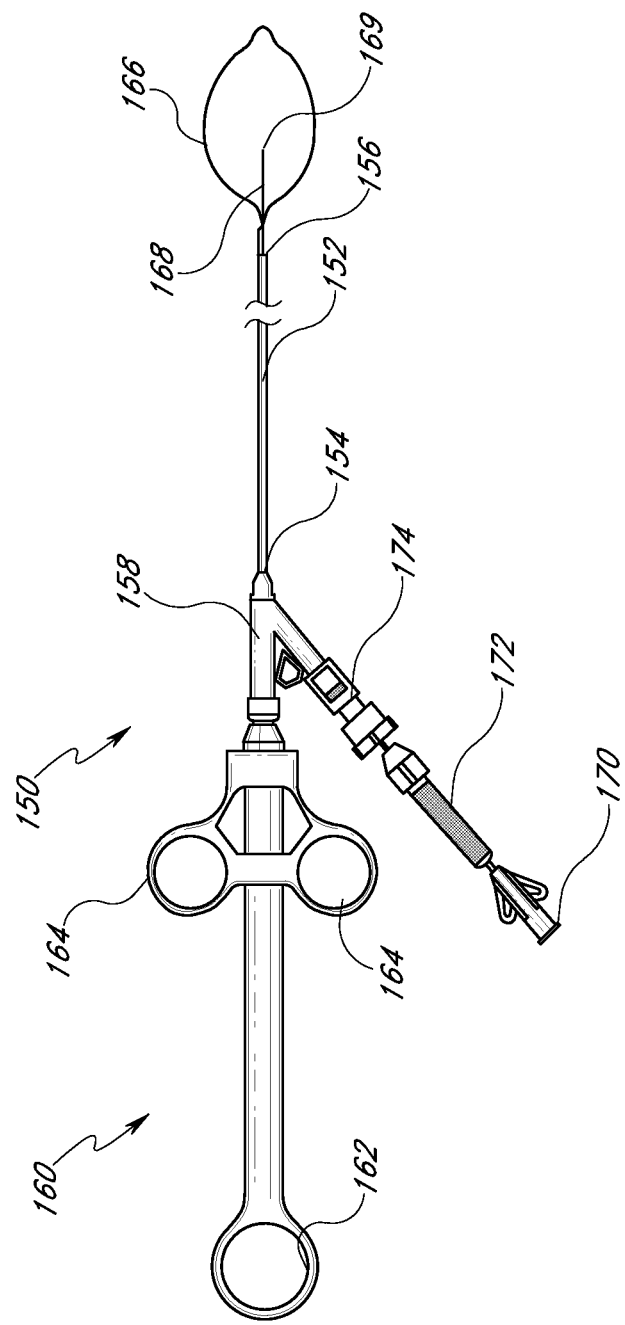
FIG. 24 is a side elevational view of a removal system.

Referring to FIG. 24, there is illustrated a side elevational schematic view of one embodiment of an intravesical removal system. This removal system 150 is adapted to retrieve the inflated attenuation device 66 as discussed elsewhere herein.

The removal system 150 comprises an elongate tubular body 152 which extends between a proximal end 154 and a distal end 156. Tubular body 152 is dimensioned to transurethrally access the bladder. In one embodiment, the removal system 150 is adapted for use in conjunction with standard urological cystoscopes (e.g. approximately 14-24 French), having minimum working channels of approximately 1.8 to 6.0 mm. For this purpose, removal system 150 in one embodiment has an overall length of approximately 76 cm and a useable length of approximately 60 cm.

The tubular body 152 may be manufactured in accordance with any of a variety of techniques well understood in the catheter and other medical device manufacturing arts. In one embodiment, tubular body 152 is extruded from a biocompatible material such as PTFE, having an inside diameter of approximately 0.05-0.1 inches and a wall thickness of about 0.01 inches.

The proximal end 154 of tubular body 152 can be connected to a Y-adaptor 158. Y-adaptor 158 carries a control 160 for controlling the retrieval system as will be described. Control 160 in the illustrated embodiment comprises a thumb ring 162 which is slideably carried with respect to a pair of finger rings 164. Axial movement of the thumb ring 162 with respect to the finger rings 164 enlarges or retracts a retrieval loop 166 extending distally from distal end 156 of tubular body 152. Retrieval loop 166 is adapted to surround the inflated attenuation device 66. In one embodiment, the loop 166 has an enlarged diameter of about 27 mm, and comprises a wire such as 0.016 inch diameter stainless steel cable wire.

In use, the loop 166 is opened once the distal end 156 of the tubular body 152 has reached the bladder. The loop 166 is positioned around the attenuation device 66, and the proximal control 160 is manipulated to tighten the loop 166 around the attenuation device 66. After the attenuation device 66 has been securely grasped by the loop 166, a deflating tube 168, preferably having a sharpened distal tip 169 thereon, is distally advanced through the wall of the attenuation device 66. Distal advancement of the deflating tube 168 may be accomplished by distally advancing a proximal control, such as control 172. The distal tip 169 is in fluid communication with a connector such as a standard luer adaptor 170 through a central lumen (not illustrated), so that an empty syringe or other device may be connected to the connector 170 and used to evacuate the contents of the ensnared attenuation device 66. In other embodiments, the contents of the attenuation device 66 are allowed to empty into the bladder. As the attenuation device 66 is deflated, the control 160 may be manipulated to pull the collapsed attenuation device 66 into the distal end 156 of the tubular body 152. The removal system 150 having the reduced attenuation device 66 therein or carried thereby may be transurethrally removed from the patient.

A wide variety of modifications can be made to the foregoing removal system 150. For example, the proximal controls 160 and 172 may be combined into a pistol grip or other configuration. Controller 172 or control 160 may additionally control deflection of the distal end 156 of the tubular body 152, or control rotation of the plane of the loop 166. In general, the removal system 150 preferably accomplishes the basic functions of enabling the location of the attenuation device 66, capturing the attenuation device, reducing the attenuation device in size and removing the attenuation device from the bladder. The capturing step may be accomplished by visualizing the attenuation device through the urological cystoscope, or by "blind" techniques, such as, for example, light reflectance, impedance, suction, ultrasound, passive induced microchip, or the magnetic locator.

EXAMPLE 2

Grasper

An implant removal system 150, according to certain embodiments can comprise a grasper 86. The grasper 86 can use prongs or jaws to engage the implant 66 and to assist in the removal of the implant 66.

Steps of a method using the grasper 86 are illustrated in FIGS. 25A-D. The bladder can optionally be drained and the implant 66 located either visually or otherwise. A cannulated access device 30 is inserted into the urethra. When the tip of the catheter is passed into the bladder a small balloon or anchoring member may be deployed to fix the catheter 30 in place (not shown). The grasper 86 is then advanced through the catheter 30.

Figure 25A:
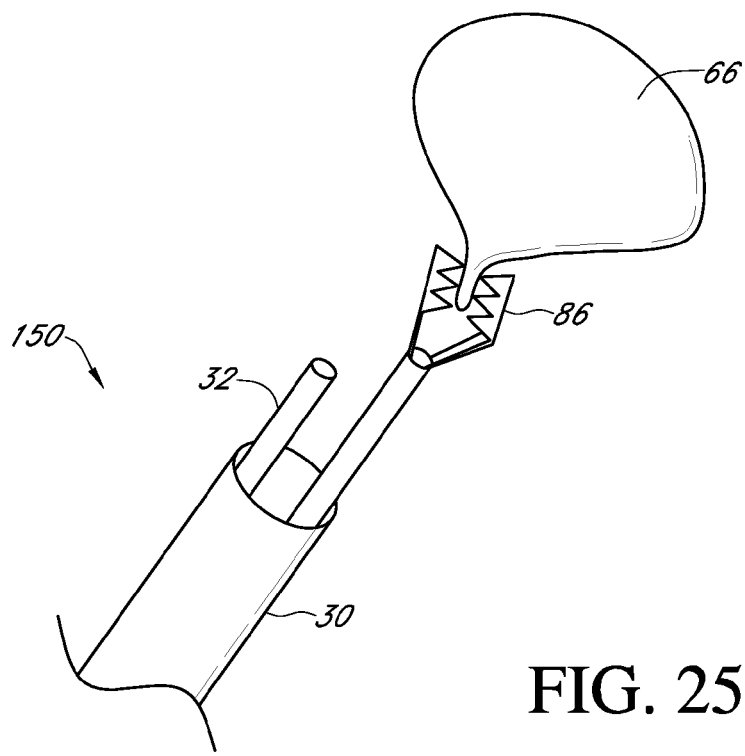
FIG. 25A shows a removal system with an optical instrument, a cannula, and a grasper engaging an implant.
Figure 25B:
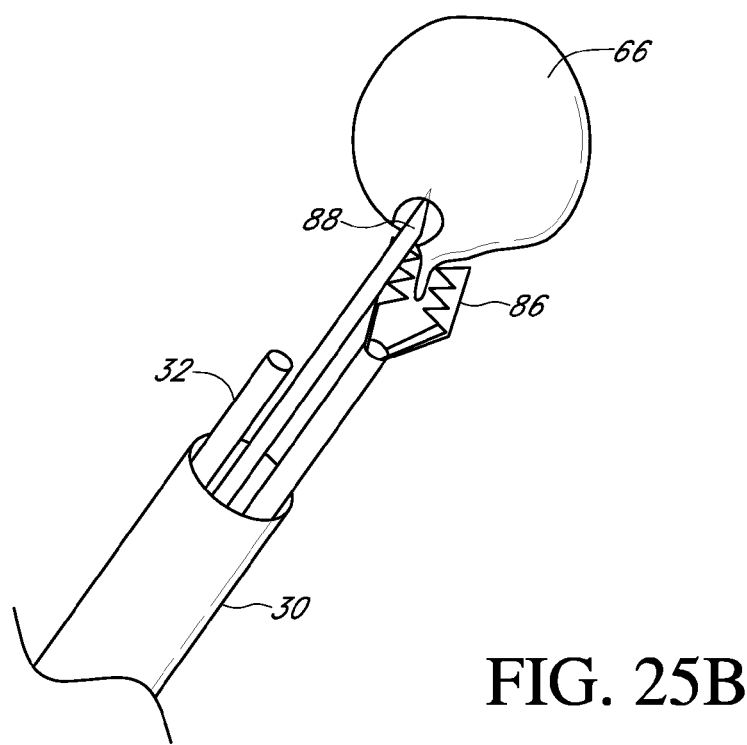
FIG. 25B has the removal system of FIG. 25A where a piercing element is cutting the implant.

Referring to FIG. 25A, the grasper 86 engages the implant 66. The optical instrument 32 shown can be used to locate the implant 66. In some embodiments, the optical instrument 32 is located on the grasper 86. The optical instrument can be used to position the tip of the grasper 86 proximal to the implant 66. FIG. 25B shows a piercing element 88 advanced through the cannula 30 to pierce the implant 66. The cannula 30 can optionally comprise the piercing element 88 operable to pierce the implant 66 when the implant 66 is retracted against the cannula 30 or the cannula is advanced against the implant.

Figure 25C:
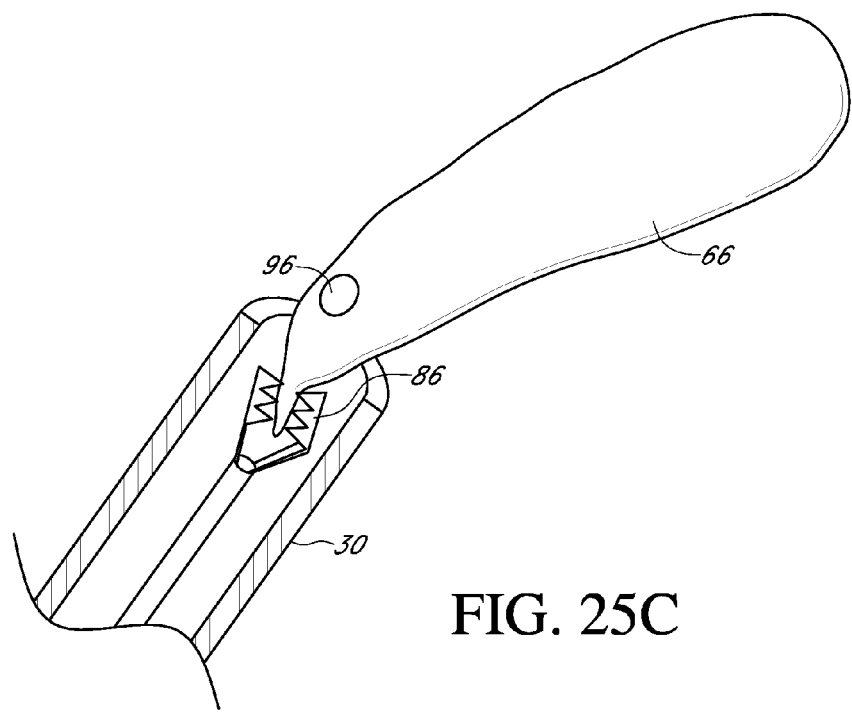
FIG. 25C is a view of the pierced implant being pulled into the cannula by the grasper.
Figure 25D:
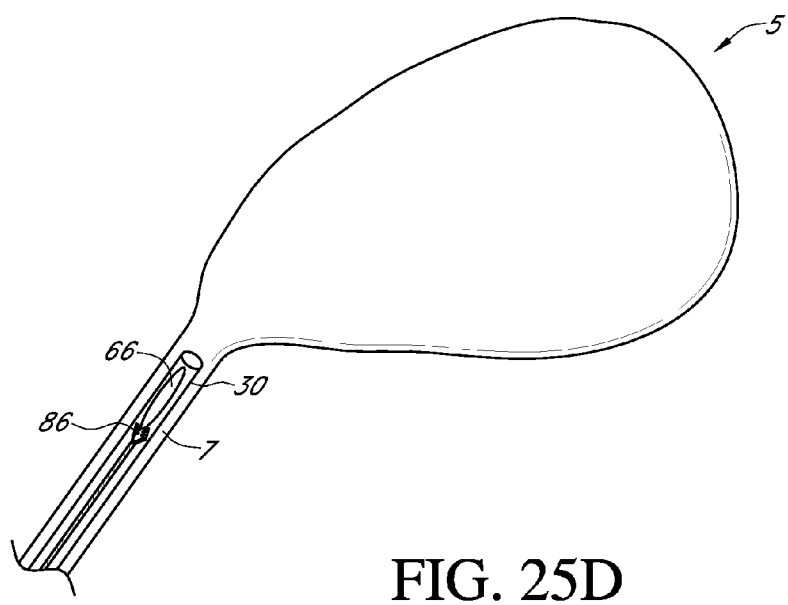
FIG. 25D shows the implant removed from the bladder into the cannula.

After the implant 66 is punctured (at 96), it can be deflated in many ways. In some methods the implant 66 is allowed to deflate on its own. In other methods the implant 66 is deflated by forcing the implant against another structure such as the bladder wall or the cannula 30. FIG. 25C shows the partially deflated implant 66 being drawn into the cannula 30. This action can cause the implant 66 to deflate more quickly. FIG. 25D shows the deflated implant 66 withdrawn into the cannula 30. At this point, the removal device 150 and the implant 66 can be removed from the urethra.

EXAMPLE 3

Cage or Basket

Figure 26A:
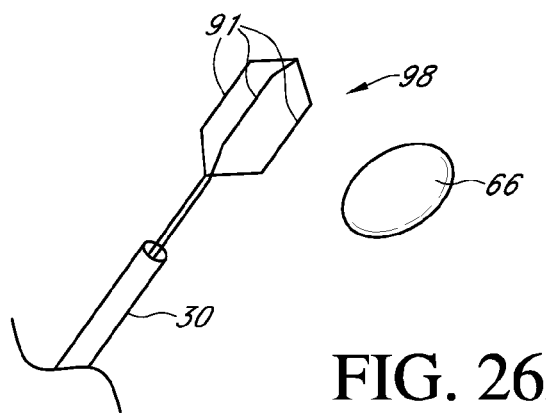
FIGS. 26A-B are views of a removal system having a cage, basket or net for removing an implant from the body.

FIG. 26A shows a cage-like device 98 in an expanded position after exiting a delivery tube or catheter 30. The cage 98 can have two or more "legs" 91. The legs 91 can form the structure of the cage 98. For example, two legs 91 can form a loop sufficient to contain certain implants. Alternately, Other embodiments include three legs 91 and still others contain four or more legs 91.

Figure 26B:
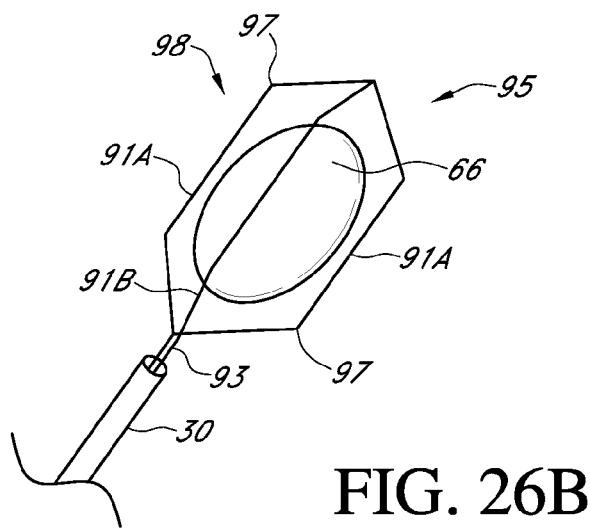

The cage 98 can have a first position configured to pass through the catheter 30 and into the anatomical structure. The cage 98 can have a second expanded position configured to obtain or catch the implant 66 within the cage 98. In some embodiments, the legs 91 have hinges or joints 97 that allow the cage to move from the first position to the second (FIG. 26B). In other embodiments, the legs are preformed or bent to be biased towards either the first or second position, or a position in-between.

For example, in some embodiments the legs 91 are preformed to be biased towards an expanded position. The cage 98 and legs 91 can be compressed to fit inside the catheter 30 and can expand towards their biased position after exiting the catheter inside the anatomical structure. After obtaining the implant 66 within the cage 98, the cage 98 can be withdrawn from the anatomical structure into the catheter 30. The act of withdrawing the cage 98 into the catheter 30 can cause the cage 98 to collapse, or can compress the cage 98 and move it towards the first position.

In some embodiments, two of the three or more legs 91 can be oriented so as to create a window or door 95 on one side of the cage 98 that is larger than the space between the legs 91 on the other sides on the cage 98. This larger window 95 can advantageously be used for capturing the implant 66. FIG. 26B shows a cage 98 with three legs 91. Two of the legs 91A are oriented roughly perpendicular to the other leg 91B, thereby creating the larger window or door 95 on one side of the cage 98 for capturing the implant 66. When the implant is captured it can be retracted towards the catheter 30. In certain embodiments, retraction of the cage 98 into the catheter 30 collapses the cage 98 on the implant 66. This can compress the implant, and in some instances pop or cause a leak or controlled expulsion of the implant's contents.

As mentioned above, the cage 98 can have hinges 97. The hinges 97 can allow the legs to move between different positions. A control 93 can be used to control the positions of the legs 91. For example, all of the legs 91 can be connected and the control 93 can be connected to one of the legs 91 such that the position of the leg 91 connected to the control determines the position of all of the legs 91.

Figure 26C:
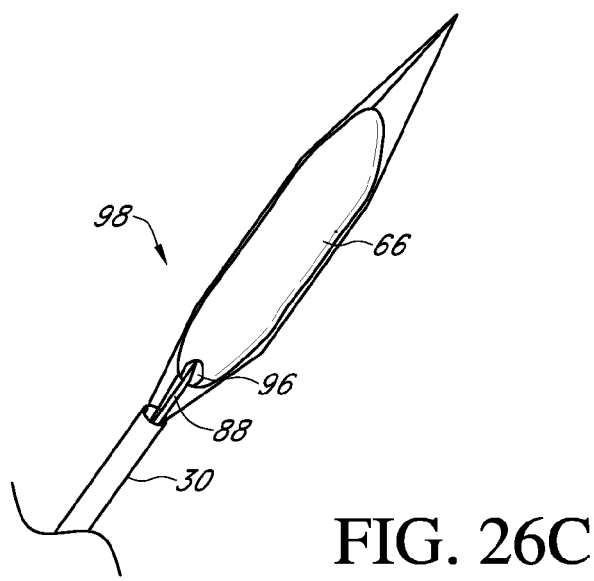
FIG. 26C shows another embodiment of a cage, basket, or net removal system.

The tip of the catheter can optionally carry an implant piercing or compromising element 88 that pierces the implant 66 as it is retracted against the piercing element 88, as shown in FIG. 26C. The cage 98 can then compress and deflate the implant 66. Alternatively, the tip of the cage 98 can include a needle at the distal end, pointed proximally to facilitate puncturing and deflating the implant 66. The implant 66 can then be retracted into the catheter 30 or the implant 66 can be released and allowed to pass naturally from the implantation site.

EXAMPLE 4

Heating Element

Some embodiments provide a removal instrument 150 that uses electrical energy to melt or burn the implant 66 to thereby deflate the implant. For example, one or more sides of a retrieval tool or grasper 86 can be adapted to transmit thermal energy including RF, electrical, laser, or hypothermal. The heated sides or sections are operable to melt the exterior of an implant 66 comprising a thermoplastic material. According to some embodiments, this can allow the removal instrument 150 design to be optimized for grasping ability while allowing easy penetration and destruction of the balloon film with a heated surface. At the same time, according to these embodiments, the function of separately puncturing the implant 66 does not need to be considered.

Figure 27A:
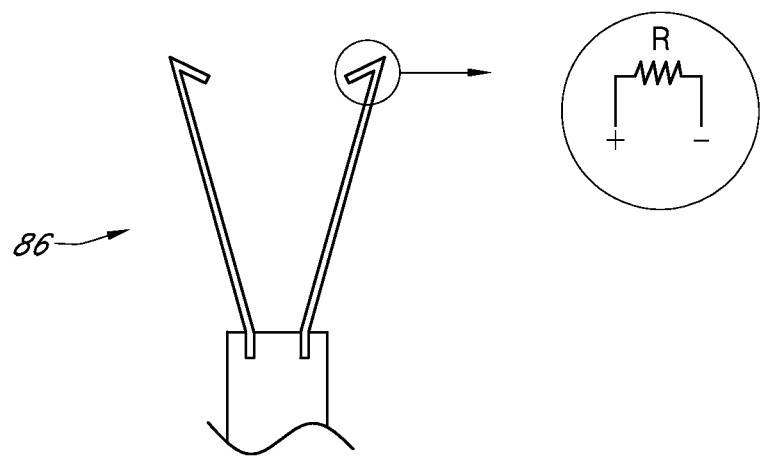
FIGS. 27A-B illustrate embodiments of a removal system that uses heat to deflate a balloon-like implant.
Figure 27B:
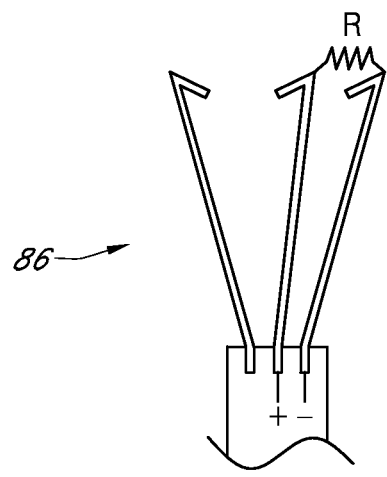

The heating element may be a resistor "R" as shown schematically in FIGS. 27A and 27B. The heating element can also comprise RF technology, as is used in electrosurgical units. The resistor "R" may take many forms. The prong itself can form the resistor. The resistor "R" may be printed on a miniature circuit board attached to the prong. Preferably the flexible circuit board is less than 0.030" wide. The flexible circuit board can be attached to a prong as a pad on the inside (balloon side) surface of the prong. The flexible circuit board can be a thin film deposited on the prong.

In another embodiment the prong or a part of the prong itself can be made from nichrome resistance wire. In another embodiment, the resister can be constructed from nichrome film attached to the inner side of one or more prongs. Alternatively, the resistor can be made from constantan, inconel, TaN, Kanthal or any other appropriate resistance wire or alloy. In another embodiment, the prong can be made from resistance wire. The geometry of the prong can be designed to concentrate the current density and therefore the heat at a particular location along the prong, such as the apex.

One embodiment comprises a resistive element at the end of a catheter carrying a forceps or grasper. Upon the application of current, the resistive element becomes hot, exceeding the melting point of the implant material and breaking it open.

In use, currents between 0.5 and 10 amps can be used through resistances between 0.01 ohm and 1K ohm. This can generate temperatures between 250 F and 500 F and can last for between 0.01 seconds and 3 seconds, preferable around 1 second to heat the element sufficiently to melt the implant material. A current of 3.2 amps through a resistance of 1.0 ohm has been shown to break a polyurethane balloon in approximately 1 second under water.

In some embodiments, a resistor "R" can be connected between two prongs, as shown in FIG. 27B. The prongs may or may not be insulated. The resistor "R" can heat up while the prongs do not.

The circuit can be activated with a button on the handle of the device or can be automatically closed when the device contacts the implant 66. In some embodiments, contacting the implant causes the positive lead to press against the negative lead, closing the circuit. In another embodiment, the implant can be conductive. Contact between the implant surface and the prong could close the circuit. Varying the resistance of the implant can control of the current flow and heating rate. When the prong is pulled away from the implant the circuit is opened and can cool immediately.

In some embodiments, a short pulse may be created by mechanical or electrical components to prevent continuous heating of the resister. Some form of capacitance may be used to create a high energy but short duration electrical pulse.

The electrical energy for the circuit can come from an individual battery or battery pack, possibly multiple 1.5V AA sized batteries or a single 9V battery. Alternatively, an electrosurgical unit (such as those produced by Valleylab of Boulder, Colo.) may be used to provide AC current to the circuit.

In one embodiment, a capacitor can be used to store electrical energy from a power source with limited current producing capacity, such as a battery, which, when fired, gives a short burst of high current energy to rapidly heat the tip. In another embodiment, the catheter tip has traces of deposited thin film metals which act as conductors to bring electrical energy to a resistor at the tip. The circuit can be opened and closed in several ways including by button, lever, switch or other actuator on the handle or catheter shaft, automatically by designing one end of the circuit to be separated from and out of contact with the other end of the circuit coming into contact only when the tip is pressed against a surface.

Figure 28A:
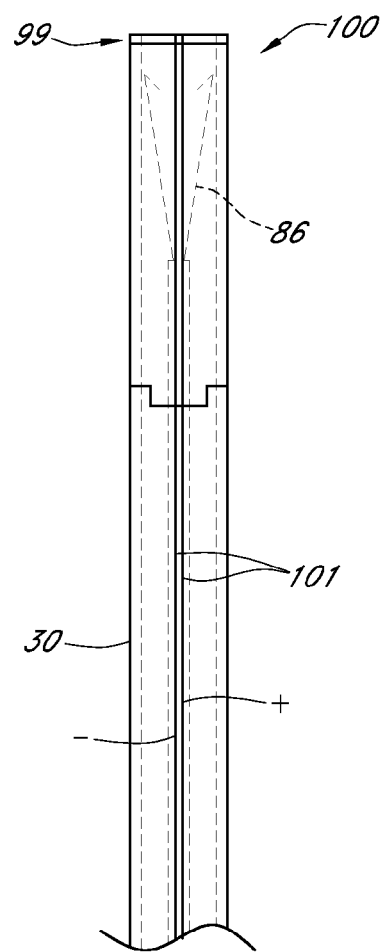
FIG. 28A is a side view of a cannula having a thin film resistor on the end.
Figure 28B:
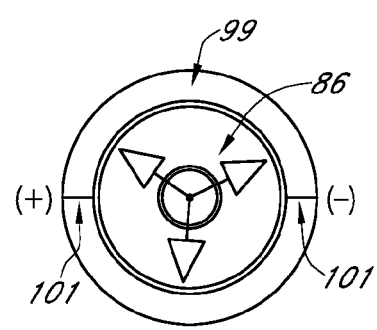
FIG. 28B is an end view of the cannula of FIG. 28A.

In another embodiment, as shown in FIGS. 28A and 28B, the tip of a catheter 30 comprises a heating element 99. The tip 100 may be a thermally resistant tip made from ceramic, metal, or high temperature plastic onto which a thin film resistance metal is plated to create the heating element 99. The resistance film can be directly connected to conducting elements in the catheter shaft or connected to a conducting thin film 101 which is then attached to a conducting element in the shaft. Although bipolar electrocautery catheters are available, this embodiment works differently as it does not require tissue (or other conductive material) to close the circuit. In use, the tip 100 of the catheter 30 becomes a heated element 99 capable of melting the surface of the implant 66 freeing up the inside of the catheter for the grasping tool. U.S. Pat. Nos. 4,532,924 and 6,986,767 are herein incorporated by reference and illustrate examples of bipolar electrocautery devices.

Figure 29A:
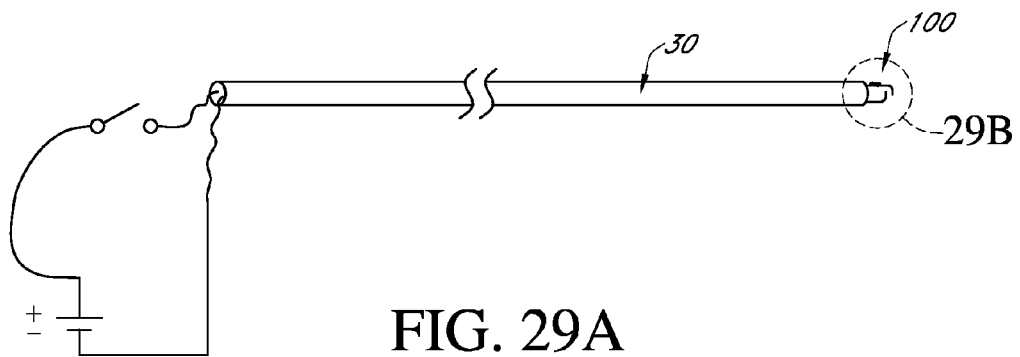
FIG. 29A is a schematic side view of a removal system that uses heat on the cannula to deflate a balloon-like implant.
Figure 29B:
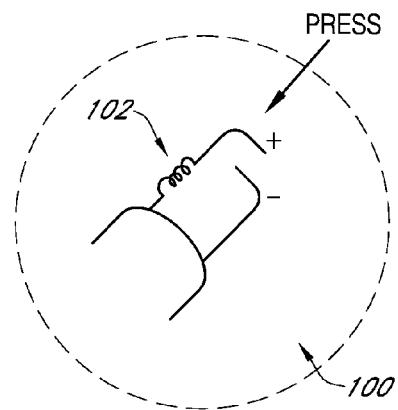
FIG. 29B is a schematic detail view of the removal system of FIG. 29A.

In another embodiment, a device similar to that shown in FIGS. 28A and 28B, is made such that the positive and negative leads are situated one over the other without touching, thus leaving the circuit open with no current flow. When the tip 100 of the catheter 30, as shown in FIGS. 29A and 29B, comes into contact with a surface the leads make contact, closing the circuit, and heating the resistor. When contact is released, the circuit opens, stopping current flow, and ending any heating of the tip. This reduces the possibility of overheating the tip or of heating the tip at an inopportune time. As shown in the detail view of FIG. 29B, at least one of the leads can be spring loaded 102 to allow the at least one lead to move towards the other lead to close the circuit. Other mechanisms can also be used to move one lead towards the other.

Figure 29C:
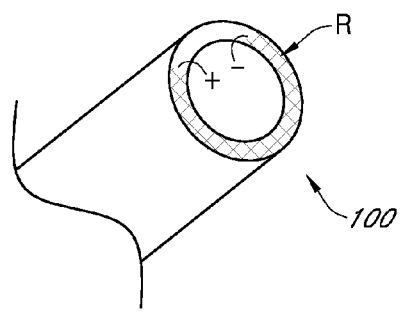
FIG. 29C is an embodiment of a removal system similar to that shown in FIG. 29A.

FIG. 29C illustrates an alternative tip 100 with a resistor "R" formed on the tip.

Though various embodiments of delivery and retrieval devices have been disclosed, it is to be understood that additional variations can also be made and are envisioned. For example, the removal devices and methods can be configured to prevent contact of the implant with the trigone area of the bladder in similar ways to that described with respect to the delivery devices and methods. As one example, the removal device can have a lateral opening similar to the openings described in FIGS. 10A-E.

In accordance with another aspect of the disclosure, the delivery system and the removal system of the attenuation device or accumulator are two separate instruments. In another embodiment, the delivery system and the removal system are implemented using a single instrument. In yet another embodiment there is provided one instrument having different distal ends for the delivery system and the removal system.

Therapeutic Benefits

Therapeutic Benefits, methods of improving the dynamic compliance of the bladder, methods of improving the contractility of the bladder: Based on demonstrations by Solace, Inc. it is believed that the removal of high frequency, repetitious insults to the bladder wall for a 5 day to 180 day period of time increases the dynamic compliance of the bladder and reduces symptoms of incontinence by: precluding/reducing the stretch of elastin fibers; reducing of the conversion of elastin fibers into collagen; allowing the "stretched" muscles of the bladder wall to shorten, thereby improving compliance and bladder wall contractility; removing pressures exerted on the pelvic floor and connective tissues, allowing retraining and healing, increasing urethral resistance; placing the attenuation device in the bladder provides passive resistance to the bladder neck and bladder wall, allowing the muscles to strengthen. These and other therapeutic benefits could last up to about 30 days to about one year. An additional benefit of attenuation and/or improving bladder compliance includes improved flow during voiding (i.e. method of improving flow during voiding by "smoothing" the pressure within the bladder). Abdominal straining, resulting in a raised abdominal pressure $P_{abd}$ and, therefore, an increased intravesical pressure is not often employed in normal voiding, nor is it usually as efficient as detrusor contraction in producing voiding. If, however, the detrusor contraction is weak or absent abdominal straining may be the only available way of voiding and may then become of primary importance.

Another benefit of attenuation and/or improving bladder compliance includes improved urethral closure pressures. Changes in abdominal pressure affect not only the intravesical pressure but also the urethra, proximally by direct mechanical action. The result is that when the abdominal pressure rises, as during straining or a cough, the urethral pressure discussed above also rises. The maximum urethral closure pressure therefore does not diminish, and may even increase. This represents a natural defense against leakage during stress. This process is enhanced by the attenuation of intravesical pressures within the bladder, with full exposure of the urethra to increased abdominal pressures.

Another benefit of attenuation and/or improving bladder compliance includes improving the symptoms of benign prostatic hypertrophy ("BPH"). As the prostate enlarges, flow rates are reduced and residual volumes increase. The symptoms of low flow are increased as the increased intravesical pressure causes a decrease in the compliance of the bladder wall, bladder muscles elongate, elastin converts to collagen in the most severe cases), making it even more difficult for the bladder to "push" the urine through the restricted opening of the prostate. As this cascade continues, the symptoms of benign prostate hyperplasia increase. Placement of an attenuation device in the bladder reduces symptoms of BPH by improving flow, increasing the compliance of the bladder wall, removing high pressure insults to the bladder wall, and allowing the bladder wall muscles to shorten, all permitting the bladder to more effectively "push" the urine through the urethra and prostate. In one embodiment, the attenuation device in the bladder reduces the symptom of BPH by attenuating increases in pressure within the bladder by reversibly reducing its volume in response to the pressure increases. For example, in one embodiment, the attenuation device reduces its volume by at least 5%. In another embodiment, the attenuation device reduces its volume by at least 10%. In yet another embodiment, the attenuation device reduces its volume by at least 25%.

Figure 30A:
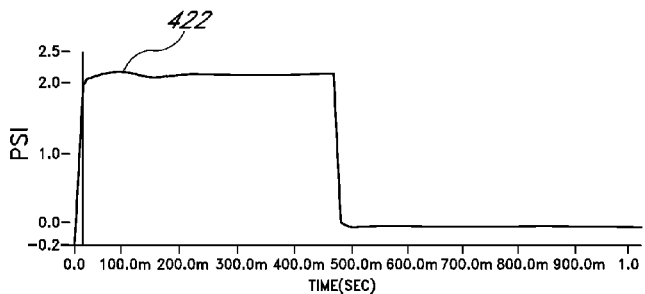
FIGS. 30A-D present graphs of attenuation/pressure reduction vs. time for various attenuation device air volumes.
Figure 30B:
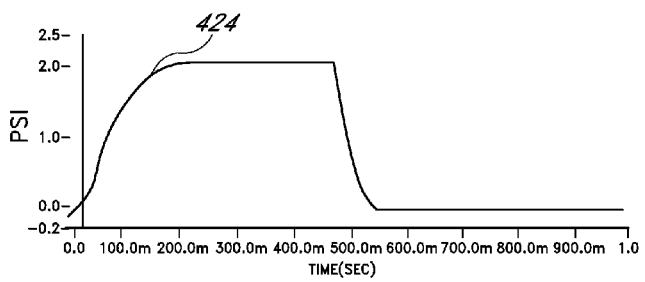
Figure 30C:
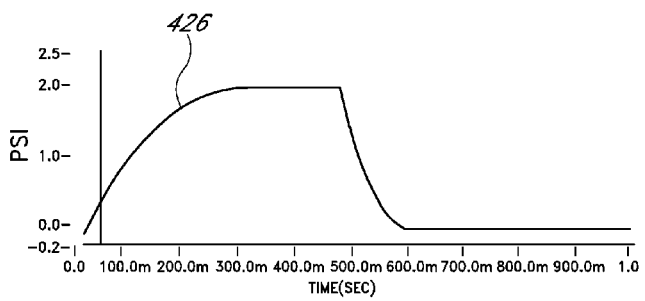
Figure 30D:
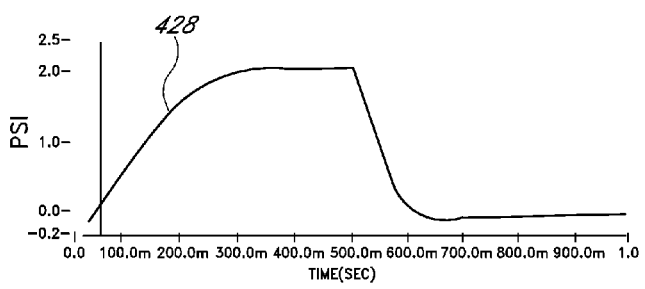

FIGS. 30A-D illustrate attenuation (i.e. pressure reduction) with various attenuation device air volumes. The data for these graphs were generated using a bench top bladder simulation program. Here, the maximum spike pressure is 2.0 psi. The spike event duration is approximately 40 ms, which is approximately equivalent to the duration of a coughing or sneezing event. With reference to FIG. 30A, a test was conducted with a 250 ml rigid plastic container filled with synthetic urine or water. A regulated pressure of 2.0 psi was introduced into the container via a controlled solenoid valve. A pressure transducer detected the pressure rise. Here, the pressure rise time (Tr) of the container pressure 422 to reach 2.0 psi was approximately 40 msec. With reference to FIG. 30B, a similar test was conducted on a 250 ml rigid plastic container. Here, an attenuation device filled with 15 ml of air was placed inside the container filled with synthetic urine. Here, the Tr of the container pressure 424 to reach 2.0 psi was approximately 195 msec. Thus, the attenuation device slowed the rise time by 4.8×. During the spike event (i.e. when time equaled 40 msec), the pressure inside the container reached 0.7 psi (vs. 2 psi), resulting in a 65% reduction of pressure vs. baseline. With reference to FIG. 30C, a similar test was conducted; the only difference being that the attenuation device was filled with 25 ml of air. Here, the Tr of the container pressure 426 to reach 2.0 psi was approximately 290 msec. Thus, the attenuation device slowed the rise time by 7.25×. During the spike event (i.e. when time equaled 40 msec), the pressure inside the container reached 0.5 psi (vs. 2 psi), resulting in a 75% reduction of pressure vs. baseline. With reference to FIG. 30D, a similar test was conducted; the only difference being that the attenuation device was filled with 30 ml of air. Here, the Tr of the container pressure 428 to reach 2.0 psi was approximately 340 msec. Thus, the attenuation device slowed the rise time by 8.5×. During the spike event (i.e. when time equaled 40 ms), the pressure inside the container reached 0.4 psi (vs. 2 psi), resulting in an 80% reduction of pressure vs. baseline.

Figure 31A:
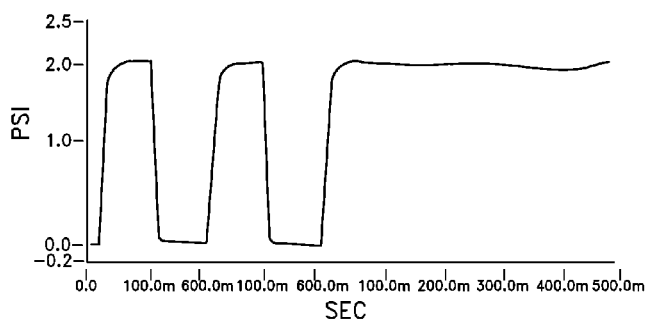
FIGS. 31A-D show pressure vs. time curves generated by a bench top bladder simulator.
Figure 31B:
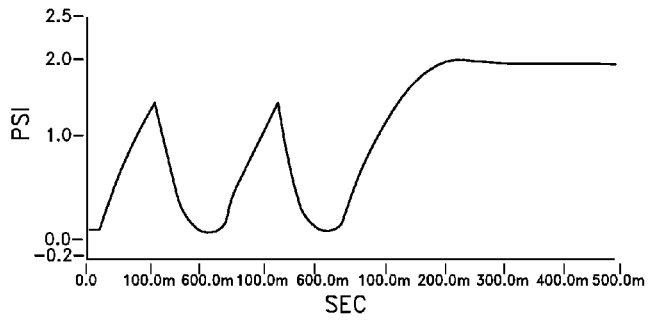
Figure 31C:
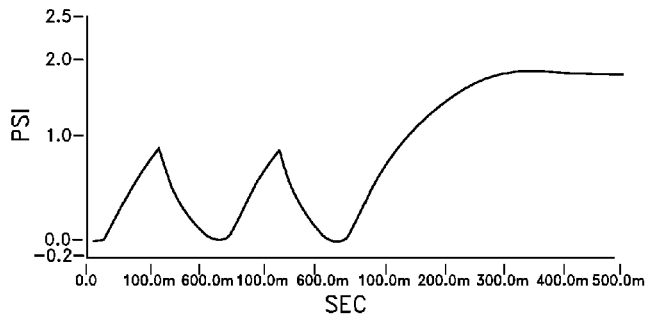
Figure 31D:
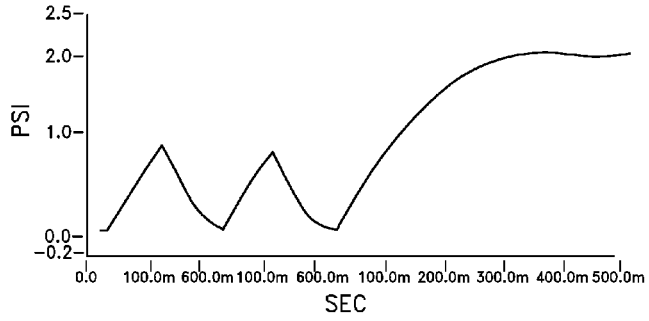

FIGS. 31A-D show pressure vs. time curves generated by a bench top bladder simulator. FIG. 31A shows the baseline pressure-time curve without an attenuation device. FIG. 31B shows the pressure-time curve with an attenuation device having a 15 cc air volume. FIG. 31C shows the pressure-time curve with an attenuation device having a 25 cc air volume. FIG. 31D shows the pressure-time curve with an attenuation device having a 30 cc air volume.

Another benefit of some of the devices discussed herein is the ability to treat and/or prevent stress urinary incontinence. A method of preventing stress urinary incontinence can include providing a pressurized implant operable to reversibly occupy intravesical space in response to a pressure increase event within a bladder said response operable to impede the rate of an intravesical pressure increase event during an initial period. The initial period can be around 0 milliseconds to 1 second from the event. This can beneficially allow time for neurological signaling of a guarding reflex to increase the outlet resistance of an external urinary sphincter sufficient to prevent leakage of urine through said sphincter after said initial period. The selected treatment period can beneficially facilitate rehabilitation of a neuromuscular system of the bladder and restoration of continence.

Selectably Pressurized Implants

All liquids (and for that matter solids) will evaporate at a given temperature until they saturate the space above the liquid with their vapor. The pressure exerted by that saturated vapor is the vapor pressure. The vapor pressure goes up with temperature and when a liquid is heated until its vapor pressure is above one atmosphere, it boils while trying to maintain the space above it at its vapor pressure, now more than one atmosphere. Likewise if the vapor of a liquid is concentrated (e.g. compressed) to be present at a partial pressure (concentration) above its vapor pressure, it condenses. Some liquids have very low vapor pressures (e.g. cooking oil, high molecular weight PFCs) and some have high vapor pressures (e.g. alcohol, gasoline, lower molecular weight PFCs). Within this document the abbreviation, PFC, is used for perfluorocarbon.

Partial pressure is both a measure of pressure (force/area) and a unit of gas concentration (at constant temperature, proportional to moles/volume). A "p" placed in front of the chemical symbol of a gas generally denotes it as the partial pressure of that gas, e.g. $pCO_2$. The total of all partial pressures inside a container is the gas pressure measured inside that container. Diffusion is controlled by the difference in concentration across a boundary or membrane and thus for gases the rate is proportional to the difference in partial pressures of the gas on both sides of a membrane.

Gas tension is a measure of the amount of a gas dissolved in a liquid (e.g. $O_2$ or $CO_2$ in blood, urine). It is a preferred measurement for the liquid systems described here. Gas tension is defined as the partial pressure of a gas that would equilibrate with the liquid sample causing it to contain the same quantity (g/ml or moles/liter) of that gas as is in the test sample. It is expressed as a partial pressure with units of mm Hg, torr, or cm $H_2O$.

Many of the devices herein rely on compliance to attenuate or buffer pressure spikes, such as in the bladder. Compliance is the change in volume (V) of a device per unit change in applied pressure (P) on the device (dV/dP). This is the slope at any point in a plot of volume (V) of the device vs. pressure (P) applied to the device. For example, compliance is often calculated from V vs. P curves of the lung to indicate the effort needed to breathe. In our case it is a measure of how capable a device is of dampening a pressure spike. High compliance means a large device volume reduction to relieve a given pressure spike. Since the V vs. P curve is often non-linear, the slope, dV/dP=compliance, is not constant throughout the working region of a device. Internal gas pressures, geometry of the device, volume of the device and elasticity of the skin of the device can be chosen to maximize compliance under the conditions expected for each application.

Tables and charts are readily available which show the vapor pressure of a given PFC as a function of temperature and can be useful in designing a device with certain pressure properties, as will be shown below.

For liquids, the amount of dissolved gas is stated as a gas tension. This is the equilibrated partial pressure of the gas that results in the amount of dissolved gas. Since this is the liquid concentration that is relevant for diffusion across biological membranes, it is commonly used in medicine for gases in the blood e.g. $pO_2$ or $pCO_2$ and has units of pressure, e.g. mm Hg, or cm $H_2O$. Gas tensions are actually a measure of saturation level rather than true concentrations. Thus, a sample of blood with a $N_2$ tension of 593 mm Hg or $O_2$ tension of 160 mm Hg would be saturated with those gases when exposed to a gas mixture containing partial pressures of 593 mm Hg of $N_2$ or 160 mm Hg of $O_2$. This is regardless of how many moles or milligrams per ml were dissolved in the sample. Unlike gaseous systems where compression of the system elevates the gaseous partial pressures in the system, gas tensions of gas molecules dissolved in an incompressible liquid are not affected by hydrostatic pressures.

Another factor to consider is the fact that a vessel/balloon containing a gas and/or a liquid could be constructed of an elastic material. As the pressure of gas inside the balloon increases relative to the pressure outside the vessel, the vessel may seek to expand to neutralize the difference in pressure between inside and outside the vessel. As the vessel expands it will stretch and exert a force which countermands the force of the gas pressure within. This is sometimes known as skin tension causing skin pressure. Thus, an equilibrium state could exist where the pressure outside such an elastic vessel is 760 mm Hg, the pressure inside the vessel is 780 mm Hg, and the skin tension of the vessel exerts a force on the gas within it that is equal and opposite to the expansionary force of the extra 20 mm Hg within the vessel.

It is important to consider the gases and the concentrations of those gases which may be found within the body when placing an implant therein. Generally, there is a close relation to the gases found in the ambient atmosphere outside the body, and those within. In normal air, the largest component is nitrogen. The components of a gas are, in fact referred to according to their partial pressures. That is, when it is said that air is 78% nitrogen, it means that this is the percentage of the total gas pressure due to nitrogen. The second most common component is oxygen, whose partial pressure contributes 21% of total atmospheric pressure. Other gases make up the remaining 1% (e.g. $CO_2$ is 0.04% and thus may be neglected in most calculations discussed herein) of the total pressure. Also, the body does not metabolize nitrogen, and it is present within the body's fluids, and its partial pressure contribution is related to its contribution outside the body, limited by its solubility in the respective fluids. Thus, if the ambient pressure is 760 mm Hg, then the total pressure is 760 mm Hg, the partial pressure of nitrogen is 593 mm Hg or 78%. The partial pressure of oxygen, expressed as $pO_2$, is 160 mm Hg, or 21%. The partial pressure of the remaining gases would be about 8 mm Hg, or about 1%.

The nitrogen concentration in blood is related to nitrogen's solubility in blood but, since it is not metabolized, its gas tension is essentially equal to the nitrogen partial pressure in air. The oxygen concentration in blood is more complex, since oxygen is actively bound to hemoglobin in the blood—boosting blood's capability to carry oxygen. Also, unlike nitrogen, oxygen is metabolized in the body, so its concentration can vary significantly within the body. The amount of oxygen present in blood varies and is reported as "oxygen saturation," or the % of the maximum oxygen that blood can carry or the oxygen tension $pO_2$. For a healthy person, this is typically in the range of 95 to 98%. Venous blood is typically in the range of 60 to 80%. When considering the diffusion of oxygen across membranes the preferred measurement is the oxygen tension or $pO_2$. Oxygen concentration in fluids such as cerebrospinal fluid, vitreous humor and bladder urine also varies.

In the article "Noninvasive Oxygen Partial Pressure Measurement of Human Body Fluids in Vivo Using Nuclear Magnetic Imaging" by Zaharchuk et al. (Acad. Radiol. 2006; 13:1016-1024), a table of gas tensions of oxygen in various body fluids is detailed. Information from that article is summarized in Table 1, below. The authors, Zaharchuk et al., attempted to measure partial pressure of gases in the body using MRI. In an effort to verify their measurements they performed a literature review to see what other researchers had estimated the partial pressures to be.

In Table 1, the oxygen partial pressure for particular bodily fluids is given. The middle column is Zaharchuk's measurement and the right column is what they found by studying the literature. Also, one should note that the partial pressure of oxygen in the atmosphere is 160 mm Hg and thus consequently fully air equilibrated fluids, if there were no consumption, would have oxygen tensions of 160 mm Hg.

TABLE 1

Body Fluids and Oxygen Partial Pressure Values

| Body Fluid | Actual $pO_2$ measured by Zaharchuk et al. (mmHg) | Literature Review "best estimate" range of $pO_2$ (mmHg) |
| --- | --- | --- |
| Cerebrospinal fluid in Lateral ventricles | 52 +/− 14 | 30-74 |
| Cerebrospinal fluid in Cisterna magna | 62 +/− 29 | 31-74 |
| Cerebrospinal fluid in cortical sulcal | 138 +/− 46 | Not Found in the Literature |
| Cerebrospinal fluid in lumbar subarachnoid | 69 +/− 22 | 40-57 |
| Vitreous Humor | 63 +/− 34 | 9-20 |
| Bladder Urine | 63 +/− 16 | 25-80 |

Pressure within the abdomen and within the bladder is typically measured in units of "centimeters of water" or cm $H_2O$, where 1.0 mm Hg corresponds to 1.33 cm $H_2O$, So, for example, the partial pressure of oxygen in atmospheric air is about 212 cm $H_2O$, and the partial pressure of oxygen in bladder urine is approximately 84 cm $H_2O$. Hence, there is a partial pressure "deficit" of oxygen in bladder urine corresponding to approximately 129 cm $H_2O$.

Provided herein are improved pressurizable, compressible and/or expandable devices for attenuating pressure waves or spikes in the body and for preventing or relieving various pathological conditions and improving surgical outcomes.

Several of the therapeutic devices herein are comprised of implantable balloons, vessels, enclosures, envelopes, pistons or hydraulic devices that contain gas or gas/liquid mixtures. Such devices can define a range of permeability. Examples of such devices can be found in U.S. Pat. No. 7,347,532 and US Publication No. 2007-0156167 herein incorporated by reference. Various embodiments herein provide for rapid, delayed or controlled in situ inflation or deflation. In other embodiments the devices may further be comprised of relatively soft, distensible, thin, and consequently gas permeable membranes. Over time these devices will deflate and become ineffective or fail unless fitted with a "gas generator" of a selected high vapor pressure media. Certain other methods and devices provided herein include the maintenance of inflation for a selected period of time.

Figure 32A:
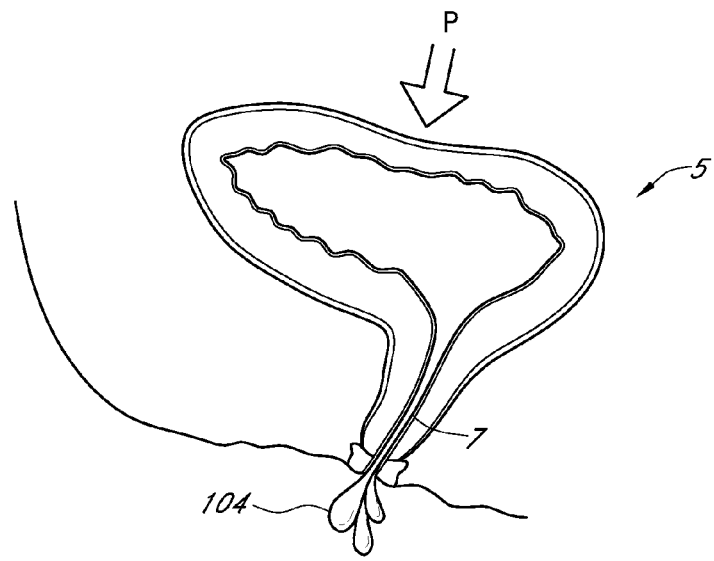
FIG. 32A illustrates a bladder experiencing pressure which causes urine leakage.
Figure 32B:
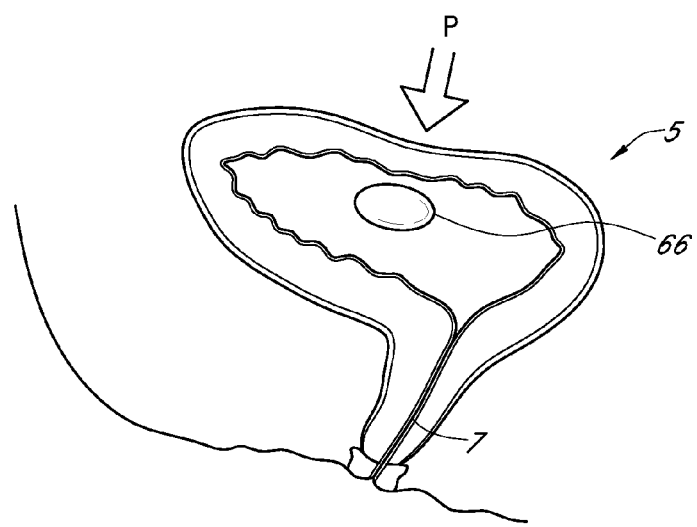
FIG. 32B shows the bladder of FIG. 32A with an implant that absorbs the pressure so that there is no urine leakage.

In one embodiment, an implant 66, such as a silicone balloon device, is placed in the bladder to attenuate pressure spikes that would otherwise cause urinary incontinence. As shown in FIGS. 32A and B, pressure "P" on the bladder, for example from physical activity can cause urine leakage 104 in those who suffer from urinary incontinence. The implant 66 can absorb the pressure in the bladder so that there is no urine leakage.

The pressure within the bladder is typically a little bit higher than atmospheric pressure, since it typically contains urine which displaces the bladder's muscular walls. The walls of the bladder, through their muscle tone and mass, exert force on the urine inside, resulting in typical pressures that can be around 15 cm $H_2O$ above atmospheric in some patients. For the sake of simplifying discussion in this document, we will simply use this number as an approximation of average bladder pressure. If the silicone balloon is under-filled with air such that there is no skin pressure to consider, then there will be a situation immediately before the balloon is placed in the bladder where the pressure within the bladder is atmospheric plus 15 cm $H_2O$, and the pressure within the balloon is atmospheric pressure. When the balloon is placed within the bladder, the balloon will instantaneously compress, so that its contents are at the same total pressure as the hydraulic pressure with which the urine in the bladder is pressing on the balloon. That is, the now slightly compressed gas will press outwards on the walls of the balloon with the same force that the liquid in the bladder will push inwards. This "force equilibrium" of exactly equal and opposite forces exerted from within the balloon outwards, and outside the balloon inwards is one equilibrium that should be considered in this example.

In the force equilibrium, the liquid or hydraulic pressure within the bladder pushes on the balloon, and the now slightly compressed gas within the balloon pushes outwards on the liquid. The inwardly pushing forces should balance with the outwardly pushing forces or the balloon will either burst or collapse.

The second equilibrium to be considered is partial pressure equilibrium. The partial pressures of the individual gas constituents within the balloon will seek to equilibrate with the gas tensions of the dissolved gas in the liquid outside the balloon.

In this example, first assume that initially, before the balloon was inserted, that the proportions of gas in atmospheric air were in the balloon, and that the same proportions of dissolved gas existed in the urine. The balloon was compressed slightly when it was inserted, so all of the partial pressures of the gas constituents increased by an amount proportional to the decrease in volume due to the compression. This results in a situation where there will be higher partial pressures of the individual gas components inside the balloon versus the gas tensions of the same gases outside the balloon. This will result in diffusion of these gases out of the balloon into the urine. As the gases leave the balloon, the balloon will shrink to maintain the force balance. In this example, this net out-of-the-balloon gas diffusion will continue until the balloon is completely empty. The rate of deflation will be a function of the permeability of the membrane to the gases held within and the difference between the hydrostatic pressure in the bladder and the total gas tension of gases dissolved in the urine.

In one aspect of this disclosure an important step is the addition of PFC to the contents of the balloon. Since some selected or preferred PFCs have high vapor pressures, the partial pressure of the PFC will add to the existing partial pressures of the other gases to increase the overall gas pressure in the device. A small amount of liquid PFC within the balloon serves as a reservoir or generator and will offset losses due to slow diffusion and maintain a constant PFC partial pressure.

Figure 33:
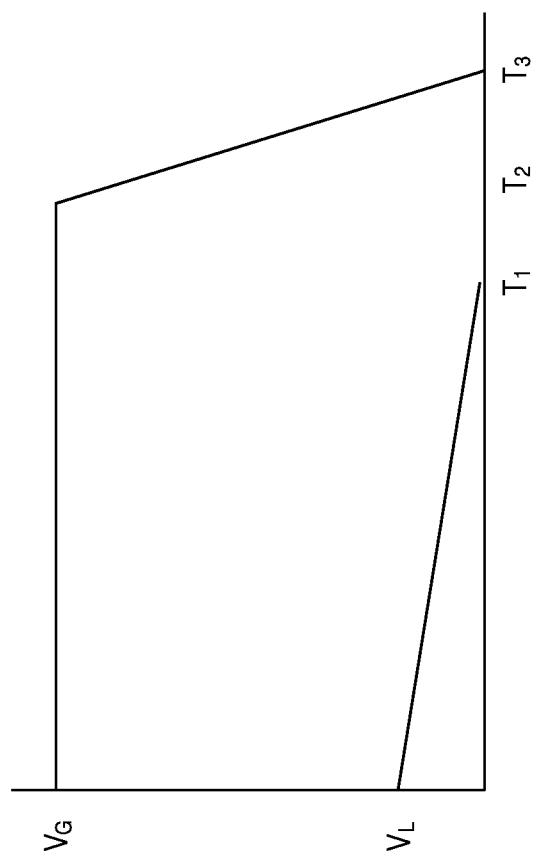
FIG. 33 is a chart of the gas and fluid volumes over time of a recharging implant.

FIG. 33 illustrates this generator system. The volume of the gas ($V_G$) remains constant as long as there is a volume of liquid PFC ($V_L$) within the balloon. The liquid PFC recharges the volume of gas through vaporization. Even after all the liquid has vaporized, the volume of gas remains at a constant volume until a time $T_2$ where the gas tension begins to be insufficient to maintain the volume $V_G$.

The total pressure in the balloon will be the sum of the partial pressures of its components, as described by Dalton's law. Due to the "force" equilibrium, in this case, the balloon will now expand or contract until the total pressure within the balloon balances the forces due to the hydraulic pressure outside the balloon. If the pressure external to the balloon is 15 cm $H_2O$ higher than atmospheric pressure and the vapor pressure of the PFC is 120 cm $H_2O$, assuming the PFC achieves its vapor pressure equilibrium instantaneously, it would seem that the balloon would have a pressure of 105 cm $H_2O$ higher than outside the balloon, which is impossible. What will actually occur is that the balloon will expand by a volume proportional to this pressure deficit to satisfy the force equilibrium. The now expanded balloon will now have partial pressure deficits for its gas components. This will result in the inward diffusion of gas to satisfy the gas partial pressure equilibrium. As the gas comes into the balloon, the balloon will expand slightly to maintain the force equilibrium, until a fairly static situation is achieved. This situation will be characterized by a stable volume balloon, containing liquid and gas PFC, and gas components whose partial pressures match the respective gas tensions of the gases dissolved in the urine. This stable balloon volume will occur if the difference between the total gas tension of the urine and the absolute hydrostatic pressure in the bladder approximately equals the PFC vapor pressure.

This example neglected the effect of the skin tension exerted by the balloon as it expanded. This would simply result in one additional additive factor for the force balance equation. In this case, the balloon's expansion would be limited by the inward force exerted by the wall of the balloon as it stretches.

The stable size of the balloon depends on the maintenance of a supply of liquid PFC inside the balloon, the balance of force as regulated by balloon size, and the balance of partial pressures. If any of these key factors moves out of balance the balloon will either grow or shrink.

Selection and Determination of the Vapor Pressure or Partial Pressure PFC Element In a simplified embodiment involving an air-filled balloon placed into the bladder or other liquid filled bodily organ one will note that the device will float in the bladder and rest near the top of the bladder. It will not deflate; therefore there is equilibrium between the air inside the balloon and the liquid pressing upon it. The gas molecules inside the balloon provide an internal force ($F_{int}$) that presses outwards, and the hydraulic pressure of the urine provides an external force ($F_{ext}$) that presses inward on the balloon. For the balloon to exist, the forces should be in balance as illustrated here, that is $F_{int}=F_{ext}$. The internal force is created by the pressure of the gas inside the balloon.

In this example, the gas inside the balloon was normal atmospheric air, at sea level, when it was inserted. So its total pressure before insertion was approximately 760 mm Hg which is approximately equal to 1000 cm $H_2O$. This total pressure of 1000 cm $H_2O$ is, as described by Dalton's law, equal to the sum of the partial pressures of its gas components. Normal atmospheric air is comprised of approximately 78% nitrogen, 21% oxygen, and 1% other gases. Since the total pressure is 1000 cm $H_2O$, we can surmise that the partial pressure of nitrogen or $P_{N2}$ is equal to 780 cm $H_2O$, the partial pressure of oxygen or $P_{O2}$ is roughly 210 cm $H_2O$, and the partial pressure of other gases or $P_{OG}$ is 10 cm $H_2O$. The partial pressures and total pressure of the balloon outside the bladder are shown in Table 2.

TABLE 2

Internal Balloon Pressure When Outside the Bladder

|   | | |
|---|---|---|
| | $P_{N2} =$ | 780 cm $H_2O$ |
| | $P_{O2} =$ | 210 cm $H_2O$ |
| + | $P_{OG} =$ | 10 cm $H_2O$ |
| | Balloon total pressure = | 1000 cm $H_2O$ |

As soon as the balloon is inserted into a urine filled bladder or organ, it will be subjected to hydraulic pressure due to the muscle tone of the abdomen and bladder pressing on the urine within. This is a frequently measured physiological parameter, and 15 cm $H_2O$ is a typical value, so we will use this in our example. Now, the patient into whom the balloon has been inserted is residing at sea level, so this "inside the bladder" (or intravesical) pressure is equal to the sum of atmospheric pressure plus the 15 cm $H_2O$, or 1015 cm $H_2O$. This means that in order to satisfy the force equilibrium, the total pressure inside the balloon changes so that it equals 1015 cm $H_2O$ also. It does this by compressing and getting smaller. The balloon will instantaneously compress as it is inserted into the bladder. According to Boyle's law, the pressure and volume of a gas are directly proportional according to the relationship: $P_1V_1 = P_2V_2$. This means that in order for the gases' volume to decrease, its pressure increases, in this case by 15 cm $H_2O$ or by 1.5%.

The total pressure of the gas inside the balloon has now changed, due to the compression, but the molar quantities and proportions of the gases within has not changed. Table 3 shows the partial pressures and total pressure of the balloon inside the bladder are (with rounding).

TABLE 3

Internal Balloon Pressure When Inside the Bladder

|   | | | |
|---|---|---|---|
| | $P_{N2} =$ | 780 + 1.5% = | 792 cm $H_2O$ |
| | $P_{O2} =$ | 210 + 1.5% = | 213 cm $H_2O$ |
| + | $P_{OG} =$ | 10 + 1.5% = | 10 cm $H_2O$ |
| | Balloon total pressure = | | 1015 cm $H_2O$ |

In this example, gas diffusion equilibrium should also be considered. Urine in the body, like other body fluids, contains dissolved gas. The amount of gas dissolved in these fluids is governed by the gases' solubility in the fluid, and whether or not it reacts chemically or biologically with the fluid. For example, blood can contain a much higher percentage of oxygen than water, due to the fact that the oxygen is bound to the hemoglobin in red blood cells. The gas tensions of gases in urine will be different than the partial pressures of gases found in atmospheric air (most likely lower). The gas tensions will also not be governed by the hydraulic pressure of the fluid, since these fluids are, relative to gas, incompressible and hydraulic pressure does not affect their solubility.

In an embodiment wherein the balloon is constructed of a material that is permeable to gas, the gas will seek to diffuse from the high partial pressures in the balloon into the liquid where the gas tensions are lower. For example, consider the fact that the partial pressure of oxygen in bladder urine could be around 84 cm $H_2O$ (as described previously) and in this example, the partial pressure of oxygen is 213 cm $H_2O$ in the balloon. This gradient will result in oxygen exiting the balloon at a rate determined by the gas permeability of the wall of the balloon. As the oxygen exits, the balloon will shrink to maintain the force equilibrium. This exiting of oxygen, and balloon shrinkage will be echoed by nitrogen and the other gases present, although at varying rates. The end result will be complete deflation of the balloon over time.

A means to maintain balloon inflation, as described above, is to provide a supply of liquid PFC inside the balloon. The liquid PFC will rapidly vaporize, and provide a supply of PFC gas whose partial pressure is "locked" at the vapor pressure of the PFC. This PFC will not diffuse out of the balloon as it is not soluble in water or urine. Let's consider a balloon containing a PFC whose partial pressure is 120 cm $H_2O$, plus normal air, inserted into the bladder as before. Table 4 shows the partial pressures, if the balloon was hypothetically filled outside the bladder at atmospheric pressure, before the PFC has a chance to vaporize.

TABLE 4

Internal Balloon Pressure Before Vaporization

|   | | |
|---|---|---|
| | $P_{N2} =$ | 780 cm $H_2O$ |
| | $P_{O2} =$ | 210 cm $H_2O$ |
| | $P_{OG} =$ | 10 cm $H_2O$ |
| + | $P_{PFC} =$ | 0 cm $H_2O$ |
| | Balloon total pressure = | 1000 cm $H_2O$ |

In this example, outside the bladder situation, as the PFC vaporizes, the balloon will expand to maintain the force equilibrium. The gas quantities and proportions other than the PFC will remain constant, so they are, in effect, diluted by the PFC whose partial pressure will be fixed at its vapor pressure of 120 cm $H_2O$. Thus, moments later, the partial pressures in the now expanded balloon will be as shown in Table 5. The balloon will have expanded 12%, the partial pressures of the constituent gases other than PFC will maintain their proportions since the moles of gas are the same; however they will reduce proportionally as shown:

TABLE 5

Internal Balloon Pressure After Vaporization

|   | | |
|---|---|---|
| | $P_{N2} =$ | 686 cm $H_2O$ |
| | $P_{O2} =$ | 185 cm $H_2O$ |
| | $P_{OG} =$ | 9 cm $H_2O$ |
| + | $P_{PFC} =$ | 120 cm $H_2O$ |
| | Balloon total pressure = | 1000 cm $H_2O$ |

If this balloon is placed into the bladder, then the bladder pressure, 15 cm $H_2O$, should equilibrate to a new total pressure of 1015 cm $H_2O$ as before. The balloon will shrink by 1.5% and the new partial pressures are shown approximately in Table 6.

TABLE 6

Internal Balloon Pressure After Vaporization When Inside the Bladder

| | |
|---|---|
| $P_{N2}=$ | 697 cm $H_2O$ |
| $P_{O2}=$ | 189 cm $H_2O$ |
| $P_{OG}=$ | 9 cm $H_2O$ |
| + $P_{PFC}=$ | 120 cm $H_2O$ |
| Balloon total pressure = | 1015 cm $H_2O$ |

If the gas tension of dissolved gas in the urine is lower than the new partial pressures in the balloon, gas will be driven out of the balloon at a rate which is regulated by the gas permeability of the balloon, and the balloon will shrink. If the partial pressure of the dissolved gas in the urine is higher than these new partial pressures, then gas will be drawn into the balloon at a rate which is regulated by the gas permeability of the balloon, and the balloon will grow. However, the partial pressure of the PFC will remain fixed. Note that for simplicity, this example excluded the impact of the skin tension of the balloon. The next example will consider skin tension.

The partial pressure of the PFC can be selected by tuning its vapor pressure. In order to maintain a balloon whose volume is stable, the PFC should be selected so that a diffusion balance is maintained. The formula can be derived as follows. First, the pressure inside the balloon equals the pressure outside the balloon, or else the balloon will collapse or burst.

$$P_{Inside\ Balloon} = P_{Bladder-avg} + P_{Skin-tension} \quad (1)$$

As discussed infra, $P_{Inside\ Balloon}$ (the pressure inside the balloon) is equal to the sum of the partial pressures of the gases within the balloon. As shown here, it is also equal to the hydraulic pressure pushing upon it plus the pressure due to the balloon skin. The term, $P_{Bladder-avg}$, comprises the hydraulic pressure pushing upon the balloon due to abdominal pressure, bladder muscle tension and other factors. The skin pressure, $P_{Skin-tension}$, is the inward force exerted by the stretching material of a balloon's walls, or in other cases, simply the weight exerted on the gas within by a flaccid under inflated balloon. This equation is simply another version of the "force equilibrium" equation described earlier.

At the same time, recall that the total pressure within the balloon is equal to the sum of the partial pressures of the gases it contains:

Note: All pressures below are absolute pressures $$P_{Inside\ Balloon} = P_{N2-balloon} + P_{O2-balloon} + P_{other\ gases-balloon} + P_{PFC} \quad (2)$$

Since the partial pressure of the other gases is only 1% of the sum of all the non PFC gases, this can be approximated as being zero, so:

$$P_{Inside\ Balloon} = P_{N2-balloon} + P_{O2-balloon} + P_{PFC} \quad (3)$$

Equation (1) from the force equilibrium was as follows:

$$P_{Inside\ Balloon} = P_{Bladder-avg} + P_{Skin-tension} \quad (1)$$

Therefore combining equations (1) and (3) gives:

$$P_{Bladder-avg} + P_{Skin-tension} = P_{N2-balloon} + P_{O2-balloon} + P_{PFC} \quad (4)$$

Over time, gas diffusion will occur, and $P_{N2-balloon}$ and $P_{O2-balloon}$ will equilibrate to values that approximate the partial pressures of oxygen and nitrogen dissolved in the urine (their gas tensions). Therefore:

$$P_{N2-balloon} + P_{O2-balloon} = P_{Dissolved\ gas} \quad (6)$$

And by combing (4) and (6) we get:

$$P_{Bladder-avg} + P_{Skin-tension} = P_{Dissolved\ gas} + P_{PFC} \quad (7)$$

Or $$P_{PFC} = P_{Bladder-avg} + P_{Skin-tension} - P_{Dissolved\ gas} \quad (8)$$

Where:
$P_{PFC}$=The desired vapor pressure of the PFC.
$P_{Bladder-avg}$=The average bladder pressure over time (i.e. course of a day) or more generally, the anatomical environment/hydrostatic average.
$P_{dissolved-gases}$=The total gas tension of bladder urine.
$P_{skin\ tension}$=The inward force exerted by the skin of the balloon.

More generally, the equation for selecting a PFC suitable for maintaining a pressurized device according to one or more aspects of the disclosure in a given anatomical environment is:

$$P_{PFC} = P_{anatomical\ environment/hydrostatic-avg} + P_{Skin-tension} - P_{Dissolved\ gas} \quad (9)$$

In another embodiment the selection for the high vapor pressure element can be described as:

$$\text{atmospheric pressure} + P_{pfc} = \text{external pressure or loads on implant} \quad (10)$$

Where the external loads include: tension generated by skin of the balloon, normal somatic pressure during fill and void of organ (if applicable), transient somatic pressure, e.g. abdominal, patient generated Valsalva, bodily weight on organ e.g. abdominal weight on bladder or on bladder wall/balloon when the bladder is empty, differential between gas tensions in body fluid and partial pressures within balloon.

Having shown how to determine an appropriate vapor pressure for the PFC element, one can now select an appropriate mixture of PFCs to approximate this value. The $P_{PFC}$ can be selected by mixing PFCs of different vapor pressures, and calculating the composite vapor pressure based on the proportions of the moles of the individual PFCs.

One consideration is the average pressure within the desired area of the body ($P_{anatomical\ environment/hydrostatic-avg}$). In the example of a device implanted in the bladder, the average pressure within the area of the body would be a time average of the pressure in the bladder ($P_{Bladder-avg}$). This would encompass the average of: the low pressure of slowly filling bladder; pressure spikes from events such as laughs, coughs or sneezes; higher pressures achieved during micturition, or during Valsalva. Other hollow organs and tissue sites would similarly vary in pressure ranges, from which an average value could be calculated.

Another consideration is the total gas tension of the bodily fluid in the particular area of the body ($P_{Dissolved\ gas}$) to be treated. This includes all the dissolved gases in the bodily fluid such as oxygen, nitrogen, carbon dioxide, or other gases. In the bladder, the bodily fluid is urine. The total gas tension in urine can vary based on the patient's diet, presence of substances in the urine that bind oxygen or other gases, or the gases that the patient is inhaling. For example, a patient breathing pure oxygen would have a higher oxygen gas tension. It is also worth noting that gas tension will almost always be less than the hydrostatic, anatomical pressure, or bladder/organ/implantation site pressure. Also note that the driving force for deflation is that the concentration of gases inside the device is higher than the total gas tension outside the device.

Several of these parameters will vary from patient to patient. For example, average bladder pressure in men is generally higher than that of women. Average bladder pressure can vary from person to person within a gender based on how full each individual lets their bladder get before voiding.

Also, average bladder pressure may vary due to pathology, for example, due to a condition known as detrusor instability which causes undesired contractions of the bladder's muscular walls. Bladder pressure can also vary due to physical activity. One would expect that the average bladder pressure of a weight lifter would be higher during a weight lifting competition than it is for a sedentary individual. As mentioned above, the bladder gas tensions can vary based on diet, lung function, metabolic rate and other factors.

An additional consideration is the skin tension of the balloon. The skin tension of the balloon can vary based on many factors, including the material of the balloon, the thickness of the material, and its means of construction. It can also vary based on how "stretched" it is. For example, a balloon that has a volume of 3 ml when empty and is filled with 15 ml will be much more stretched than the same balloon filled to 5 ml.

It is conceivable that a balloon that has a stable volume over time could be created by measuring each of the above parameters and selecting the PFC based on that. Also, an individual could be "titrated" so that various PFCs are tried and one that is stable over time is selected. A combination of the two methods could be used as well—for example, gross measurement of physical parameters followed by "trying" PFCs of different partial pressures.

Various means could be used to achieve this measurement and/or titration. For example, a pressure sensor that resides in the bladder and either transmits data out of the bladder telemetrically, or stores it for later retrieval, could be used to determine average bladder pressure. Pressure information of other hollow organs such as the eye, heart, cranium, lungs, stomach, liver, gal bladder etc. or bodily sites could similarly be obtained. Sensors, such as those used for blood gas measurement could be used to measure the total gas tension of urine in the bladder and the individual tensions of the constituent gases. Finally, balloons can be selected or filled in order to achieve a desired skin tension. Test device involving balloons with strain gauges and pressure gauges to record or transmit data for short time could also be used to determine pressures and skin tension values.

Two examples of how the gas pressures in urine could be measured include the use of a blood gas analyzer, such as those available from Radiometer America Inc. or the MRI approach described by Zaharchuk et al., referenced above.

A blood gas analyzer can be used to sample gases in the urine. A patient's bladder would be allowed to fill normally. A catheter or tube would be inserted into the patient's bladder. Urine would be extracted into a syringe or vial. The vial would be inserted into the machine, and standard readouts can be obtained. $PO_2$ (partial pressure of oxygen in the sample) is an example.

The blood gas analyzer runs the risk of inaccuracies related to how quickly the measurement is performed. The sample can become contaminated in the time between taking the sample and sending to the lab. Also, the measurement may not be as accurate as needed since there is measurement error in the machine. A difference of 10 cm $H_2O$ can be enough to make the difference with regard to a balloon inflating or deflating thus, these inaccuracies can be make the error too great to be useful.

Concerning MRIs, MRI machines are big, and expensive. Thus, it is not practical to place every patient inside an MRI machine. Furthermore the accuracy of the method ranges from +/−14 mm Hg to +/−46 mm Hg. 14 mm Hg corresponds to +/−18.6 cm $H_2O$, too broad a range for most applications described herein.

A preferred method is to "titrate" the PFC. First, based on the information described herein the Physician can estimate the relative gas partial pressures in urine and the needed partial pressure of the PFC. For example, the estimate can be in the range of 100 to 130 cm $H_2O$. A clinical study can be performed in which a series of patients are studied using balloons containing PFC with a partial pressure of 110 cm $H_2O$. The state of these patient's balloons upon removal would be monitored carefully. One possible result is that on average the balloons could be decreasing slightly in size over a 3 month period. Continuing the example, another series of patients could be studied using a PFC with a vapor pressure of 120 cm $H_2O$. Upon examining their balloons after 3 months, one possible result is that their balloons could be growing slightly in size over 3 months. This result would tell us that the ideal vapor pressure would be in between 110 and 120 cm $H_2O$. The next step would be to try a series of patients with a vapor pressure of 115, and so on.

One reason that the titration method is preferred is that the desired outcome is the best partial pressure on average over time. The partial pressure of oxygen in urine, for example, will change over the course of the day. It is likely to be different during sleeping and waking hours. It can also be affected by diet, for example, eating foods rich in ascorbic acid (vitamin C) can affect oxygen partial pressure. The titration method yields the value that is optimum for the long term successful inflation of the balloon. Other methods that provide an instantaneous measurement (such as blood gas monitors or MRI) would not provide this benefit. It would be impractical to make such measurements many times over the course of a day, days, or even weeks or months.

Setting the Vapor Pressure of the Selected PFC Element

The PFC vapor pressure of the PFC element or additive can be set by choosing the molecular weight/number of carbons and isomer form of the PFC (rings, branched, linear) or using hetero-atoms such as Br or H. These pure compounds will have a constant vapor pressure throughout the life of the device as it very slowly looses PFC through the aqueous fluid surrounding the device.

Intermediate vapor pressures can also be produced by using mixtures of PFCs, though these mixtures will change component ratios after initial vaporization and slowly through the life of the device. If mixtures are used, an excess quantity of PFC should be put in the device to minimize the vapor pressure changes (unless we want the vapor pressure and thus inflation pressure to slowly decrease). The vapor pressure of a liquid mixture can be predicted by Raoult's Law where the total vapor pressure is the sum of each component PFC vapor pressure times its mole fraction in the liquid. This means the most volatile component leaves faster and the vapor pressure of the remaining PFC mixture slowly drifts toward the vapor pressure of the least volatile component in the mixture. This effect is exacerbated as the higher vapor pressure PFCs also are in general lower in molecular weigh so they also diffuse faster and have higher water solubilities.

Examples of PFCs suitable for use in various implants described herein include: perfluoropropane, perfluorobutane, perfluoropentane, perfluorohexane, perfluoroheptane, perfluorooctane, perfluorononane, perfluorodecane, perfluorooctylbromide, perflubron, and perfluorodecylbromide. As explained above, two or more PFCs can be combined to form a liquid mixture with a particular vapor pressure according to their mole fraction in the liquid. A preferred range of vapor pressures for a PFC element in one or more embodiments is around 50-200 cm $H_2O$. In other embodiments the preferred range of selected vapor pressures for a PFC element is around 100-150 cm $H_2O$. In other embodiments, for example in the bladder, the preferred range of selected vapor pressures for a PFC element is around 115-130 cm $H_2O$, around 120 cm $H_2O$ or around 115-117 cm $H_2O$. For example, in one embodiment a mixture of about 0.5 mole perfluorooctane and about 0.5 mole perfluoroheptane can result in a vapor pressure of between around 115 and 130 cm $H_2O$ at 37° C. In another example, a mixture of 0.545 mole perfluorooctane and 0.455 mole perfluoroheptane can result in a vapor pressure of about 120 cm $H_2O$. The preferred range of selected vapor pressures for a PFC element can be based in part on $pO_2$ of the anatomical structure. Thus, for example, areas of the body with a $pO_2$ similar to that of the bladder can also use a similar PFC pressure range. As $pO_2$ increases the desired PFC vapor pressure range decreases.

Volumes of the PFC element are generally limited by the volume of the organ or tissue site in which the implant containing the PFC element is implanted and by the duration in which the pressurization is intended to be maintained. A preferred range of volumes for a PFC element within an implant according to one or more embodiments is around 0.1-10 ml and more preferably around 0.2-0.6 ml in certain applications involving the eye or the bladder. Total volumes of implants such a balloons or cells according to one or more embodiments can vary from 0.1 ml to 1.0 L.

The preferred volume for an implant will vary based on a variety of factors. The following example demonstrates some of the considerations for the total volume of an implant in a particular application. A pressurized implant is added to the bladder in order to attenuate pressure pulses in the bladder associated with stress urinary incontinence leakage. The clinical efficacy (preventing leakage) is increased by increasing the volume of the implant. In testing, it has been determined that efficacy increases proportionally to size.

The functional capacity of a typical urinary bladder is commonly in the range of 200 to 300 ml. This depends on many characteristics such as gender, age, health status, etc. If the implant is too large it will impact the bladder's ability to perform its primary function of storing urine. "Residual volume" is a parameter that is commonly measured by urologists and it describes the measured quantity of urine remaining in a patient's bladder after they have completed voiding (i.e. they think they are empty). Based on the experience of urologists it has been determined that a balloon as large as 30 to 40 ml will not likely be noticed by patients, specifically with regard to increasing their frequency of urination. Thus, a preferred balloon volume for the bladder is between 20 and 30 ml.

Selection of a PFC and Enclosure Skin Tension System

As discussed supra, one equation for the desired PFC vapor pressure is:

$$P_{PFC} = P_{anatomical\ environment/hydrostatic\ avg} + P_{Skin-tension} - P_{Dissolved\ gas} \quad (9)$$

It is possible that a skin tension and PFC could be chosen so that the two associated parameters for these characteristics are much, much larger than the other two parameters (for example between 5 and 20 times and preferably 10 times). For example in the bladder, if $P_{Bladder-average}$ is on the order of 15 cm $H_2O$ above atmospheric pressure, or about 1015 cm $H_2O$ absolute pressure; $P_{dissolved-gases}$ is on the order of 880 cm $H_2O$; then a balloon could be selected so that its skin tension pressure is 10,000 cm $H_2O$ or greater, and a PFC could be chosen with a vapor pressure that is approximately the same amount. Then, in theory, a system could be designed that is relatively independent of the average anatomical environment pressure, here bladder pressure, and independent of the gas tension of dissolved gases. This is because, in this example, $P_{PFC}$ and $P_{skin-tension}$ are approximately equal, and much larger than the other two terms. Similarly, devices used in other anatomical environments and applications such as ophthalmic, vascular, cardio-vascular, renal, pulmonary, intracranial, etc., could be designed with similarly appropriate and corresponding skin tension and $P_{PFC}$ values.

Implant Compliance

An objective of certain devices according to one or more aspects of the disclosure is to supply compliance, dV/dP or a maximum change in volume with an elevation of pressure ($P_h$, hydrostatic pressure). The presence of an elastic skin only slightly reduces the compliance of the device. Since the compliance (dV/dP) of a gas obeying Boyle's law, $P_1/P_2 = V_2/V_1$, is inversely proportional to the absolute pressure of the gas inside the device ($P_g$); as long as the added skin pressure ($P_{skin}$) is significantly less than one atmosphere (760 mm Hg, 1,033 cm $H_2O$), the compliance of the gas is only slightly reduced with an elastic skin (a skin pressure of 5% of an atm, 50 cm $H_2O$, has 95% of the dV/dP of gas without a skin).

The other cause for a reduction in compliance is that, as the device volume reduces under an external pressure increase, the pressure caused by the skin goes down, relieving some of the added pressure and reducing some of the volume change. This effect is controlled by the slope of the volume vs. pressure curve (V/P curve) of the device, which in turn is determined by the skin materials and geometry. In the case of an inelastic bag, the V/P curve starts at zero pressure at zero volume and then jumps vertically to the volume when the bag is full (a full inelastic bag does not stretch with more gas pressure inside) for any measurable pressure. This bag has no compliance at pressures that completely fill it, as the slope of the V/P curve is zero. On the other hand, a skin that is very stretchy/elastic (e.g. thin silicone) has a very gradual change in skin pressure as the volume changes (can be designed to have a large V/P slope at the operating volume) and only slightly reduces the device compliance. The small magnitudes of these effects are seen in a toy latex balloon that changes diameter/volume nearly as much as a free gas when the barometric pressure or altitude is changed.

The above compliance reducing effects of the skin are reduced and in some cases overcome by the compliance increasing effects of the presence of PFC vapors, e.g. their ability to condense when compressed.

The vapor pressure of the PFC may be chosen to inflate the device at equilibrium to a volume where the V/P curve of the device has a very large positive slope or in other cases just below where the slope decreases, thereby limiting maximum volume.

The V/P curve of a device can be calculated from the known elastic properties of the material (stress/strain relationship) and mechanical principles (the law of Laplace, $P_{skin} = 2$ times the skin tension over device radius). In many cases it may be better to measure the V/P curve of a device by inflating it with any fluid (e.g. air or air plus PFC) and then adjusting it. The device V/P curve can be adjusted, for example, by lowering the V/P slope using a thicker or stiffer skin material. Modifying the geometry of the device can also adjust the curve, e.g. the 1/radius law above means that a long small radius cylinder will have a shallower, lower slope V/P curve than a sphere of the same volume.

Figure 34A:
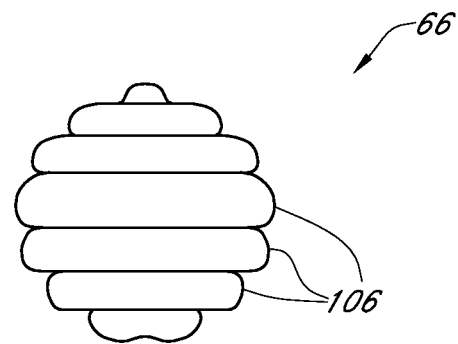
FIG. 34A shows a side view of a corrugated implant with ridges in an unexpanded position.
Figure 34B:
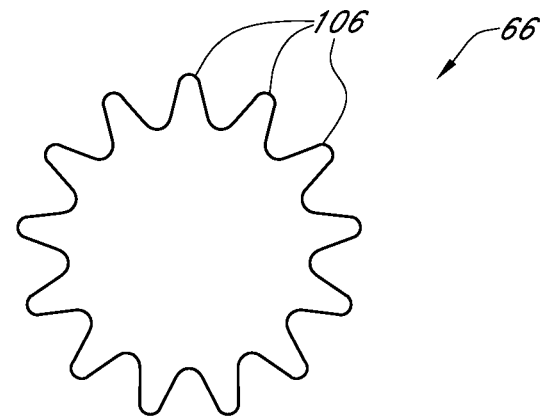
FIG. 34B shows the cross-section of the implant from FIG. 34A in the expanded position.

The V/P curves of the various devices described herein can be modified in many ways using unique geometry, so that even essentially inelastic materials can have an elastic V/P curve. FIGS. 34A-35D illustrate features of implants 66 including various skin geometries which affect the V/P curve of the implant. In certain embodiments, sinusoidal oscillations in the device surface or dimples (positive or negative) like a golf ball, turn flexing moduli into elongation of the shape. FIG. 34A shows a side view of a corrugated implant 66 with ridges 106 that initially provide little resistance to expansion but upon full inflation straighten out and form a smooth inelastic surface resisting further expansion. FIG. 34B shows the cross-section of the expanded implant 66. In other embodiments, coiled cylinders or clusters of small spheres vs. single spheres are utilized to reduce inflation radius. Other embodiments, such as a relatively flat envelope, may comprise turning flexing moduli into thickening of the shape.

Figure 35A:
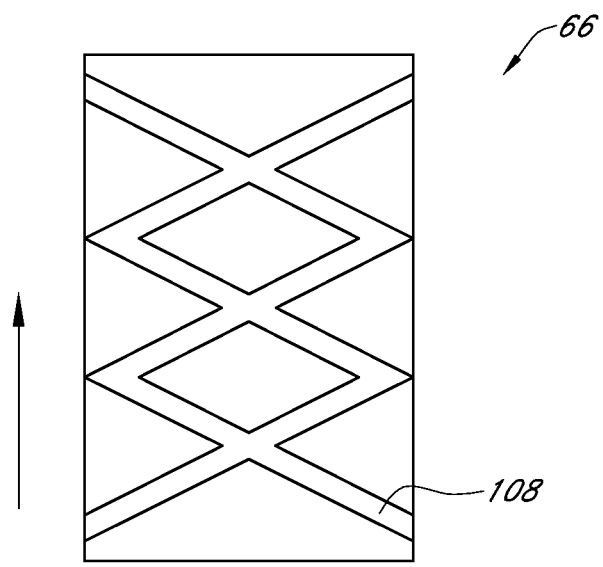
FIGS. 35A and B depict an implant with a frame including an "x" lattice.
Figure 35B:
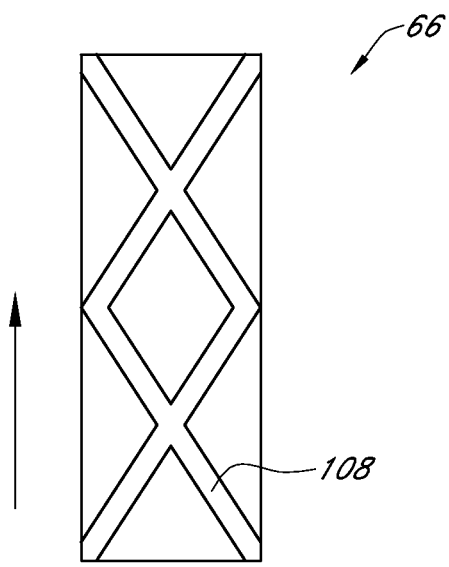
FIGS. 35C and D illustrate implants at least partially enclosed in an inelastic net.
Figure 35C:
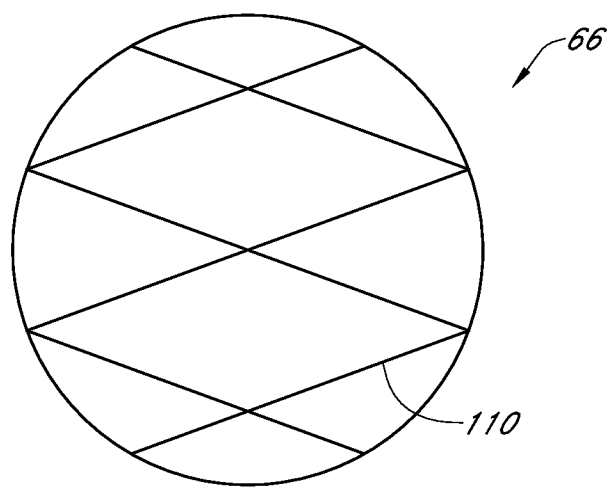
Figure 35D:
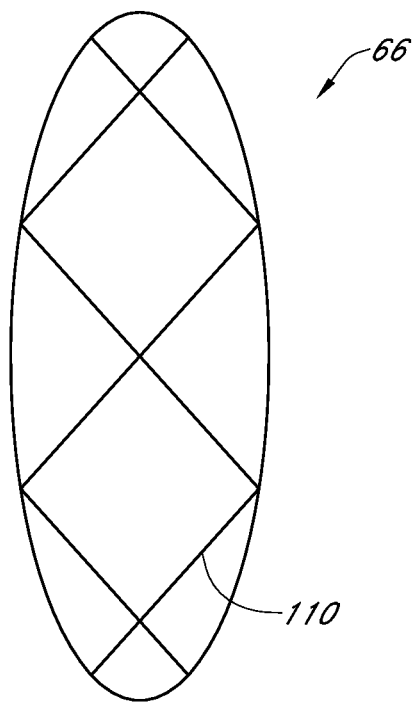

In some embodiments, cross ribs can be used to add stiffness to the V/P curve. FIGS. 35A and B depict an implant 66 with frame or "x" lattice 108 that can compress laterally and elongate vertically. Thus, in this embodiment the implant can initially form a flat disc or plate and then expand upwards as indicated by the arrows. As shown in FIGS. 35C and D, certain implants 66 can be at least partially enclosed in an inelastic net 110 to stop growth or steepen the V/P curve at a certain volume. The net 110 could be attached or unattached to the device. Inelastic chords could be included in other device shapes like in tires with chords. Alternatively, the net 110 can be a pattern formed of the same material as the implant 66 but of a different thickness.

Providing Skin Tension Bias to Sustain Implant Volume in Changing Pressure Environment Various embodiments of implants described herein comprise balloons, cells or enclosures comprising a porous vessel where internal gases and external gases dissolved in the body fluid interchange over time. Such balloons will tend to expand or contract as the result of an imbalance between the outside "loads" and the internal forces supporting the balloon. With correct PFC vapor pressure selection a small bias can be created where the balloon will grow until the tension in the polymer skin counteracts the bias of the PFC. The bias can be defined as the sum of all the partial pressures inside the balloon (PFC+air) minus the external sum of gas tensions or load in the surrounding environment. Turning to the equilibrium equation discussed previously, the PFC element in this embodiment should be greater than or equal to the other factors:

$$P_{PFC} \geq P_{anatomical\ environment/hydrostatic\ avg} + P_{Skin-tension} - P_{Dissolved\ gas} \qquad (11)$$

Figure 36:
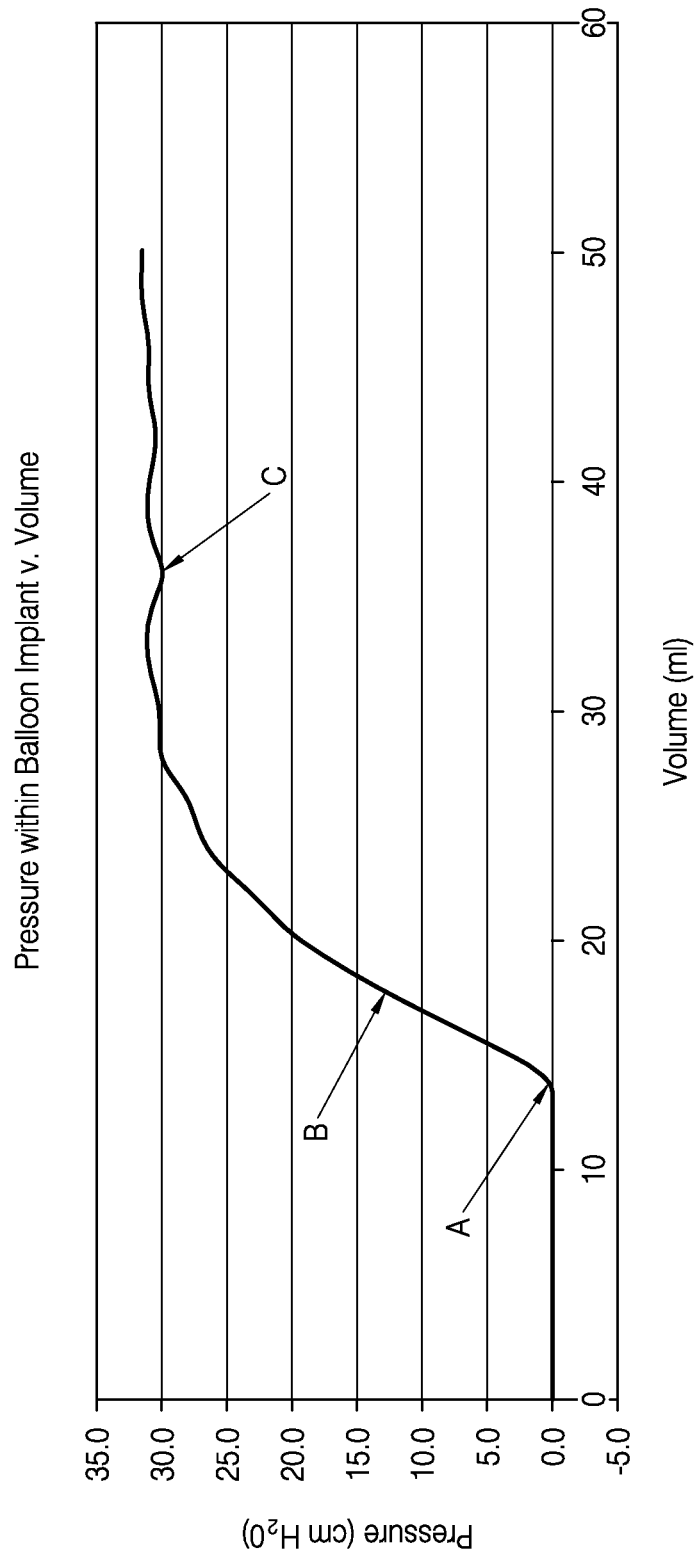
FIG. 36 charts the pressure within an implant verses the volume of the implant.

A balloon's internal pressure verses volume can be plotted as shown in FIG. 36. In the region from about 0 to 14 ml of volume, designated as up to "A", the "balloon" is essentially a bag of air with zero skin tension. At about 14 ml the bag becomes a balloon. Increasing amounts of volume put stress on the skin of the balloon and exert pressure on the internal gases (as in the region around "B"). Depending upon the balloon material and construction, this region of the graph showing the additional volume being gained will be fairly linear. This is analogous to the elastic region of a stress vs. strain curse, which will remain linear until either the elastic limit of the material is reached or the material fails.

As the volume increases, the balloon continues to stretch until the wall thickness decreases such that the balloon no longer exerts increasing levels of force on the internal gases. At this point the balloon continues to increase in size, however, the pressure inside the balloon levels off and eventually drops before the balloon fails. This area is designated with the letter "C". In balloons that yield, either due to molecular motion or thinning of the wall, this region of the graph can show slower growth or even diminishing pressure with added volume. The actual shape of the curve is material dependent. The shape shown, for example, is consistent with the behavior of silicone. Similar graphs can be made for other materials.

In the region before "A" and the region designated by "C" the balloon is unstable and tends to change volume as the result of gaseous interchange across the skin barrier. Balloon stability is created when a positive bias exits where the sum of the internal partial pressures is greater than the external gas tensions by an amount less than the height of the curve at "C", approximately 30 cm H$_2$O in this example. The positive bias will increase the balloon's volume until the skin tension increases the internal pressure to offset the bias. At this point the balloon will be stable. It would take more internal pressure than exists within the balloon to further increase in volume, and it is not able to shrink as the positive bias forces the balloon volume higher than the bag region (before "A").

In this way a balloon can be engineered to remain stable in volume (as opposed to completely shrinking or expanding until failure) over extended periods of time while experiencing changes in pressure. This can be done by selecting a PFC with a slight bias over the anticipated load but, counteracted by the skin tension profile of the balloon for that pressure range.

One method of controlling the size of an air and high vapor pressure media filled porous balloon insitu utilizes the skin tension in the balloon wall to offset a purposely created difference between the external load and the internal resistance. This would be unnecessary if it were possible to perfectly set the PFC vapor pressure to offset the external load. However, because the pressure in the bladder fluctuates and different patients have different average bladder pressures it can be useful for a device to have some tolerance to naturally occurring fluctuations and/or to be able to be used in different patients. By utilizing the skin tension in the manner prescribed here tolerance can be added to the naturally occurring variations in average external load on the balloon.

It has been shown that in the initial under-filled or "bag" region "A" of the curve or in the post-yield region "C", it is extremely difficult to control the balloon volume over time. In order to control the balloon volume over time in these regions, the PFC vapor pressure would have to be set precisely and the variation within and between patients would need to be very small. Conversely, by using the increasing pressure with volume nature of the "elastic" region "B" of the curve the balloon can find its own equilibrium and become stable in volume.

For example, if the average external load across a population were 100 cm H$_2$O and the average external load across the patient population varied from 90 to 110 cm H$_2$O then the PFC may be blended to yield a vapor pressure of 120 cm H$_2$O. Assuming the balloon is not initially over-filled, the balloon would gain volume by sucking dissolved gasses from the surrounding liquid environment. As the balloon increased in volume the pressure would go up due to the tension created in the balloon wall. This wall stress will offset the excess vapor pressure of the PFC blend and the balloon will stop growing and be at equilibrium.

Another advantage to designing the system to equalize on this part of the curve is that the balloon volume changes little with changes in the external load. This is because in order to offset small changes in external load a relatively large change in pressure is required.

The slope of the pressure vs. volume curve in this region is the result of the elastic modulus of the material and the geometry of the balloon. The acceptable limits of this curve are bounded by comfort and irritation which can be affected by high sloped (or stiff) balloons and poor volume control from balloons with low slopes in this region of the curve. Slopes of between 1 and 20 cm H$_2$O/ml of volume have been shown to provide bounds to these criteria. Slopes between 3 and 8 cm H$_2$O/ml of volume are preferred. As previously mentioned the slope can be designed into the balloon by the selection of material (elastic modulus) and geometry (shape and wall thickness).

Limiting Implant Expansion

In another embodiment two or more PFCs with different vapor pressures are mixed to give an average vapor pressure based on the mole fraction of the components. As the PFC mixture diffuses out of the device over time the more volatile component will diffuse proportionately to its mole fraction in the mix, therefore the mole fraction of the higher vapor pressure component will go down and the vapor pressure of the mix will likewise be reduced. This phenomenon could be used to control the ultimate size of the balloon. As the balloon expands, the vapor pressure of the PFC mix will go down placing an upper limit on balloon volume.

In some embodiments, the skin tension of the balloon could be used advantageously to limit balloon expansion. As the balloon expands, the tension of the balloon material will increase until the excess gas pressure in the balloon will be offset by the tension in the balloon skin.

Figure 37A:
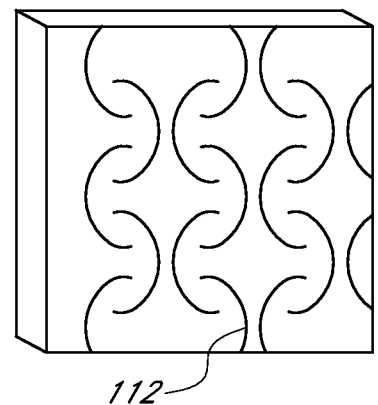
FIGS. 37A and B are detail views of implant membranes with curvilinear elements or interlocking elements that limit expansion along one or more axis.
Figure 37B:
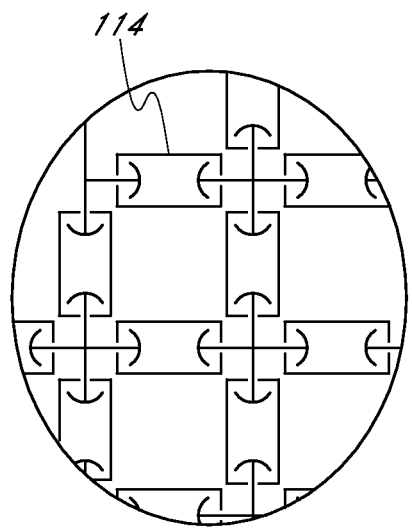

In addition, just as skin geometries and other features of the implant 66 can change the V/P curve; these same or similar features can limit expansion, deflation or the rate of change of the implant. The corrugated implant of FIGS. 34A and B can allow expansion with the disclosed ridges 106 and limit expansion with this same feature. The ridges 106 can initially provide little resistance to expansion but upon full inflation straighten out and form a smooth inelastic surface resisting further expansion. The frame or "x" lattice 108 and the net 110 of FIGS. 35A-B and 35C-D, respectively, can both be used to limit expansion of the implant 66. FIGS. 37A and B show additional features such as curvilinear elements 112 or interlocking elements 114 disposed on or within the membrane of an implant 66 operable to limit expansion along one or more axis.

In one embodiment, an implant has a high surface to volume ratio to affect a rapid rate of change. The implant shape can be selected from cylindrical, spiral, or ridged. In another embodiment a slow rebound or rapid inflation is desired and thus a low surface area to volume ratio is desired and a spherical design is selected.

In a further embodiment the quantity of PFC in a balloon could be used to limit expansion. A precise quantity of PFC could be added to the balloon such that as the balloon expands the PFC would volatilize to maintain its partial pressure until the PFC liquid reservoir is depleted. The PFC gas would then dilute with further expansion and the internal pressure of the balloon would be limited.

Devices described herein containing PFC and other gases can be placed into pressure equilibrium with the environment in which they are deployed. Since no natural environment is truly at constant pressure, the balloon system would need to gain external gases during low external pressure times and lose gas during high pressure times. The loss of gas would need to balance with the gain of gas for long term stability.

Controlled Expansion and Reduction

In another embodiment, a controlled expansion device is provided that is operable to expand or contract over time at a controlled rate. The rate can be controlled, for example, via selection of an enclosure with a suitable diffusion rate and selected PFC element for its vapor pressure properties. Unlike other embodiments, in this case the PFC element will have a significantly greater value than that selected for equilibrium, perhaps 1.5-10 times greater, thus the driving equation is as mentioned above:

$$P_{PFC} \geq P_{anatomical\ environment/hydrostatic\ avg} + P_{Skin-tension} - P_{Dissolved\ gas} \quad (11)$$

For example, in breast augmentation/reconstruction surgery, as explained below, it could be advantageous to place a small balloon at the future implantation site with the capability of expanding slowly over several days or weeks creating a pocket in the tissue. This could facilitate the placing of the implant with minimal discomfort or trauma to the surrounding tissue. In one embodiment, the device inflates to full or 100% volume in a period of a minute to a month. This concept could be applied to any implant procedure in which space needs to be made for the implant itself, or another implant or transplanted organ. Implants according to one or more embodiments could optionally include implanted electronic monitoring and regulating devices to monitor and control the expansion or contraction of such devices.

Figure 38A:
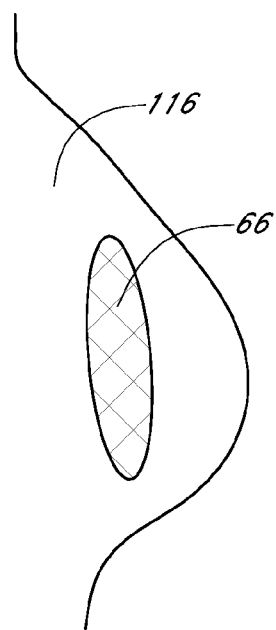
FIGS. 38A and B show cross-sectional side views of an implant within a breast.
Figure 38B:
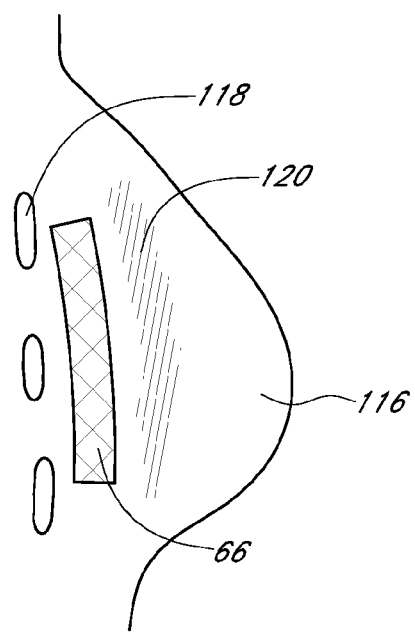

Illustrated in FIGS. 38A and B are breast augmentation or reconstruction implants and devices 66. The devices 66 can be used to create space for a different implant, such as a silicon gel or saline breast implant. In some embodiments, the device 66 can remain within the body, after creating, forming space, and/or stretching the surrounding tissue. In FIG. 38A, an inflatable implant 66 is placed within breast tissue 116. By charging the implant with a selected PFC element, the rate of expansion of the implant 66 can be gradual and controlled, thereby reducing stretch marks or other damage. FIG. 38B shows another embodiment in which an implant 66 is placed between the ribs 118 and muscle tissue 120 to create space for a different implant.

Figure 39:
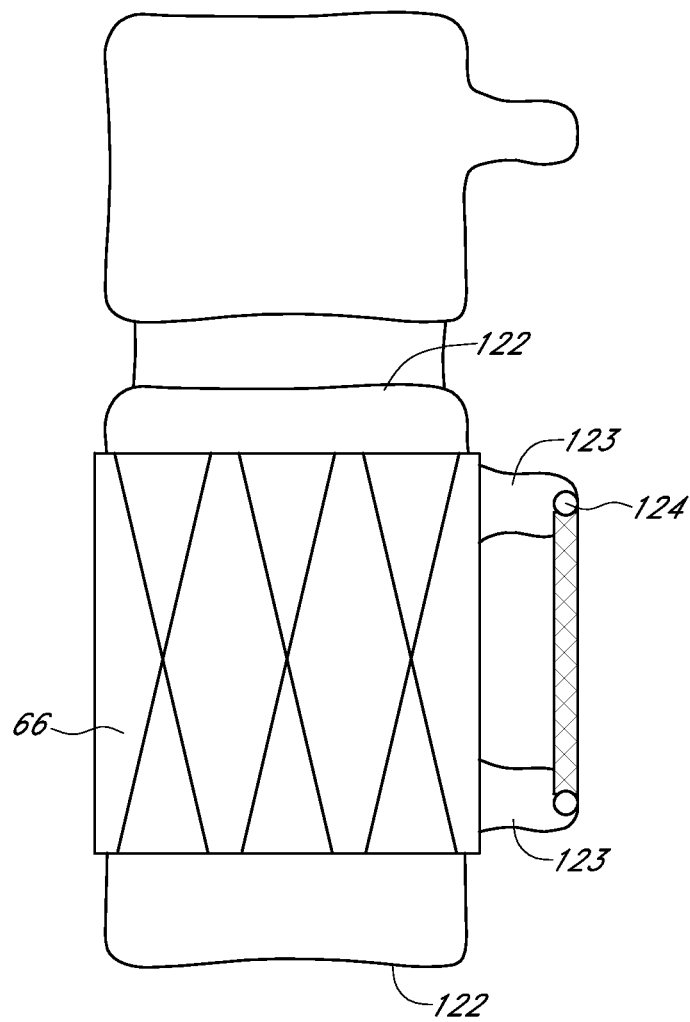
FIG. 39 is a side view of two vertebral bodies where one implant surrounds and connects the vertebral bodies and one implant is connected to opposing spinous processes.

A controlled reduction balloon or piston system could be used to slowly allow tissue healing or reestablishing load bearing capability over time. For example, a piston-like device could be constructed such that the slow expansion or shrinking of the PFC-related gas volume causes the cylinder within the piston structure to move in or out. In one embodiment the device deflates to about zero volume or length in a period of a minute to a month. This could be advantageous in after certain surgeries or to assist the healing process. For example, in FIG. 39 cuff-like and rod-like implants 66 are shown connected to vertebrae 122. A cuff-like implant 66 can surround one or more vertebral bodies. A rod-like implant 66 can be connected to opposing spinous processes 123 with fasteners 124. After spinal surgery, one or more of these types of implants could be used to temporarily support the vertebrae. Slowly over time (days or weeks, months) the implants 66 would add load to the healing vertebrae. Likewise, knee surgery, spine surgery, shoulder surgery, hip surgery or other procedures involving broken bones or damaged joints would be potential applications.

Controlled expansion/reduction devices according to one or more embodiments can create space, maintain space, occupy space, or establish an attenuative capacity within or at a space. Further examples of particular applications for controlled expansion/reduction device include site preparation for breast implants, calf implants, buttock implants, transplanted organs, plastic surgery sites, facial reconstruction, and spinal repair. Similarly a controlled reduction balloon could be used where large amounts of soft tissue have been removed such as after liposuction or organ removal.

Controlled reduction implants could be made from bioabsorbable polymers that sacrifice material over time and shrink or become more or less elastic or are completely dissolved and absorbed when deflated.

Tissue Expander

Smooth muscle in the human body is an example of a viscoelastic material, meaning that it exhibits a phenomenon known as "stress relaxation." When a muscle is stretched to a new length, it responds initially with a significant increase in force. This is the elastic response of the material. This is followed by a decline in force that is initially rapid, and then continuously slows until a new steady force is reached. Correspondingly, if a muscle is subjected to a constant force, it will elongate slowly until it reaches a new length. This phenomenon, the complement of stress relaxation, is known as tissue creep. [Medical Physiology: Principles for Clinical Medicine; By Rodney Rhoades, David R. Bell; $3^{rd}$ Edition; Published by Lippincott Williams & Wilkins, 2008; page 166]. These phenomena are commonly exhibited when an athlete runner stretches their muscles after exercise. In this case, a force is applied, and the muscle stretches until a new muscle length is reached.

According to one aspect of the disclosure a tissue expanding implant charged with PFC media is placed within or between viscoelastic tissue such as muscle or skin. Such tissue will exhibit stress relaxation and there will be an initial high force exerted on the tissue expanding balloon, which will gradually decrease until a new lower constant force is reached. Unlike a conventional tissue expanding balloon, it is not necessary to access the tissue expanding implant and refill it periodically to continue the process of stressing, then stretching and relaxing the tissue. Not having to access the implant to refill it is particularly advantageous in applications requiring percutaneous access with its associated risk of infection and expense.

In one embodiment, a PFC mixture is combined with a specially selected balloon membrane material to provide a tissue expanding implant that automatically expands without requiring repeated percutaneous access. An additional benefit is that the design of such embodiments can inherently prevent uncontrolled expansion of the expander which will serve to minimize undesirable effects such as tissue rupturing, or ischemia.

For example, in the breast augmentation or reconstruction example discussed above and shown in FIGS. 38A and B, because the implant 66 is charged with a selected PFC element the viscoelastic tissue can be slowly moved and stretched without having to re-inflate the implant 66 and without a pressurized gas source.

In one embodiment, an implant filled with air and a small quantity of PFC is placed into tissue or between layers of tissues where expansion is desired, for example under the skin and above the muscle of a patient's abdomen. In another embodiment, the implant can be used as a tissue expander in preparation for a skin graft of the newly stretch skin. The size of the implant and the quantity and vapor pressure of the PFC can vary based on factors including the size and weight of the patient, the patient's age, their health, the purpose of the tissue expansion, the gas permeability of the implant material.

An inflatable implant filled only with air would deflate over time due to the pressure exerted on it by the tissue. The addition of the PFC sets up two equilibriums such that:

$$P_{Inside\ Balloon} = P_{Exerted\ by\ tissue} + P_{Balloon\ Skin-tension} \quad (12)$$

And:

$$P_{Inside\ Balloon} = P_{N2} + P_{O2} + P_{other\ gases} + P_{PFC} \quad (13)$$

Over time, the gas partial pressure components ($P_{N2} + P_{O2} + P_{other\ gases}$) will equilibrate until they equal the gas tension of dissolved gas in the tissue and liquid surrounding the balloon. The gas tension of $N_2$ will be roughly the same as found in atmospheric air since the body does not metabolize nitrogen. The gas tension of $O_2$ will vary depending on a variety of factors. Thus, the selection of the material and the PFC partial pressure are governing factors in determining the pressure of the tissue expanding balloon implant.

Coatings

Despite the hydrophobic tendencies and relative insolubility of PFCs in water and bodily fluids, PFCs will diffuse out of certain enclosures. This can be minimized by various surface treatments including lubricity coatings, anti-microbial coatings, acid or basic pH coatings, drug eluting or containing coatings, roughening, or establishing a positively or negatively charged surface. Both the interior and/or the exterior can be treated and each could be treated in a like or different matter. For example they can be charged + on the outside and − on the inside or rough on the outside to form and capture bubbles and smooth on the outside to be non-irritating. The inside and outside of the enclosure can be hydrophilic or hydrophic, alternatively the inside and outside can be treated to have opposite attractiveness to water.

Examples of suitable coatings for various devices disclosed herein include: aqueous hydrogels on inside to prevent bubble formation, butyl rubbers to hold in PFCs, metal coatings, nano-crystallized silver based antimicrobial coating, polyvinylpryrrolidone based coatings, drug coatings including duloxetine hydrochloride, nerotranmitters mediating drugs, analgesics, antiseptics, antibiotics, incontinence treatment drugs, anti-cancer drugs, cystitis treating drug, and oxybutynin.

Initial and Automatic Inflation

Certain embodiments of disclosure involve the inflation of implants described herein with initial infusions of various media, including gases or liquids of air, nitrogen, oxygen, carbon dioxide, PFC, etc. The initial infusion can be before or after the device is implanted. The initial infusing can be delivered via a syringe, tube, capsule, ampule, cannulae or other known delivery devices. For example, any of the delivery devices shown and described herein can be used (see FIGS. 6-18).

In another embodiment, a self-inflating implant comprising a selected PFC element and an enclosure at least partially permeable to nitrogen and oxygen is provided. After implantation, the PFC vapor will dilute any air component gases within the enclosure and cause the air component gases in the anatomical structure to diffuse into the enclosure until equilibrium is reached thereby inflating the enclosure device.

In one embodiment, a pressurized implant is adapted to inflate over time to a selected volume or pressure and then deflate in response to an elevated pressure. For example, an implant is inserted within a bladder and inflates to a first selected pressure or volume. Upon the application of an external load or pressure, such as when the patient voids the bladder, the implant reaches a second selected pressure, at which point the implant is adapted to rapidly decrease in volume as the high vapor pressure element within the implant condenses into liquid. When the external load is removed, such as, after the bladder is empty, the implant will gradually return to its first selected volume or pressure. Thus, by providing an implant operable to attenuate bladder pressure spikes within a certain range and then quickly deflate at the time of voiding, a diminished and more comfortable volume is present at the time of emptying of the bladder. Therefore, a more comfortable treatment is effected.

Bubble Formation

In certain embodiments, a PFC permeable skin (e.g. silicone) is used. In these embodiments, the skin pressure of the implant at equilibrium is increased because of the use of the PFC permeable skin. Also, the PFC partial pressure is higher making the total gas tension (including PFC) at the implant surface higher than the hydraulic pressure. This will cause bubbles to grow on the implant surface.

When bubbles are attached to the implant surface, the PFC no longer has to go through the diffusional barrier of water. Thus, a constant stream of bubbles stabilized with PFC are generated. This can be an advantage in some applications such as the bladder where more compressible volume is generated, but can be a detriment in some uses, such as in the eye for example. Though in either case, the generation of PFC containing bubbles causes a much faster loss of PFC from the implant.

These PFC stabilized bubbles contain only very small masses of PFC and thus, while more stable than air bubbles, will not stay inflated for extended periods. The PFC bubbles will collapse as PFC is taken away from the local environment.

A condition for bubble growth prevention is that the PFC diffusional resistance through the skin has to drop the device surface PFC gas tension (cause a PFC concentration gradient) equal to more than the skin pressure $P_{skin}$. ($P_{PFC}$-$T_{PFCsurface}$>$P_{skin}$ where $T_{PFCsurface}$ is the gas tension of PFC at the device surface).

Bubble formation can be prevented with a low skin pressure at equilibrium or having a skin with a higher diffusional resistance to PFCs. If higher skin pressures are used, lower PFC permeability skins can be provided to prevent bubbles. Reducing the outer surface concentration of PFC bubbles will also reduce their formation. Such conditions can include fluid movement that flushes away the surface PFC bubbles.

In another embodiment, bubbles may be prevented by coating the inside surface of the implant with an aqueous gel. In some embodiments, the gel can be about 1 mm thick. In another embodiment water is used to coat the surface, as it is an excellent barrier to PFC diffusion while still allowing soluble gas diffusion through the implant.

The gel can be any biocompatible gel with a high water content (e.g. hydro-gels, starch, hydroxyethyl starch, polyacrylamide, hyluronic acids, dextrans, carboxymethyl cellulose, purified gelatin, modified collagen, water filled silica "smoke"). In some embodiments the gel is dried onto the inside of the implant in a thin layer and spontaneously rehydrates and expands in thickness when exposed to body fluids, such as when water permeates through the skin. The gel can cause the PFC concentration gradient of the first few millimeters of fluid on the outside of an uncoated device, to now occur on the gel layer inside the device. The gel layer is subject to the skin pressure and thus no bubbles would form inside or outside of the implant.

Generator

In one embodiment PFC is contained in a porous enclosure, balloon, or envelope with or without additional gases. The porosity of the enclosure is selected such that the PFC diffuses through the balloon material and, since it is highly hydrophobic, does not dissolve in the external liquid, but would form bubbles on the surface of the balloon. This system could be used as a "gas bubble generator" in a body cavity. The advantage could be the addition of gas (compressible) to a liquid (incompressible) system thus increasing the compressibility of the overall fluid system and its ability to attenuate pressure spikes or sudden changes in pressure. Such an embodiment may also attenuate two separate pressure ranges, one corresponding to the compressibility of the bubbles and another corresponding to the compressibility of the balloon or envelope.

Packaging

There may be situations where it would be desirable to store PFC in what essentially amounts to a container made of a gas permeable material such as a prefilled implant balloon. Consider, for example, a silicone balloon containing PFC, as described above. This balloon exhibits some very desirable characteristics such as staying inflated for extended periods of time when immersed in bodily fluids. Such a balloon could be filled with only PFC, or with PFC plus air, when it is already residing within a location within the body; or at the time when it is placed inside the body. However, it may be desirable for manufacturability or usability reasons to have a device "preloaded" with a quantity of liquid PFC. For example, this could be used to simplify the clinical procedure in which such a device is inserted into the body. Instead of inserting the balloon and then filling it; the procedure could involve inserting a device that already contains a quantity of liquid PFC. This PFC could, over time, induce other gases found in the balloon's external environment, to diffuse into the balloon, achieving a concentration or gas tension equilibrium, and causing the balloon to inflate on its own, in-vivo. In some embodiments, a delivery device with a preloaded implant could be packaged together.

In some instances a preloaded device could, over time, lose its PFC contents. It will also inflate itself, before insertion, if stored in contact with air. Even if the balloon is physically constrained, so that it cannot expand, a small amount of PFC vapor will form within the balloon. This will diffuse across the gas permeable walls of the silicone, and exit the balloon. Over time, all of the PFC will exit the balloon in this manner. If the PFC-containing-balloon is placed within a gas impermeable pouch, such a foil pouch, and all air is evacuated (vacuum packed), there will still be a situation where the PFC will exit the balloon slowly and collect in the pouch when exposed to a temperature gradient, and will inflate the foil pouch over long storage times if the pouch has even a very small gas permeability, continuing until either a force equilibrium is formed with the inflated foil pouch, or until all of the liquid PFC within the balloon is gone.

Figure 40:
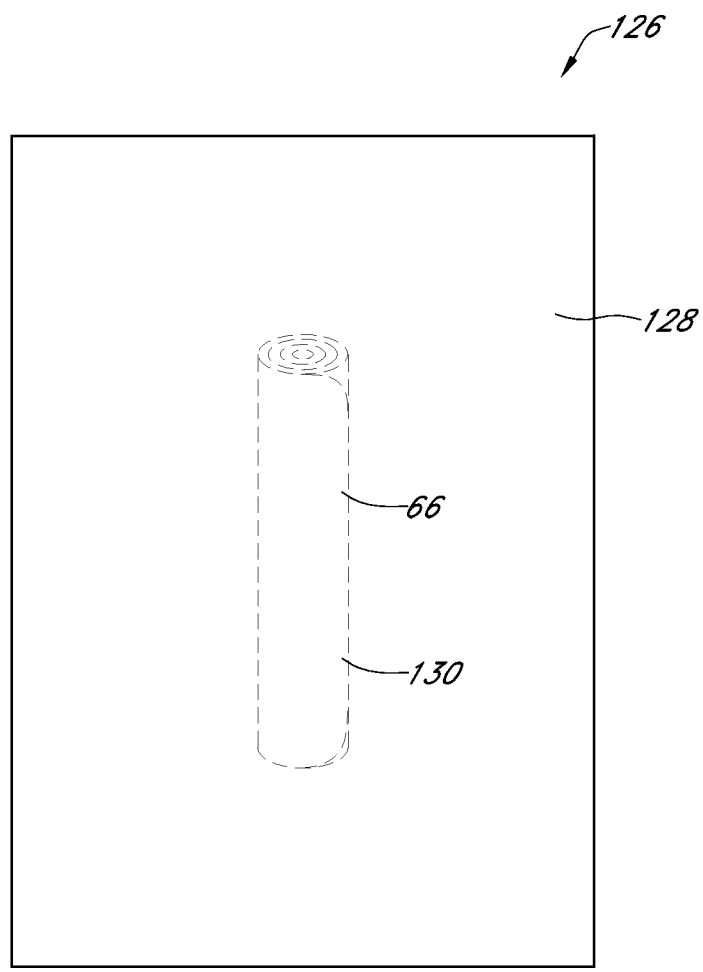
FIG. 40 shows a prepackaged implant in a liquid bath.

Accordingly, one embodiment, shown in FIG. 40, involves a pre-loaded package or gas impermeable pouch 126 with a quantity of liquid PFC 128 in the pouch external to the implant 66 which is also preloaded a with a quantity of PFC. In this way, the device has the same PFC vapor concentration/partial pressure on the inside and the outside. Therefore there is little or no diffusion gradient to induce loss of PFC from the device. In this way the supply of liquid PFC 130 within the device is not depleted prior to implantation as the device is kept in storage and implant 66 is maintained in a deflated state until it is within the body. Moreover, selecting a slightly higher vapor pressure PFC 128 outside of the implant 66 would ensure deflation of even a partially inflated implant, during storage.

After the particulars of the implant have been selected according to the various selections above, the implant can be prepared and then implanted into the treatment site in the body. Various non-limiting examples follow which demonstrate certain aspects of the implant in certain parts of the body.

EXAMPLE 1

In one illustrative embodiment, intraocular implants or other implantable devices described herein comprise a silicone elastomer, polyolefin or acrylic balloon that may be used to contain air and the selected PFC vapor. The balloons may range in volume from 0.1 milliliters to 2 milliliters.

The eye is a challenging environment in which to deliver and maintain the inflation of a therapeutic implant because the intraocular pressure exceeds atmospheric pressure and the oxygen tension in the anterior and posterior segments of the eye is known to be significantly less than the oxygen tension in normal atmospheric air. In the absence of a PFC, the balloon will deflate due to the intraocular pressure (TOP) exceeding the oxygen and nitrogen tensions in the anterior and posterior segments of the eye. The oxygen tension in the normal atmosphere is approximately 159 mm of Hg. The oxygen tension in the intraocular environment ranges from 10 to 30 mm of Hg. The nitrogen tension in the intraocular environment, as well as that of other gases in normal atmospheric air (i.e. argon, helium), is approximately the same as that of normal atmospheric air. Thus, the gas tension deficit in the intraocular environment is primarily due to reduced level of oxygen. For the purpose of this example, the oxygen tension in the intraocular environment is defined as 20 mm of Hg. Accordingly, the gas tension deficit is 139 mm of Hg (159 mm of Hg minus 20 mm of Hg). The total gas tension in the intraocular environment is approximately 621 mm of Hg (594 mm of Hg contributed by nitrogen, 20 mm of Hg contributed by oxygen and 7 mm of Hg contributed by all other gases found in normal atmospheric air).

If the IOP is 775 mm of Hg, a PFC mixture is needed to deliver a minimum vapor pressure of 154 mm of Hg (775 minus 621 mm of Hg). This can be accomplished with a mixture of perfluorohexane and perfluoroheptane. The ratio of the two PFCs is determined using a weighted average calculation on a molar basis. To assure that balloon inflation is maintained, the vapor pressure of the PFC mixture may be increased by 1-100 mm of Hg. In this case the skin tension of the balloon will offset the amount by which the PFC vapor pressure exceeds the IOP minus the total gas tension within the fluids surrounding the balloon. The additional vapor pressure will compensate for normal diurnal fluctuations in IOP.

To maintain inflation, the balloon is charged with the PFC mixture at the time of inflation or at any point following implantation. The amount of PFC which is added is determined based upon the loss rate of PFC through the balloon walls and the desired duration of inflation. For a balloon composed of a high density polyethylene, a 50 microliter PFC volume can be expected to maintain inflation for 6-18 months; the actual duration of inflation will depend upon a variety of factors, including the balloon wall thickness, surface area, and any coatings or treatments.

EXAMPLE 2

Self-inflation of a balloon in an ophthalmic application can be achieved with a balloon composed of a material which is permeable to oxygen and nitrogen. At the time of implantation, the balloon is charged with the PFC mixture and a minimal amount of air (e.g. 1-25 microliters). The balloon may also be filled with additional air to reduce the time required for complete balloon inflation. Shortly after the time of implantation, the PFC vapor pressure exceeds the IOP in the eye minus the total gas tension in the fluids surrounding the bladder. Self-inflation will occur as a result of diffusion of oxygen and nitrogen, from the vitreous in the case of a posterior segment placement or from the aqueous in the case of an anterior segment placement, through the walls of the balloon as the PFC vapor has diluted these gases, inside the balloon, to partial pressures that are less than their gas tensions in the contacting fluids. The time required for self-inflation will vary from several days to several weeks depending upon the total gas tension in the balloon as well as the rate of gas transmission through the balloon wall. The time required for self-inflation is inversely related to the total gas tension in the balloon.

EXAMPLE 3

To assure that balloon inflation is maintained, the vapor pressure of the PFC mixture may be increased by 1-100 mm Hg relative to the level that matches the IOP/fluid total gas tension differential. In this case the skin tension of the balloon will offset the amount by which the PFC vapor pressure within the balloon exceeds the equilibrium value. The skin tension will pressurize the balloon gases until the oxygen, nitrogen and other gas partial pressures within the balloon rise to match their gas tensions in the contacting fluids. The additional vapor pressure will compensate for normal diurnal fluctuations in IOP.

For internal balloon gas equilibrium pressures that exceed the IOP, the skin tension of the balloon counterbalances the excess gas equilibrium pressures (defined as equilibrium pressure minus IOP or the PFC vapor pressure plus the total fluid gas tension minus the IOP). The mechanical characteristics of the balloon as well as its polymeric structure are such that the balloon resists overexpansion by the excess gas equilibrium pressure. The modulus of elasticity, wall thickness and crosslink density should be optimized to avoid overexpansion.

Specifically, a silicone elastomer balloon composed of a silicone with a Shore A hardness of 30 and wall thickness of 0.20 millimeters can resist overexpansion produced by an excess gas equilibrium pressure of 20 mm Hg.

EXAMPLE 4

Figure 41A:
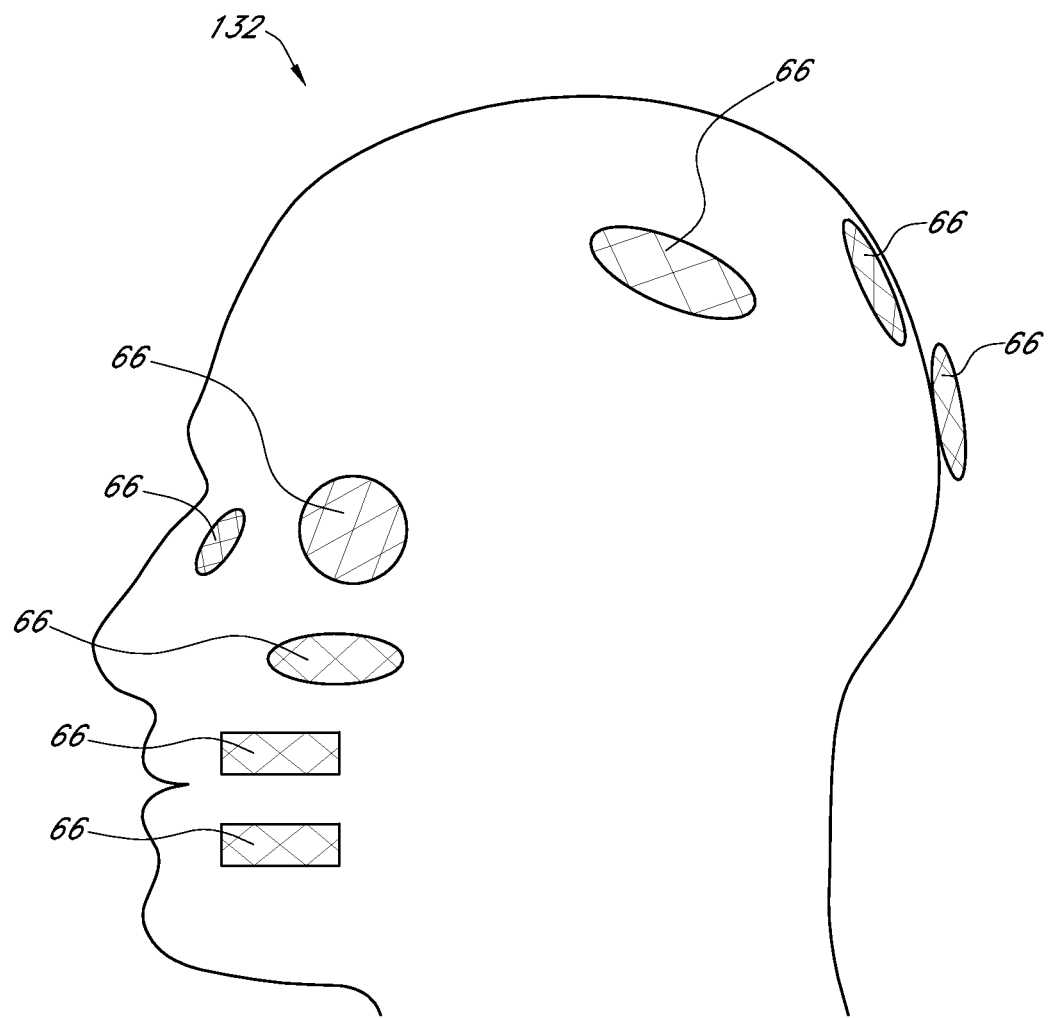
FIGS. 41A-C show cross-sectional axial views of implants within a skull and under the scalp.

FIG. 41A illustrates a side view of a human head 132 implanted with various inflatable therapeutic implants 66. The implants 66 can comprise a flexible membrane enclosure, balloon, or envelope and are charged with a high vapor pressure media such as PFC. In some instances the implant contains a valve and may be at least partially filled with air or another gas at some point during the implantation process. The implants 66 can be shaped, coated, and comprised of various materials as described throughout this disclosure. As shown, certain implants 66 shown have been implanted in the cranium to attenuate intracranial pressure, prevent aneurysms, ameliorate airflow conditions contributing to sleep apnea or snoring, create space, stabilize tissue, or as part of a reconstructive surgery. Other implants 66 are shown implanted within the sinus, against the palate, within the gums, behind the cheekbone and along the jaw. The implants 66 can be delivered through open surgery, percutaneously, nasally, orally, or ocularly.

In one embodiment, one or more implants 66 are implanted and then injected with high vapor pressure media. In another embodiment, one or more implants 66 are implanted and then injected with high vapor pressure media and a gas or air. In other embodiments, the implant 66 is implanted and is fully charged with PFC media. Over a selected period of time the implant 66 will expand until restricted by the enclosure or surrounding tissue. As described above, the implants 66 can be adapted to exhibit controlled expansion and/or reduction. In one embodiment, the expansion of the implant 66 is limited to expand or contract against tissue in order to align facial bones as part of a reconstructive surgery.

Figure 41B:
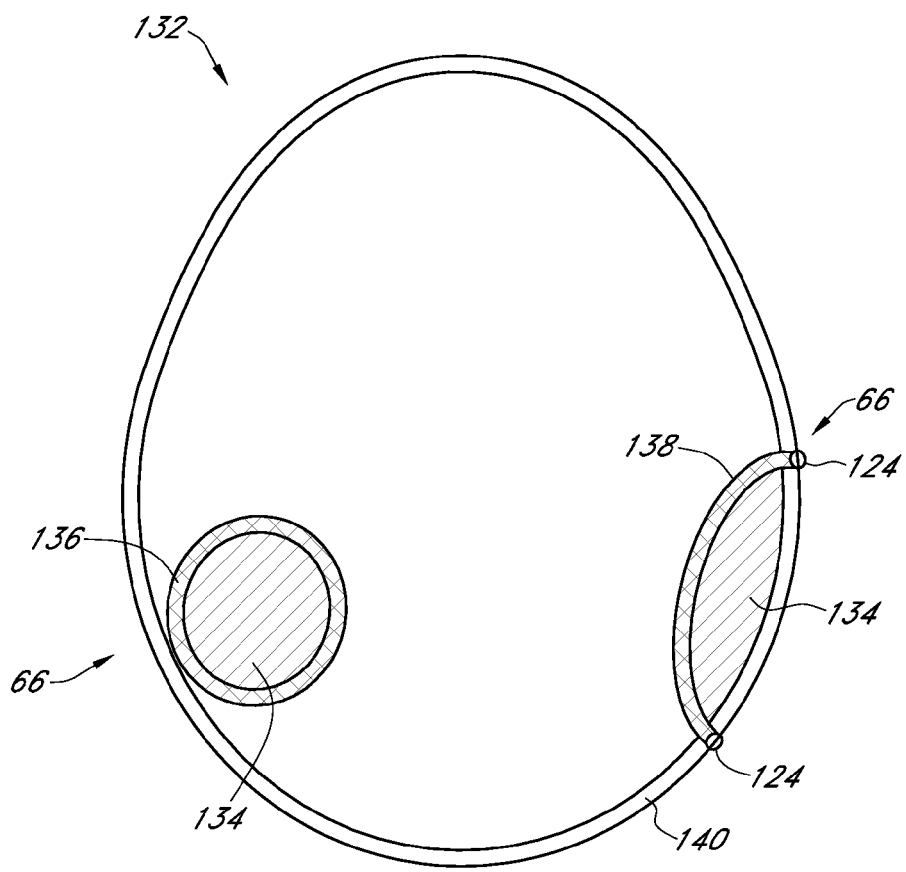

FIG. 41B shows a top view of a head 132. In this embodiment inflatable therapeutic implants 66 are used to constrict two tumors 134. One implant 66 is shown as a sleeve 136 that has been placed about a periphery of the tumor 134. A second implant 66 is shown as a sheet or patch like 138 embodiment with two anchors 124 used to anchor the implant against an interior surface of the cranium 140. The inner surface of the implant 66 expands or inflates over time and constricts the tumor 134 and/or blood flow to the tumor 134. In certain embodiments, the tumors are prohibited from growing; in other embodiments, the tumors are reduced in size.

Figure 41C:
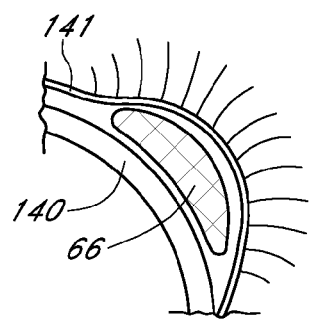

FIG. 41C shows another embodiment of an implant 66 used to stretch the scalp for harvesting and replanting hair. The implant 66 is shown implanted between the skin 141 and the cranium 140. Over time the implanted devices can expand and stretch the tissue.

EXAMPLE 5

Figures 42A, 42B:
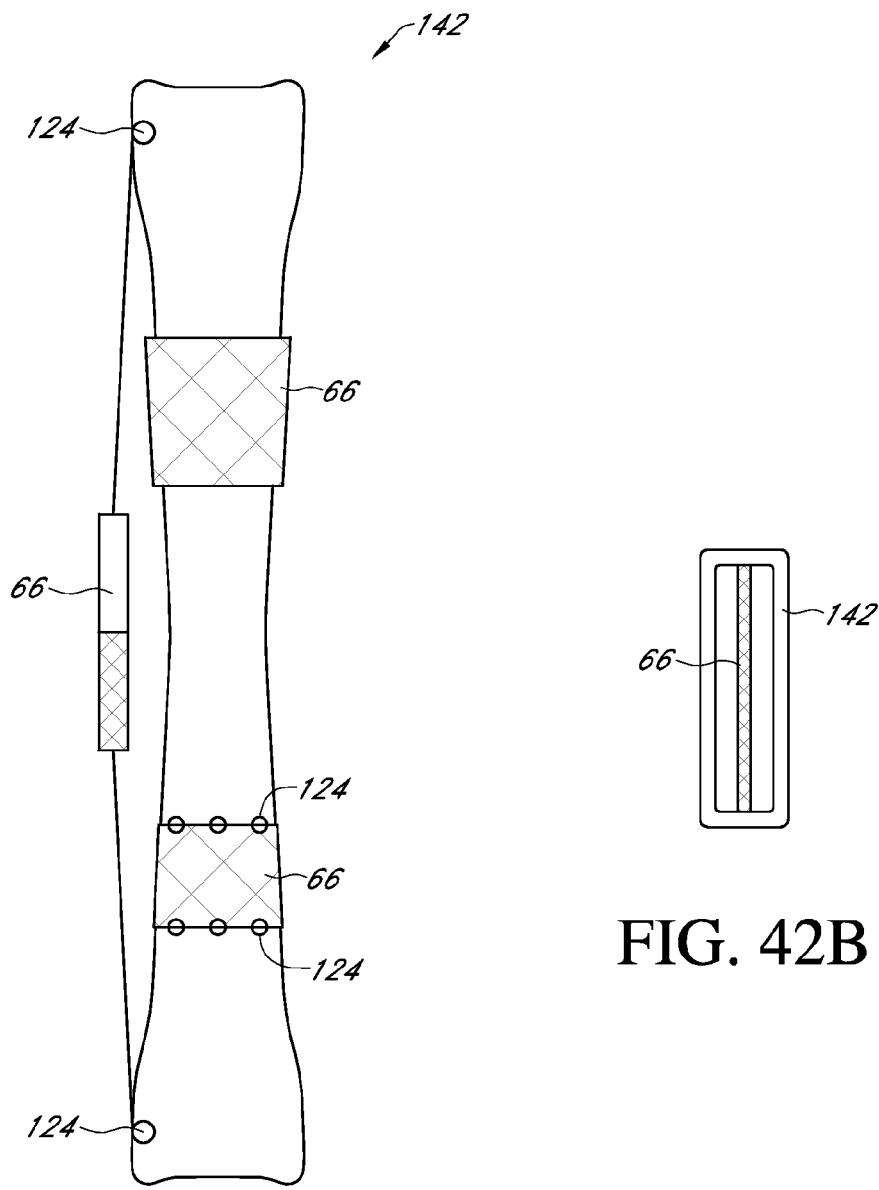
FIGS. 42A-B show a long bone with implants for compressing or tensioning the bone.

In FIG. 42A several versions of an implant 66 are provided for treating bones. Shown is a piston-like implant 66 connected with anchors 124 to opposing ends of a long bone 142, such as a femur. The piston-like device could be constructed such that the slow expansion or shrinking of the PFC-related gas volume caused the cylinder within the piston structure to move outwards or inwards. After some traumatic injuries, a patient can be left with one of the long bones in the body too short, for example, one femur shorter than the other. The above embodiments can help treat such situations.

Figure 43:
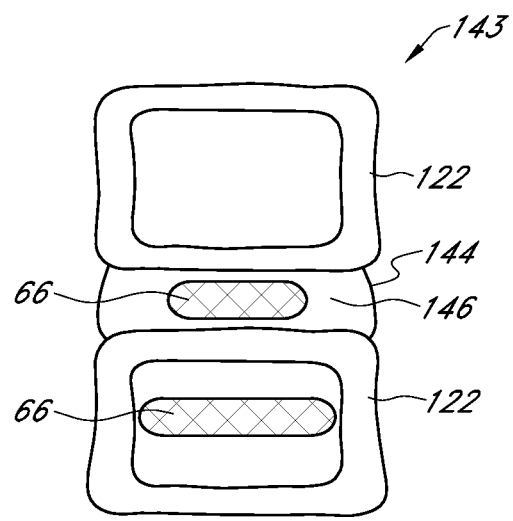
FIG. 43 is cross-sectional view of a vertebral body and disc in which expandable implants have been implanted.

Also illustrated are two versions of cuff or belt like devices for compressing or supporting bone. One inflatable cuff device is shown anchored to the bone 142 with anchors 124 and the other is simply wrapped around the bone. The cuffs are charged with a selected PFC element and the membranes are selected to exhibit a desired compliance in order to stimulate bone growth or support a weakened or fractured section of bone. In this arrangement the bone is under compression, however, as shown in FIG. 42B, an internal rod-like or piston implant 66 can alternatively be used to expand the bone or place it under tension. FIG. 43 illustrates yet another application of an expandable or inflatable therapeutic device as used in the rehabilitation of the spine. Shown is a functional spinal unit 143 having opposing vertebral bodies 122 and an anulus fibrosis 144 surrounding a nucleus pulposus 146. Therapeutic implants 66 to support load, stimulate growth, or compact or compress cancelleous bone are shown implanted within the anulus, and within a vertebral body.

Figure 44:
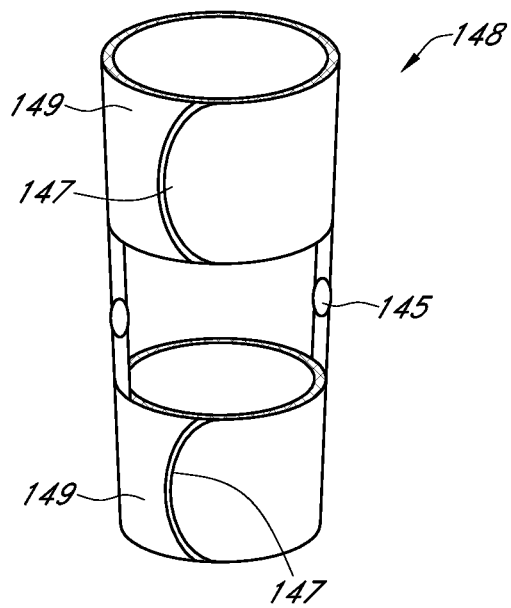
FIG. 44 is a perspective view of a brace for a movable joint, such as the elbow or knee.

In FIG. 44, a knee or elbow brace 148 is illustrated having an upper inflatable cuff 149 charged with a selected PFC element, a closure device 147 for providing initial fitting around a limb coupled by hinged members 145 to a lower inflatable cuff 149 also charged with a selected PFC element. This embodiment is particularly advantageous because the PFC element can be selected such that over tightening of the cuff 149 can cause a certain threshold pressure whereupon the PFC media will condense from a gas to a liquid resulting in a loss of volume and thereby loosening the cuff 149 and preventing circulation problems or discomfort.

Figure 45:
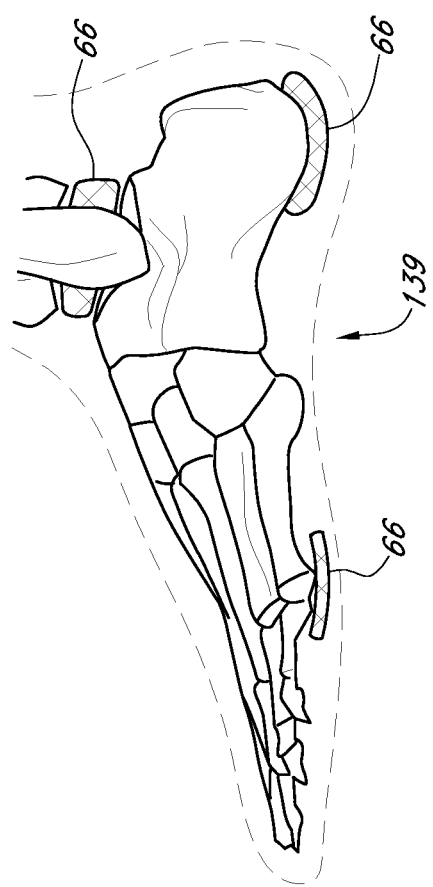
FIG. 45 is a sagittal view of a foot with various implants.

In another embodiment as illustrated in FIG. 45, various implants 66 are implanted among the tissues of a foot 139. Placement of implants 66 charged with high vapor pressure media along the heel, ball, and about the ankle can provide support and cushioning and stability for the foot.

EXAMPLE 6

Figure 46:
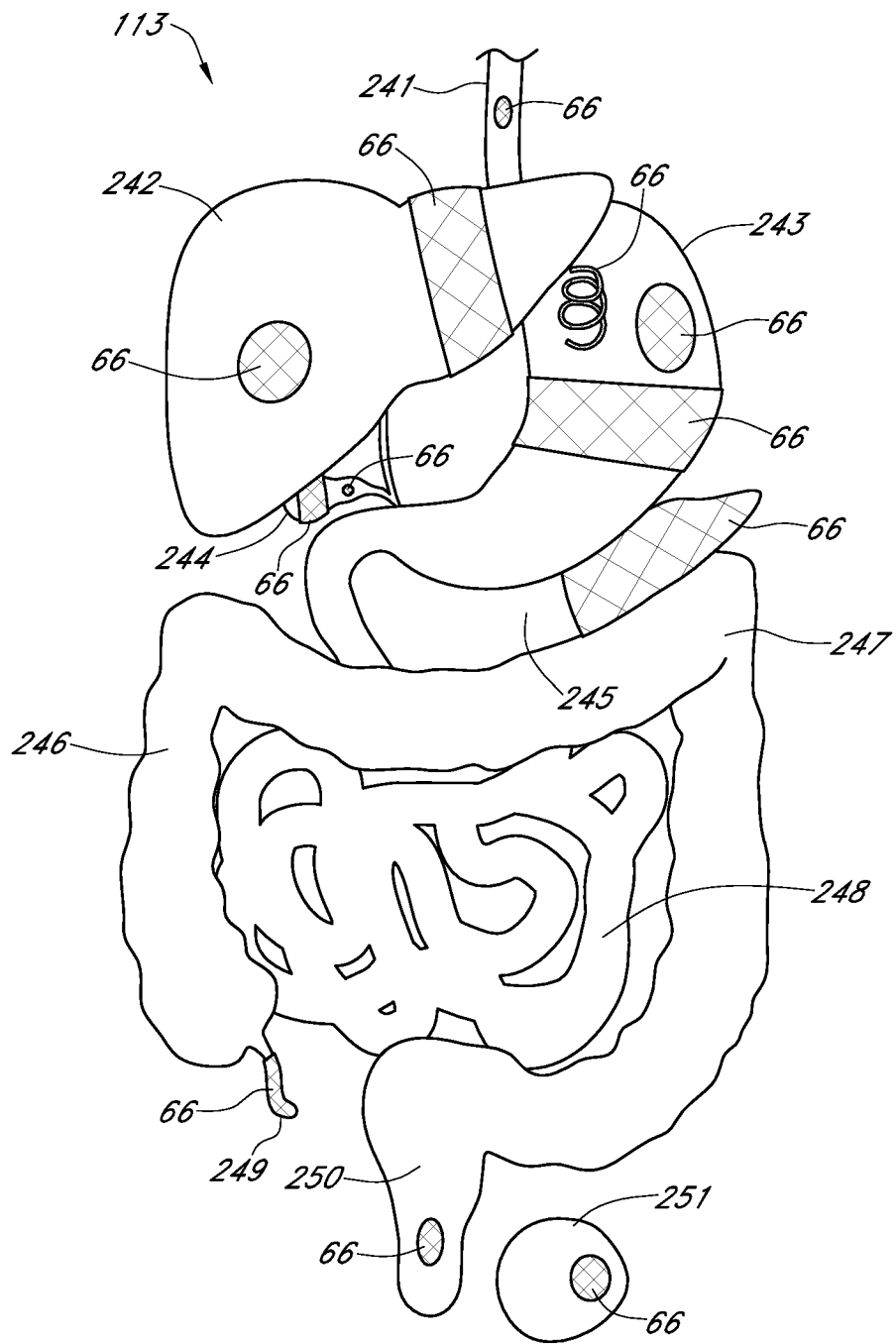
FIG. 46 shows a simplified diagram of the digestive system and various implants.

FIG. 46 illustrates the digestive system 113 and various implants 66 providing treatment such as intraorgan space creation, appetite satiation or cessation, attenuation, and constriction. Shown include cuff like constrictor devices 66 placed about the stomach 243, liver 242, gallbladder 244, pancreas 245, appendix 249, bladder 251. The constrictor devices 66 comprise an inelastic outer band and an inner inflatable member charged with a PFC element. Such a device can be used to shrink a diseased organ for removal or restrict an organ from becoming enlarged.

Also shown are inflatable implants 66 containing selected high vapor pressure media elements disposed within the esophagus 241 enroute to the stomach 243. The implant 66 is shown being ingested through the esophagus 241 in an unexpanded state. The implant may then travel or be passed at the termination of a programmed treatment cycle out of the rectum 250 in a deflated or reduced volume state. The treatment cycle can include expanding in the stomach or anywhere along the digestive tract for a desired treatment period and then deflated. In another embodiment a treatment implant 66 is placed in or adjacent lymphoid tissue to help clear out lymph. Various embodiments of implants 66 described herein may have one or more states or profiles depending on the stage of treatment including; a reduced ingestion or delivery state, an enlarged treatment state and a reduced, deflated, depleted, or degraded removal state.

EXAMPLE 7

Illustrated in FIGS. 47A-F are various anchor devices 200 having inflatable components charged with PFC elements that expand after delivery. In certain embodiments at least a portion of the device 200 is programmed to contract, deflate, or disengage after a treatment period.

FIG. 47A shows an anchor device 200 comprising an inflatable membrane enclosure 302 charged with a selected PFC element. The enclosure is connected via a connector 301 to an attachment site 300. The enclosure 302 may comprise a coating or high friction surface.

FIG. 47B shows another anchor device 200 having an attachment site 300, connector 301, a pointed shaft portion 303 and one or more deployable barbs 304 that deploy via the inflation of a piston or actuator containing a PFC element after implantation.

FIG. 47C shows a device 200 implanted within and expanded beyond a bone surface. In this example the device 200 is implanted within a vertebral body 122 and the membrane enclosure 302 is expanded within the cancellous or trabecular bone tissue inside the vertebral body 122. In another embodiment, the anchor device 200 is inserted into or through soft tissue and the membrane enclosure 302 is expanded within or beyond the tissue to establish the attachment site 300 to the tissue surface.

Figure 47D:
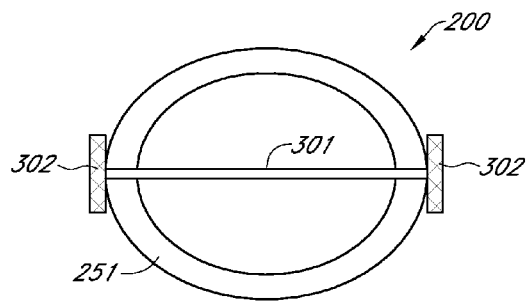

In FIG. 47D, a hollow organ such as heart, stomach, or bladder 251 is shown with an implant 200 comprising opposing inflatable enclosures 302 connected via a connector 301. The connector can be used to apply tension and move, displace or support the opposing walls of the organ. The inflatable enclosures are operable to establish or anchor the connector to the opposing walls and are oversized relative to the connector such that they are incapable of migrating through the wall of the organ once inflated via the action of the PFC element.

Figure 47E:
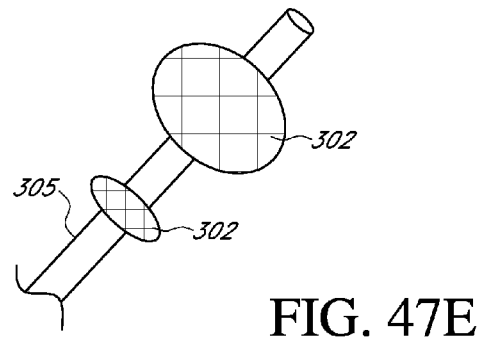

FIG. 47E illustrates a temporary anchor for a catheter 305 such as a Foley catheter. One or more lumens or membrane enclosures 302 are operable to anchor or establish the device within a treatment site upon inflation via the action of the PFC element within the lumen 302.

Figure 47F:
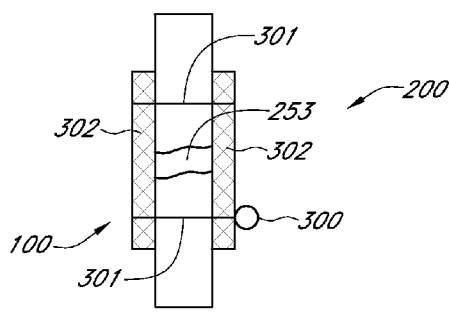

FIG. 47F illustrates yet another anchor device 200 established along opposing surfaces of a tissue. In this embodiment, opposing inflatable enclosures 302 are connected via two or more connectors 301 disposed through the tissue. The anchor device 100 can provide attachment site 300 for a suture, support the tissue, or repair or block a defect 253 in the tissue.

EXAMPLE 8

Figure 48A:
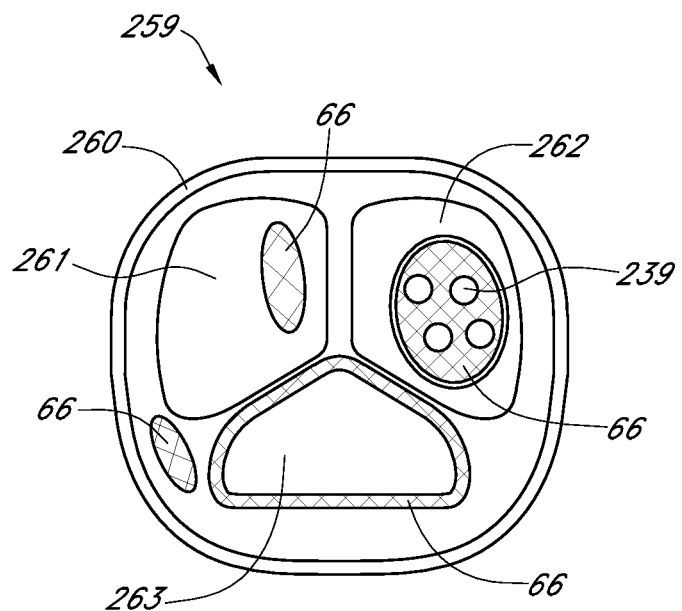
FIGS. 48A and B show cross-sectional views of a penis and penile implants.

In another embodiment there is provided a penile implant. FIG. 48A illustrates a cross sectional view of a penis 259. Shown are the left corpus cavernosum 261 and right corpus cavernosum 262 and corpus spongiosum 263 all of which are surrounded by fascia and skin 260. Expandable or inflatable implants 66 comprising a membrane enclosure and selected PFC element are shown implanted in the each of the corpi and in certain embodiments encircling at least a portion of corpus or between a corpus and fascia or skin.

In certain embodiments, the implant 66 may comprise voids or passages 239 to allow the flow of blood through portions of the implant 66. In other embodiments, the implant 66 is spiral or coil shaped.

Figure 48B:
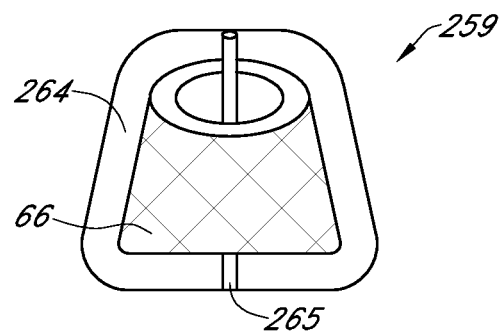

FIG. 48B shows the glans 264 of a penis 259 with an inflatable implant 66 charged with a selected PF media element at least partially encircling a portion of the urethra 265. The implants disclosed herein can be used to cause partial or full erection of the penis or to create space within the penis so that other implants may be inserted.

EXAMPLE 9

Figure 49A:
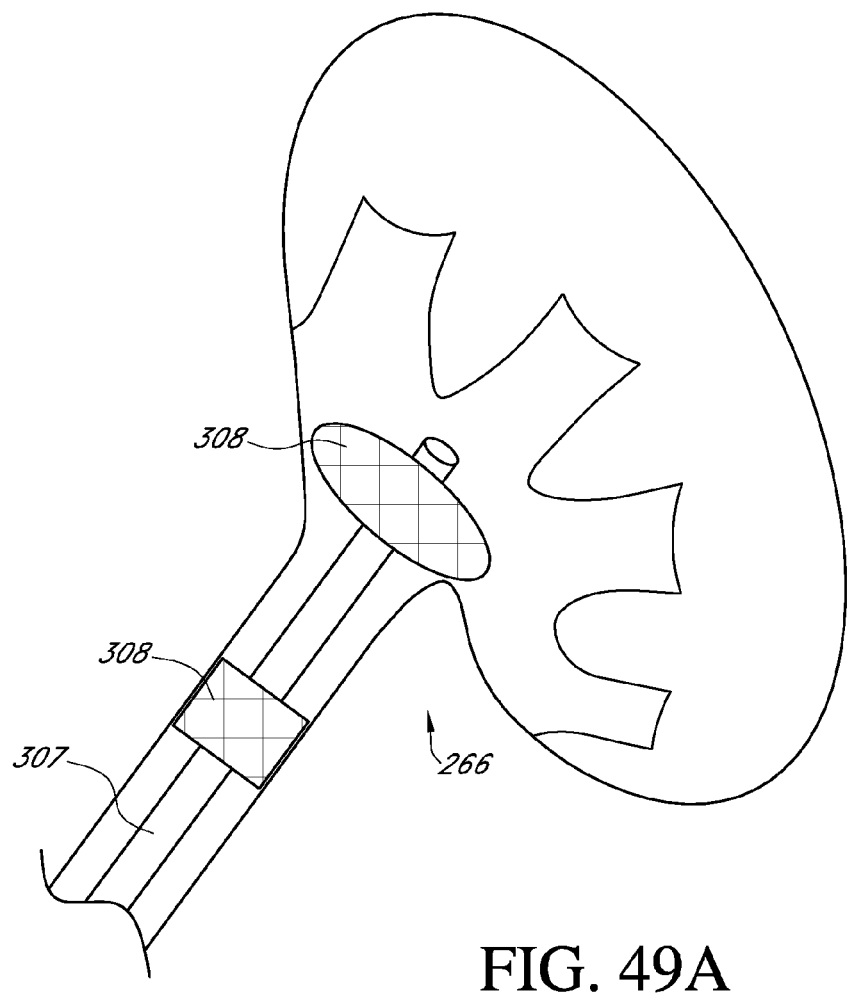
FIGS. 49A and B show cross-sectional view of a kidney and an uretal stent device.
Figure 49B:
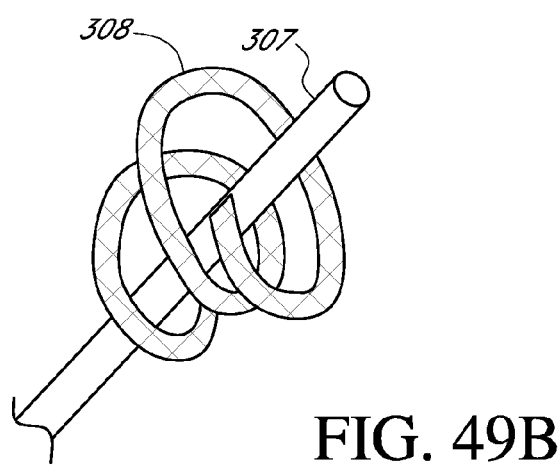

FIG. 49A illustrates a further embodiment in the form of an uretal stent anchor. Shown is a cross section view of a kidney 266 with a stent device 307 implanted within a ureters. One or more inflatable lumens 308 containing a selected PFC media element have been inflated after insertion and have formed a friction fit with the inner contours of the ureter. In another embodiment, as shown in FIG. 49B, the uretal stent device 307 comprises a coil or spiral inflatable anchor lumen 308.

EXAMPLE 10

Figure 50A:
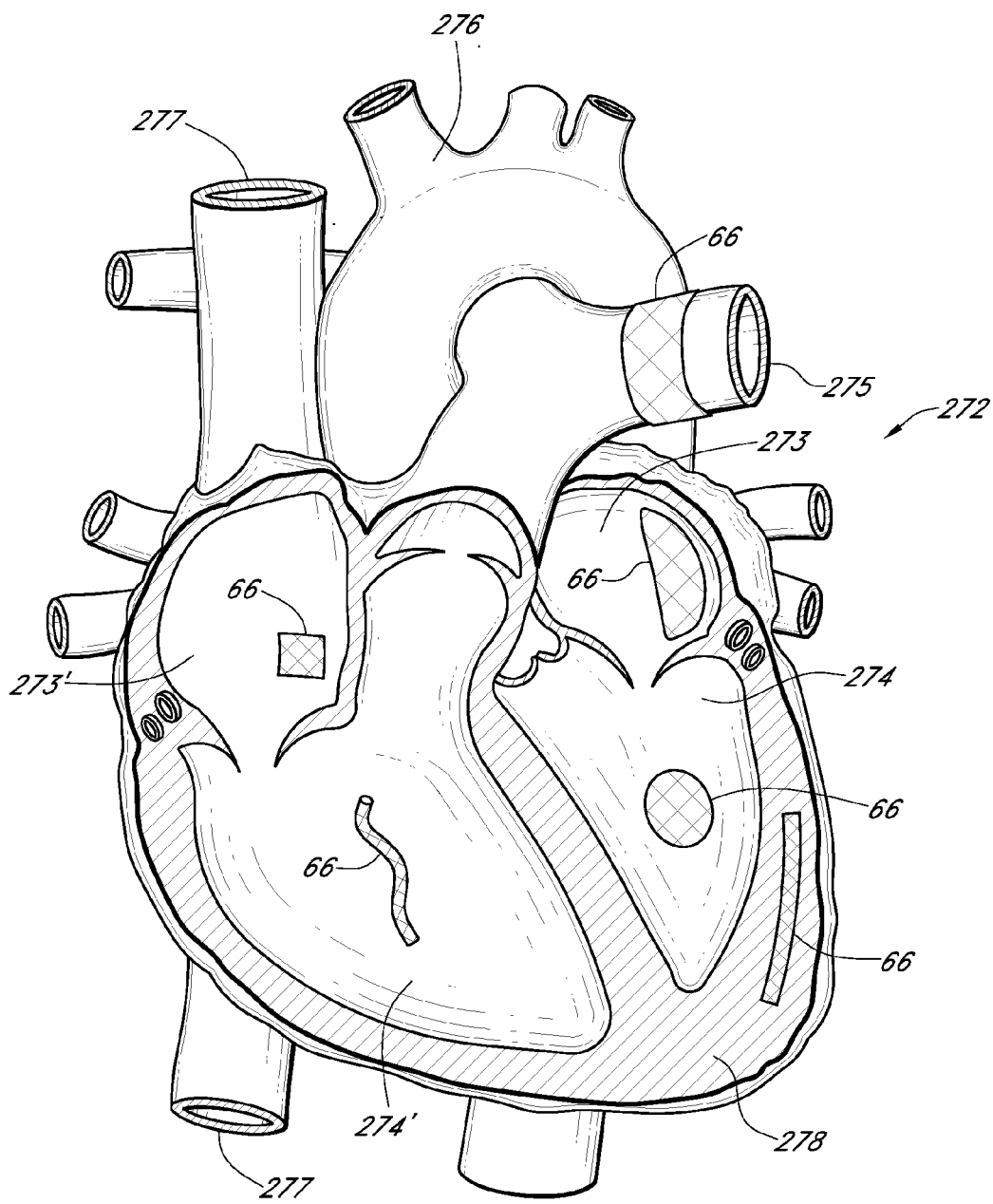
FIGS. 50A and B show a simplified diagram of a heart and related vasculature with various implants at various sites.

Turning to FIG. 50A, a cross sectional view of a heart 272 is shown. Various implants 66 comprising an inflatable enclosure and selected PFC element are shown implanted in various locations to attenuate pressures, create space, change the tissue compliancy of cardiac tissue, or reorient heart valve leaflets.

Figure 50B:
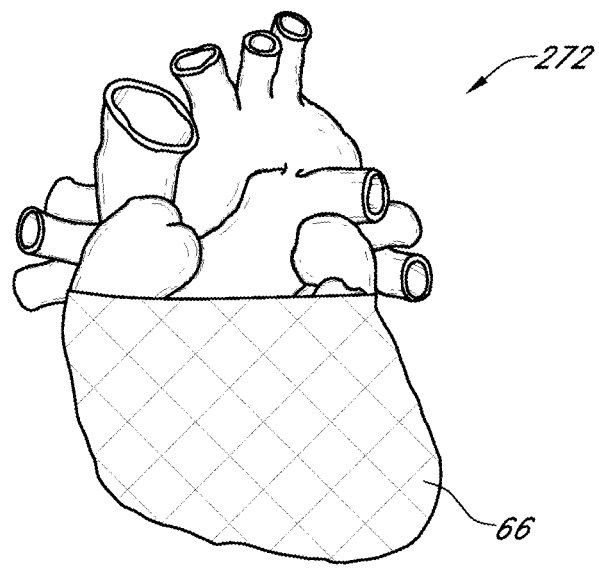

In one embodiment, the heart is treated by implanting an inflatable device 66 as described herein within one or more of the left and right aorta 273, 273', left and right ventricle 274, 274', pulmonary artery 275, aorta 276, vena cava 277 or simply within cardiac tissue 278. Such devices may optionally comprise a connector or anchor for establishing to or within the implantation site. In another embodiment, a band, cuff or sleeve-like device is placed over the vena cava 277, pulmonary artery 275, or over a least a portion of the heart 272 or pericardial sack as shown in FIG. 50B.

EXAMPLE 11

One technical problem that may be solved according to one or more aspects of the disclosure is modulating or reducing the consequence of pressure spikes within the abdomen.

Various physical events such as laughing, coughing, sneezing, or involvement in physical activity, such as, running, jumping, or picking up something heavy, can result in a sharp contraction of the abdominal muscles. This contraction can cause a sudden spike in intra-abdominal pressure which can, in turn, cause a pressure spike within the organs and tissues in the abdomen. Such a pressure spike can be undesirable. In some instances, damage to such structures can occur immediately following the incident, or can evolve over time.

For example, urinary incontinence can arise from such a physical event. These physical events subject the bladder to increased intravesical pressure. The bladder rests at the bottom of the abdomen. Abdominal pressure is exerted on the bladder in generally a downward direction and to a lesser extent from the sides. When the intravesical pressure in the bladder exceeds the resistance of the bladder's sphincteric mechanism leakage of urine can occur.

Moreover, the increased pressure event can also result in anal incontinence. When the abdominal pressure increases there is a corresponding increase in the force exerted upon the colon. If the pressure in the colon exceeds the outlet resistance of the anus there can be an involuntary loss of feces or gas.

In addition to incontinence, other pathologies or conditions can arise from pressure spikes within the abdomen. Hernia or prolapse are two such examples that can result from extreme or prolonged cycling of intra-abdominal pressure. Persons with weakened portions of the abdominal wall caused from a variety of factors such as lifting, child birth, or predisposition are particularly susceptible to hernia or prolapse.

For example, pelvic organ prolapse is common in women who have experienced multiple births; the bowel (rectocele), bladder (cystocele) or uterus (enterocele) can herniate into the vagina, or protrude outside the body. Sections of bowel can herniate through weakened muscle wall into the scrotum of men (inguinal hernia). Also, it is common for people who have had abdominal surgery to later sustain incisional hernias. The "jackhammer" effect of repeated or cyclical spikes of high pressure overtime can cause such hernias to occur. Accordingly, it is an object of one or more embodiments to lessen the extent of intra-abdominal pressure spikes.

In one embodiment, a pressure attenuating balloon or device is placed in the bowel, intestines, abdominal aorta, stomach, or along the digestive tract. The device may be a permanent implant and anchored to a tissue wall, free floating or friction fit with the organ or tissue structure. In one embodiment, an attenuator is sized to be too long and relatively inflexible to be passable around a bend in the digestive tract. In another embodiment, an attenuator is arcurate or "U" shaped, corresponding to the natural curved portion of the digestive tract and is adapted to not rotate or pass beyond the curved portion. In one embodiment, the device is ring, tube, or cylindrically shaped to allow the passage of food, liquid, or waste. In another embodiment, a device is adapted to reside outside of the digestive tract but remain in pressure communication with it via a port, membrane, or wall. Such a device could be attached to the outer wall or reside remotely within the abdomen with a connector or tube placed within or in pressure communication with the digestive tract.

Rather than attenuating the organ or sites within the abdomen that are susceptible to pressure spike influence, another method involves attenuating the abdomen itself thereby achieving a systemic result. In a preferred method, one or more pressure attenuators are placed at a site within the abdominal space. In use, the attenuator could serve to limit the peak abdominal pressure and the rate of increase in pressure resulting from an event. This reduction in pressure could have a similar effect to an intravesical balloon, and reduce stress incontinence leakage. It could also reduce anal incontinence effects. Over time it could assist in reducing the "jackhammer" effect of repeated high pressure spikes that result in hernias, prolapse or abdominal aortic aneurysm. An abdominal attenuator as described herein could also have a beneficial effect on abdominal aortic aneurysms, or hiatal hernias.

Various embodiments of implants for attenuating pressure, reversibly occupying or creating space can comprise one or more free-floating balloons, enclosures, or expandable devices. In certain embodiments, the device is incorporated into one or more sheets of other material like a patch. Accordingly, textile implants that are placed into the abdomen to repair hernias can also be adapted to contain attenuator or expansile elements. Various devices or materials comprising such devices can be surgically anchored; mechanically wedged in place after implantation; free floating; permanent, temporary, or bio-absorbable; layers of air-containing substances such as closed-cell foam; comprised of chains of or strips of connected balloons or sheets of balloon material like bubble-wrap; coated with or constructed from lubricious materials, anti-bacterial materials, or anti-adhesion materials.

Balloon type constructs could be filled with air, PFC mixtures or other gases or combinations of gases and liquids. They can be durably inflated or refilled periodically. If refillable, they can be refilled using a sub-dermal injection port that communicates through a lumen to the lumen of the balloon. They can also be connected to a "radiator cap" type percutaneous access system such as is used for the exchange of continuous abdominal peritioneal dialysis fluid exchange, or for a colostomy. Elastic balloons can simply be injected into the abdomen percutaneously through a needle.

In some embodiments a material that forms a solidified foam is used to create, in effect, a closed cell construct containing multiple pockets of encapsulated air. In some embodiments, temporary or permanent attenuator devices are used to reduce peak pressures in the abdominal region to prevent trauma to organs or tissues during procedures or after surgery to reducing post-operative pain.

Various intra-abdominal devices described herein can also be adapted to serve as platforms for drug delivery, pressure sensing, monitoring, storing or emitting data such as electromyograms, electrocardiograms, or other signals. In other embodiments such devices can also be used as platforms for electrical stimulus, transducers and pacer elements.

In some embodiments one or more devices described herein can be attached to, wrapped around, wedged within, or anchored in proximity with organs, tissues or other structures such as the bladder, bowel, abdominal cavity, aorta, spine, or an incision site.

Other Methods and Devices

In one embodiment, a constant pressure device as described herein such as a cuff can apply force to structures of the body but be force limiting and self adjusting, e.g. never enough force to cut off blood supply. These and other devices can be made to slowly inflate or slowly deflate, or with limited PFC, self-inflate and then self-deflate according to different methods. Other devices according to additional aspects can preferably dissolve after it deflates and may be comprised of collagen, PLGA, and/or modified starches.

One of ordinary skill in the art could use or modify the devices and methods disclosed herein or existing devices (such as adding a tissue or bone anchor) to: push back aneurism or hernia in a controlled manner over time; slowly make space for breast implant, maintain space within a tissue, between tissues or within an organ, make or maintain space for an organ transplant or pacemaker/device; hold open/take stress off of cartilage in knee joint; push on spine to straighten spine or replace, repair, or restore the function of a portion of a vertebral body or disc; (as a simple bag and PFC load) to soak up air (or other gas, methane) in abdomen or head and easily removal with syringe; to pull on sutures or devices as it deflates or if a shrunk device is placed between two strings, it can pull very hard (like pulling back string on a bow bends the wood) to pull things together gradually or with constant readjusting force; provide a device that grows and then deflates and pass through the stomach for weight loss or ulcer treatment; provide an expandable member on a distal tip of a Foley catheter for anchoring the device within a hollow organ or tissue site, provide a doughnut shaped device with a non-stretching band about its periphery to slowly apply constant pressure to pinch off appendix or tumor blood supply or gentle pressure cuff to limit blood pressure to esophagus or vasculature in fluid communication with an aneurism, provide a sheet-like, rod-like, plate-like, or spherical expandable implant to bluntly dissect or align tissue, anchor or open a stent.

Intravesical Infusion Devices, Materials, and Therapeutic Agents

One or more implants described herein can further comprise or serve as a platform for drug, diagnostic, agent, or therapeutic substance delivery. Such delivery systems can include a mechanical delivery system having one or more syringes, pistons, nozzles, valves, reservoirs for holding the substance, needles, atomizers, etc. Such devices can further comprise a MEMS, piezo-electric, or semiconductor activated port, window, nozzle or aperture. At least a portion of the device can comprise an eluting substrate, biodegradable port or substrate, or one or more reservoirs within either a porous membrane or a membrane having a valve or port. Devices may further comprise a micropump, electro-osmotic pump or an osmotic delivery system to forcefully control the delivery of such substances and agents.

There are a number of systems known in the art to provide continuous or sustained delivery that may be adapted to the implants described herein. For example, drug delivery may be based upon: a gradual dissolution or biophysical degradation of a matrix that releases the drug over time, a biochemical degradation of a matrix that releases the drug over time, a diffusion controlled process, a more active system such as an osmotic pump or another type of pump, or a combination thereof. For the purposes of this disclosure "biodegradable" refers to a component which may degrade by a biophysical degradation (such as dissolution, dissociation, melting, etc.), biochemical degradation, or a combination thereof.

In biodegradable components, the drug may be physically or chemically trapped in the matrix. For example, the matrix may be a solid wherein the drug is non-covalently incorporated into the matrix. In some embodiments, the drug may be dissolved in a melt of the matrix, the matrix cooled, thus trapping the drug in the matrix. For example, the biodegradable polymer and the drug might be melt extruded. Alternatively, the drug and the matrix may be dissolved in a solvent, and the solvent may be removed. Other methods of non-covalently entrapping a drug in a matrix may also be used. Alternatively, the drug may be covalently bonded to the matrix via a cleavable linkage such as an ester bond.

In some embodiments where drug delivery is based upon biophysical or biochemical degradation of a matrix, the implant may contain one or more components which are biostable. In some embodiments, this may enable the implant to continue to perform other non-drug delivery functions after part of the implant has eroded from drug delivery. For example, a biostable component may be coated with one or more layers of biodegradable material containing a drug. In some embodiments, the biostable component may comprise pores or holes comprising particles of biodegradable material containing a drug. In some embodiments, the pores or holes may provide greater surface area to which a biodegradable material containing a drug may be affixed or coated, which may increase loading of the drug and be used to modulate the delivery time. In some embodiments, a component may be composed of biodegradable material and connected or coupled to one or more biostable components. In some embodiments, a biostable component may comprise a porous or channeled network, such as a molecular sieve (including a cross-linked polymer). The porous network may be coated or intercalated, impregnated, or included with the biodegradable material comprising a drug. Thus, as the biodegradable material degrades, the structural integrity of the component may remain intact in the form of the biostable network.

Examples of biodegradable materials may include, but are not limited to, particles having a diameter in the range of about 1 nm to about 100 µm, or about 100 nm to about 10 µm, such as microspheres, microcapsules, microspherules and other such micropackages, liposomes, nanoparticles, biodegradable controlled release polymer matrices, and the like.

Some microparticles or nanoparticles may be prepared by a self-assembly process, such as by the formation of micelles, microemulsions, or nanoemulsions in an aqueous medium. These compositions may be used for sustained delivery in that form, or may be modified. In some embodiments, lipids may be used to prepare these compositions. Lipids which may be used to create these compositions include but are not limited to: fatty acids such as lauric acid, palmitic acid, stearic acid, arachidic acid, behenic acid, lignoceric acid, palmitoleic acid, oleic acid, linoleic acid, arachidonic acid eicosopentaenoic acid nervonic acid, etc.; triacylglycerols; glycerophospholipids; sphingolipids such as sphingomyelins, cerebrosides, gangliosides, etc., cholesterol; etc. In some embodiments, the lipid may have about 6-100 carbon atoms, about 12-60 carbon atoms, or about 12-40 carbon atoms. A lipid may also be prepared as a film, coating, or larger solid component as a biodegradable component.

In other embodiments, a micelle, microemulsion, or nanoemulsion system may be polymerized to form a biodegradable polymer, thus providing microparticles or nanoparticles of a biodegradable particle. In some embodiments, a biodegradable polymer may be incorporated into a micelle, microemulsion, or nanoemulsion system and crosslinked to provide microparticles or nanoparticles of a biodegradable particle. Alternatively, a biodegradable polymer may be prepared as a film, coating, or other larger solid component. Examples of useful biodegradable polymers include, without limitation, such materials derived from and/or comprising organic esters and organic ethers, which when degraded result in physiologically acceptable degradation products, including the monomers. Some embodiments comprise biodegrable polymers derived from and/or including, anhydrides, amides, orthoesters and the like, by themselves or in combination with other monomers. In some embodiments, the biodegradable polymer may be an addition or condensation polymer. The biodegradable polymer may be cross-linked or non-crosslinked, for example not more than lightly cross-linked, such as less than about 5%, or less than about 1% of the polymeric material being cross-linked. The biodegradable polymer may also include oxygen and/or nitrogen. Oxygen may be present as oxy, e.g. hydroxy or ether, carbonyl, e.g. non-oxo-carbonyl, such as carboxylic acid ester, and the like. Nitrogen may be present as amide, cyano and amino. In some embodiments, the biodegradable polymer comprises at least one of a ester, an ether, and an amide. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present devices.

In some embodiments, the biodegradable polymer may be selected from: polylactides, polyglycolides, polycaprolactones, polyanhydrides, polyamides, polyurethanes, polyesteramides, polyorthoesters, poly(amino acids), pseudo poly (amino acids), polydioxanones, polyacetals, polyketals, polycarbonates, polyorthoesters, polyphosphazenes, polyhydroxybutyrates, polyhydroxyvalerates, polyalkylene oxalates, polyalkylene succinates, poly(malic acid), poly (amino acids), poly(methyl vinyl ether), poly(maleic anhydride), collagen, hyaluronic acid, chitin, chitosan, poly (iminocarbonates), polyoxaesters including polyoxaesters containing amido groups, polyamidoesters, and copolymers, terpolymers, derivatives thereof and mixtures thereof. Some embodiments may comprise poly lactic acid, poly glycolic acid, poly lactic acid/glycolic acid (PLGA), derivatives thereof, and mixtures thereof. Some embodiments, may comprise polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, hydroxybutyrate, hydroxyvalerate, para-dioxanone, trimethylene carbonate (and its alkyl derivatives), and combinations thereof. Generally, by employing the L-lactate or D-lactate, a slowly eroding polymer or polymeric material may be achieved. In some embodiments, erosion may be substantially enhanced with the lactate racemate. Some embodiments may comprise polysaccharides such as, without limitation, calcium alginate, and functionalized celluloses, particularly carboxymethylcellulose esters characterized by being water insoluble, a molecular weight of about 5 kD to 500 kD, for example. Some embodiments may comprise polyesters, polyethers and combinations thereof which are biocompatible and may be biodegradable and/or bioerodible.

Continuous or sustained delivery may also be based upon a diffusion controlled process. In some embodiments, a component of the device may comprise barriers to diffusion such as a selective membrane, or a solid component with pores which present bottleneck to a diffusion process. For example, pores having diameters in the range of about 0.1 nm to about 1000 nm, about 0.5 nm to about 50 nm, or about 1 nm to about 10 nm, may reduce the diffusion rates of drugs and/or water, thus providing more sustained delivery. In some materials, these barriers may comprise a molecular sieve material such as a crosslinked polymer. In some embodiments, these barriers may comprise a biostable crosslinked polymer.

Hydrogels may be part of a diffusion controlled or a biodegradable component of a drug delivery system. In some embodiments, hydrogels are polymers may that absorb and swell in an aqueous environment. Water-swellable hydrophilic polymers, both ionic and nonionic, often referred to as "osmopolymers" and "hydrogels." Exemplary materials include polymers such as vinyl polymers, acrylics, polysaccharides, polyalkylene oxides, polyvinylpyrrolidone, polyurethanes, sodium croscarmellose, carrageenan, HEC, HPC, HPMC, CMC and CEC, sodium alginate, polycarbophil, gelatin, xanthan gum, and sodium starch glycolate, and mixtures and copolymers thereof. Other materials include hydrogels comprising interpenetrating networks of polymers which may be formed by addition or by condensation polymerization, the components of which may comprise hydrophilic and hydrophobic monomers such as those just mentioned.

An active system may comprise a pump such as an osmotic pump. An osmotic pump provides sustained or controlled delivery of a drug by osmotic pressure. These devices are described in publications such as Theeuwes, J. Pharm. ScL, 64(12):1987-91 (1975). Other active systems are also known in the art.

Any drug or therapeutically active agent may be used with the devices disclosed herein. Suitable therapeutically active agents or drugs may include, but are not limited to: antineoplastic agents, such as platinum compounds (e.g., spiroplatin, cisplatin, and carboplatin), methotrexate, adriamycin, mitomycin, ansamitocin, bleomycin, cytosine arabinoside, arabinosyl adenine, mercaptopolylysine, vincristine, neurotoxins such as botulinum toxin, including botulinum toxin A, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon α-2a, interferon α-2b, teniposide (VM-26), vinblastine sulfate (VLB), vincristine sulfate, bleomycin, bleomycin sulfate, methotrexate, adriamycin, and arabinosyl; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, and B-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide and fludrocortisone acetate; vitamins such as cyanocobalamin neinoic acid, retinoids and derivatives such as retinol palmitate, and α-tocopherol; peptides, such as manganese super oxide dismutase; enzymes such as alkaline phosphatase; anti-allergic agents such as amelexanox; anticoagulation agents such as phenprocoumon and heparin; circulatory drugs such as propranolol; metabolic potentiators such as glutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT or Zidovudine), ribavirin and vidarabine monohydrate (adenine arabinoside, ara-A); anti-anginals such as diltiazem, nifedipine, verapamil, erythritol tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium mesylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium.

Figure 51A:
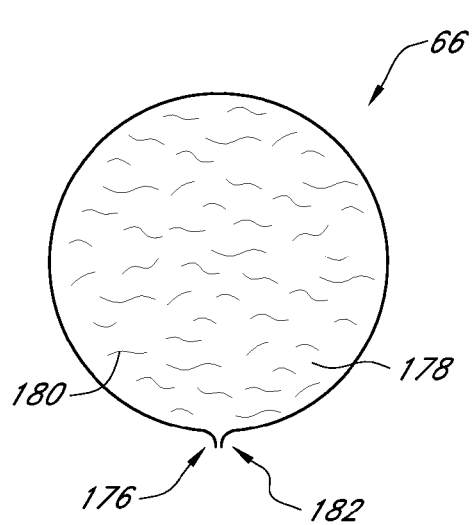
FIGS. 51A-C show different implants used as drug delivery devices.

In some embodiments, implants 66 provided herein may comprise an infusion device 176 comprised of a reservoir 178 containing a drug 180 and a flow-restricted exit port 182 in fluid communication with the drug in the reservoir. FIG. 51A shows a cross-section of a spherical implant 66 filled with at least partially with drug 180. The flow-restricted exit port may provide delivery of a drug over a period of at least 24 hours, 5 days, 15 days or more. The device may be configured to deliver the drug at an appropriate rate as desired by the physician. For example, the drug may be in a liquid form and the device may deliver the drug at a rate of less than about 400 μl/hour or about 400 mg/hour, or in a range of about 1-100 μl/hour or about 1-100 mg/hour.

Figure 51B:
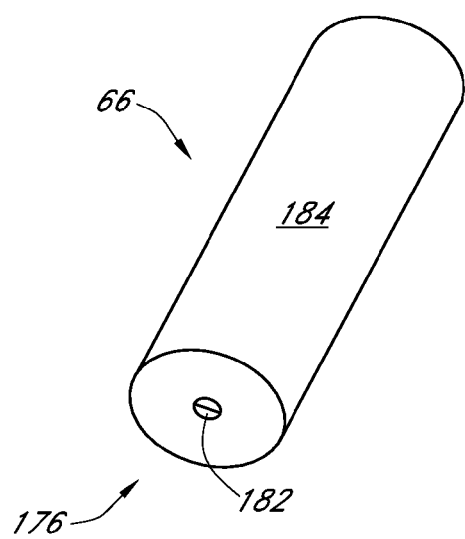

In another embodiment, an implantable infusion device 176 comprises an elongated elastomeric portion having a first end and a second end and is adapted to contain and pressurize a liquid 184, as is shown in FIG. 51B. The device may also comprise a flow controller providing an exit port 182 in fluid communication with the liquid 184 in the elastomeric portion. The flow controller may provide for controlled release of the liquid from the implant.

Drugs or other substances for use in the body and especially the bladder can be provided in a variety of forms, including liquids, solids, and hydratable powders. These drugs and other materials can be used for a variety of purposes, including the treatment of urinary incontinence, urinary tract cancer, urinary tract infections, inflammatory conditions of the urinary tract, interstitial cystitis, overactive bladder syndrome, and to provide pain relief. In addition, the substance released from the device may used for diagnostic purposes.

Urinary incontinence, including urge incontinence and neurogenic incontinence, can be treated using an implant as described herein. Preferably, anticholinergic and/or antispasmodic agents are used. In addition, antimuscarinic agents, β-2 agonists, norepinephrine uptake inhibitors, serotonin uptake inhibitors, calcium channel blockers, potassium channel openers, and muscle relaxants can also be used. Urinary tract cancer, such as bladder cancer and prostate cancer, may be treated using a device by infusing antiproliferative agents, cytotoxic agents and/or chemotherapeutics. Treatment of urinary tract cancer can be effected in conjunction with other conventional cancer treatment techniques, including surgical excision, and radiation therapy.

In a similar manner, infections involving the bladder, the prostate, and the urethra, can be treated using an implant as described herein. Antibiotics, antibacterial, antifungal, antiprotozoal, antiviral and other anti-infective agents can be administered for treatment of such infections.

Inflammatory conditions such as interstitial cystitis, prostatitis, and urethritis can also be treated using an implant as described herein. Drugs having an anti-inflammatory and/or coating effect are useful in this regard. Suitable drugs include dimethyl sulfoxide (DMSO), heparin, pentosanpolysulfate sodium, and flavoxate.

Implants as described herein can also be used to provide pain relief to the patient. In this regard, a variety of anesthetic and/or analgesic agents can be infused through the implant.

An implant as described herein can also be used to administer drugs and other materials for a variety of other purposes. For example, the device can be used to administer glycine for purposes such as bladder irrigation.

Various treatment methods can provide for slow, continuous, intermittent or periodic release of a desired quantity of drug over a desired period of time. In one preferred embodiment, the volume of the infuser is such that it can deliver the desired dose of drug over an extended period of time, e.g., 24 hours, 5 days, 10 days, 15 days or even 20, 25, 30, 60, 90 days or more. The rate of delivery in order to accomplish this result is relatively slow. Thus, drug delivery rates within the range of 0.0001, 0.001, 0.01, 0.1, 1, 5, 10, 25, 50, 75, 100, 150, or 200 µl/hr, or 0.0001, 0.001, 0.01, 0.1, 1, 5, 10, 25, 50, 75, 100, 150, or 200 mg/hr can be used. Of course, slower or faster delivery rates can be selected depending upon the drug being delivered and the disease being treated. In any particular situation, and for any particular disease state, the concentration of the drug and the rate of delivery can be selected by the physician based on conventional methodologies. The rate of delivery can also be in bolus form, utilizing a programmed controller.

Figure 51C:
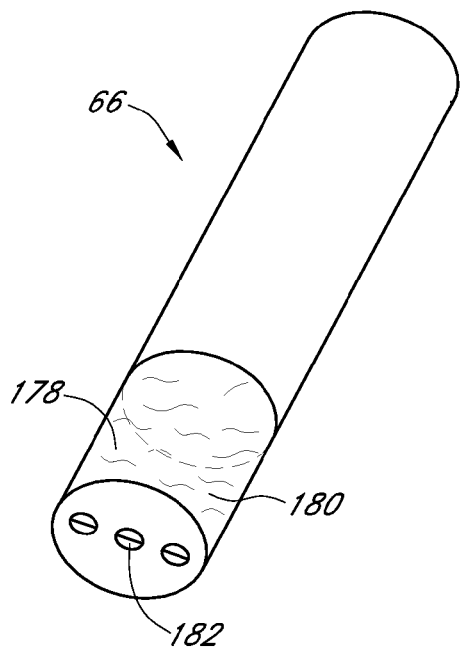

In one aspect shown in FIG. 51C, an implant has a body which comprises at least one hollow elastomeric tube having an outer surface, an inner surface, and at least one reservoir 178 defined within the hollow tube; a drug formulation (which includes a drug) 180 contained in the reservoir 178; and one or more apertures 182 providing a passageway to release the drug 180 from the drug delivery device. The apertures 182 may be through the sidewall of the tube or through an end of the tube. The diameter of each aperture preferably is between about 20 µm and about 300 µm. The hollow tube may be formed of a water permeable material. The device is configured to permit its insertion into a body cavity and its retention in the body cavity during release of the drug.

In some embodiments, an implant can comprise a drug or a therapeutic agent. The implant can operate to intravesically deliver the drug or therapeutic agent. The drug or therapeutic agent can be contained within an enclosure, similar to those described above, for example. Alternatively, the drug or therapeutic agent can be contained within one or more separate reservoirs. The reservoirs can have a flow restrictive element. A chamber holding a high vapor pressure media can be in pressure communication with said one or more reservoirs and can drive the delivery of the drug or therapeutic agent out of said flow restrictive element over time. In some embodiments, the high vapor pressure media in the chamber maintains a constant pressure within the one or more separate reservoirs operable to drive said drug or therapeutic agent out of said one or more separate reservoirs at a selected rate.

An implant can have a degradable membrane. The degradable membrane may be formed of biodegradable polymer material, and may have a thickness between about 145 µm and about 160 µm.

In one embodiment, the drug formulation is in a solid or semi-solid form. In one embodiment adapted for use in the bladder, the drug formulation and dose are effective for treating overactive bladder syndrome, bladder cancer, or interstitial cystitis. The drug formulation may include an anesthetic, an analgesic, an antibiotic, or a combination thereof. The drug formulation may further include one or more pharmaceutically acceptable excipients. In another aspect, a method is provided for administering a drug to a patient.

Implants can be tailored to release one or more drugs in a preprogrammed manner, for therapies requiring bolus (onetime), pulsatile, or constant drug delivery. An implant can be implanted once and release several doses of drug over an extended period, without requiring surgery or frequent interventions (such as to re-fill the drug reservoir of a conventional device).

In a preferred embodiment, an implant operates essentially as an osmotic pump. Following implantation, water permeates through the tube body, enters the reservoir, and is imbibed by the drug formulation. Solubilized drug is dispensed at a controlled rate out of the implant through one or more apertures, driven by osmotic pressure in the reservoir. PFC can also be used to pressurize the reservoir. The delivery rate can be predicted from the physicochemical parameters defining the particular drug delivery system, according to well known principles, which are described for example in Theeuwes, J. Pharm. ScL, 64(12):1987-91 (1975). In this embodiment, the water can enter the reservoir in one way, mix with the drug and then exit out another way which has a different aperture size from the entrance. In an alternative embodiment, the implant operates essentially by diffusion of the drug through one or more apertures.

In one embodiment of non-resorbable implant, the tube of the body is formed of a medical grade silicone tubing, as known in the art. Other examples of suitable non-resorbable materials include synthetic polymers selected from poly (ethers), poly(acrylates), poly(methacrylates), poly(vinyl pyrolidones), poly(vinyl acetates), poly(urethanes), celluloses, cellulose acetates, poly(siloxanes), poly(ethylene), poly (tetrafluoroethylene) and other fluorinated polymers, poly (siloxanes), copolymers thereof, and combinations thereof. In another embodiment, the device body is resorbable. In one embodiment of resorbable device, the tube of the body is formed of a biodegradable or bioerodible polymer. Examples of suitable resorbable materials include synthetic polymers selected from poly(amides), poly(esters), poly(anhydrides), poly(orthoesters), polyphosphazenes, pseudo poly(amino acids), copolymers thereof, and mixtures thereof. In a preferred embodiment, the resorbable synthetic polymers are selected from poly(lactic acids), poly(glycolic acids), poly (lactic-co-glycolic acids), poly(caprolactones), and mixtures thereof. The size of a urological device, or other implant device, is important. The smaller the device, the less pain and discomfort the patient will experience during insertion and use of the device, and particularly during cystoscopic implantation of the device. In a preferred embodiment, the device body has a length of about 1 cm to about 10 cm, and when in its shape for insertion it has an effective outer diameter (or largest cross-sectional dimension) of about 0.05 cm to 0.07 cm. (A 10 cm length device forms a ring with a diameter of 3.18 cm.) In one embodiment, the inner surface of the tube has a diameter between about 300 µm and about 500 µm, and the outer surface of the tube has an diameter between about 600 µm and about 900 µm.

The size of the apertures of an infusion device may be important in providing a controlled rate of release of the drug. Where the device operates as an osmotic pump, it should be small enough to minimize the contribution to the delivery rate made by diffusion of the drug through the aperture, yet the aperture should be large enough to minimize hydrostatic pressure within the reservoir, which pressure undesirably would tend to decrease the osmotic flux and/or cause the reservoir volume to increase. Within these constraints on aperture size, one may then vary the number of such sized apertures employed in a single device (or in a single reservoir) in order to provide a needed total rate of drug released. In exemplary embodiments, the diameter of the aperture is between about 20 µm and about 300 µm (e.g., 20 to 100 µm, 25 to 75 µm, etc.). Where the device operates primarily by a diffusion mechanism, apertures may be in this range or larger.

A single device may have apertures of two or more different sizes. The aperture typically is circular in shape, although other shapes are possible and envisioned, and will typically depend on manufacturing considerations.

The apertures can optionally have a degradable membrane disposed over or in each of the apertures, to control the time at which release of the drug formulation begins. In one embodiment, the degradable membrane is in the form of a uniform coating covering the outer surface of the tube of the device body. In another embodiment, the discrete degradable membranes are provided substantially within the aperture. Combinations of two or more degradable membranes may be used to control release from one aperture.

The thickness of the degradable membrane in a particular system will depend for example on the chemistry and mechanical properties of the material of construction selected for the degradable membrane (which primarily govern the rate of degradation), as well as on the desired time of delay of drug release for the particular drug delivery device. See, e.g., Richards Grayson, et al., "Molecular release from a polymeric microreservoir device: Influence of chemistry, polymer swelling, and loading on device performance" Wiley Inter-Science (6 Apr. 2004); Richards Grayson, et al., "Multi-pulse drug delivery form a resorbable polymeric microchip device" Nature Materials, Advance Online Publication (19 Oct. 2003); U.S. Pat. No. 6,808,522. In one embodiment, the degradable membrane has a thickness between about 100 µm and about 200 µm, such as between 145 µm and 160 µm.

Membranes can be formed of a biocompatible material. In one embodiment, the membranes are formed of a resorbable synthetic polymer such as polyester, a poly(anhydride), or a polycaprolactone. In another embodiment, the membranes are formed of a resorbable biological materials such as cholesterol, other lipids and fats.

For embodiments of these devices in which it is desired to release drug over a short period of time, the degradable membrane may be fabricated from quickly disintegrating materials including, for example, poly(lactide-co-glycolide) copolymers containing a high glycolide content, copolymers of poly(lactones) with fast degradation times, certain poly (anhydrides), hydrogels, oligosaccharides, and polysaccharides. For applications in which a longer or delayed release time is desirable, the degradable membrane may be fabricated from materials that take longer to disintegrate, for example, a resorbable biological materials such as cholesterol, other lipids and fats, and lipid bilayers, polymers such as poly(caprolactone) or certain poly(anhydrides), and PLGA copolymers with high lactic acid content.

In one embodiment, an intravesical drug delivery device is used to treat inflammatory conditions such as interstitial cystitis, prostatitis, and urethritis. Representative examples of specific drugs for these conditions include lidocaine hydrochloride, glycosaminoglycans (e.g., chondroitin sulfate, sulodexide), pentosanpolysulfate, dimethyl sulfoxide (DMSO), oxybutynin, mitomycin C, heparin, flavoxate, or a combination thereof.

In another embodiment, an intravesical drug delivery device is used to provide pain relief to the patient. A variety of anesthetic agent, analgesic agents, and combinations thereof may be used.

An intravesical drug delivery device can be used to treat urinary incontinence, including urge incontinence and neurogenic incontinence. Drugs that may be used include anticholinergic agents, antispasmodic agents, anti-muscarinic agents, β-2 agonists, norepinephrine uptake inhibitors, serotonin uptake inhibitors, calcium channel blockers, potassium channel openers, and muscle relaxants.

In another embodiment, an intravesical drug delivery device is used to treat urinary tract cancer, such as bladder cancer and prostate cancer. Drugs that may be used include antiproliferative agents, cytotoxic agents, chemotherapeutic agents, or a combination thereof. The drug treatment may be coupled with a conventional radiation or surgical therapy targeted to the cancerous tissue.

In still another embodiment, an intravesical drug delivery device is used to treat infections involving the bladder, the prostate, and the urethra. Antibiotics, antibacterial, antifungal, antiprotozoal, antiviral and other antiinfective agents can be administered for treatment of such infections.

Other drugs and excipient may be used for other therapies and at other nonbladder body cavity sites. Combinations of two or more drugs, stored in (and released from) the same or separate reservoirs in the device are envisioned. The excipient of the drug formulation may be a matrix material, selected to modulate or control the rate of release of the drug from the reservoir. In one embodiment, the matrix material may be a resorbable or non-resorbable polymer as described above. In another embodiment, the excipient comprises a hydrophobic or amphiphilic compound, such as a lipid, The drug formulation may provide a temporally modulated release profile or a more continuous or consistent release profile. Pulsatile release can be achieved from a plurality of reservoirs. For example, different degradable membrane can be used to by temporally stagger the release from each of several reservoirs.

Intravesical drug delivery devices and treatment methods described herein can provide extended, continuous, intermittent, or periodic release of a desired quantity of drug over a desired (predetermined) period of time. In one embodiment, the device can deliver the desired dose of drug over an extended period of time, e.g., 24 hours, 5 days, 7 days, 10 days, 14 days, or 20, 25, 30, 45, 60, or 90 days, or more. The rate of delivery and dosage of the drug can be selected depending upon the drug being delivered and the disease/condition being treated. The use of different degradation rates and/or excipient materials, along with varying the number and size of apertures in the device, can be used to tailor the device to have different release kinetics.

In one embodiment, a porous reticulated polymeric matrix is used to fabricate the implant to provide adequate fluid permeability. The average diameter or other largest transverse dimension of pores is from about 300 to about 10 pores per linear inch, preferably from about 300 to about 25 pores per linear inch, more preferably from about 150 to about 35 pores per linear inch, and most preferably between about 80 and 40 pores per linear inch.

Various reticulated hydrophobic polyurethane foams are suitable for this purpose. In one embodiment, structural materials for the porous elastomers are synthetic polymers, especially, but not exclusively, elastomeric polymers that are resistant to biological degradation, for example, polycarbonate polyurethanes, polyether polyurethanes, polysiloxanes, and the like. Such elastomers are generally hydrophobic but, may be treated to have surfaces that are less hydrophobic or somewhat hydrophilic. In another embodiment, such elastomers may be produced with surfaces that are less hydrophobic or somewhat hydrophilic.

A porous biodurable reticulatable elastomeric partially hydrophobic polymeric scaffold material can be provided for fabricating an implant or a material. More particularly, one embodiment provides a biodurable elastomeric polyurethane matrix which comprises a polycarbonate polyol component and an isocyanate component by polymerization, crosslinking and foaming, thereby forming pores, followed by reticulation of the foam to provide a biodurable reticulatable elastomeric product. The product is designated as a polycarbonate polyurethane, being a polymer comprising urethane groups formed from, e.g., the hydroxyl groups of the polycarbonate polyol component and the isocyanate groups of the isocyanate component.

Of particular interest are thermoplastic elastomers such as polyurethanes whose chemistry is associated with good biodurability properties, for example. In one embodiment, such thermoplastic polyurethane elastomers include polycarbonate polyurethanes, polyester polyurethanes, polyether polyurethanes, polysiloxane polyurethanes, polyurethanes with so-called "mixed" soft segments, and mixtures thereof. Mixed soft segment polyurethanes are known to those skilled in the art and include, e.g., polycarbonate-polyester polyurethanes, polycarbonate-polyether polyurethanes, polycarbonate-polysiloxane polyurethanes, polyester-polyether polyurethanes, polyester-polysiloxane polyurethanes and polyether-polysiloxane polyurethanes. In another embodiment, the thermoplastic polyurethane elastomer comprises at least one diisocyanate in the isocyanate component, at least one chain extender and at least one diol, and may be formed from any combination of the diisocyanates, difunctional chain extenders and diols described in detail above.

Some suitable thermoplastic polyurethanes for certain embodiments include, but are not limited to, polyurethanes with mixed soft segments comprising polysiloxane together with a polyether and/or a polycarbonate component, as disclosed by Meijs et al. in U.S. Pat. No. 6,313,254; and those polyurethanes disclosed by DiDomenico et al. in U.S. Pat. Nos. 6,149,678; 6,111,052; and 5,986,034, all of which are incorporated herein by reference.

Some suitable commercially-available thermoplastic elastomers include the line of polycarbonate polyurethanes supplied under the trademark BIONATES by The Polymer Technology Group Inc. (Berkeley, Calif.). For example, the very well-characterized grades of polycarbonate polyurethane polymer BIONATEV 80A, 55 and 90 are soluble in THF, processable, reportedly have good mechanical properties, lack cytotoxicity, lack mutagenicity, lack carcinogenicity and are non-hemolytic. Another suitable commercially-available elastomer is the CHRONOFLEX (g) C line of biodurable medical grade polycarbonate aromatic polyurethane thermoplastic elastomers available from CardioTech International, Inc. (Woburn, Mass.). Yet another suitable commercially-available elastomer is the PELLETHANE line of thermoplastic polyurethane elastomers, in particular the 2363 series products and more particularly those products designated 81A and 85A, supplied by The Dow Chemical Company (Midland, Mich.). These commercial polyurethane polymers are linear, not crosslinked, polymers, therefore, they are soluble, readily analyzable and readily characterizable.

To facilitate immobilization of the drug on the scaffold, the scaffold may be hydrophilized or coated with a hydrophilic coating to facilitate attachment of therapeutic agent or therapeutic agent drug bearing structures such as biologically erodible microspheres, microcapsules or other micropackages. Hydrophilization may comprise treatment of the hydrophobic material to render the surfaces partially hydrophilic or application of an adhesive or application of a hydrophilic coating, or deposit of a hydrophilic foam, for example, as described in Thomson, U.S. Pat. No. 6,617,014, incorporated herein by reference.

The hydrophilic foam coating can be made from polyurethanes containing appropriate and suitable isocyanate and polyols. Isocyanates suitable for use are aromatic, such as, for example, toluene dilsocyanate (TDI) or methylene diphenyl isocyanate (MDI), or with a aliphatic duisosyanate, such as hydrogenated MDI or isopherone dilsocyanate. One example of polyol is polyether polyols which are homopolymers of ethylene oxide, also known as polyethylene glycols, or copolymers of ethylene oxide and propylene oxides. Other examples of suitable polyols are polyester polyol, poly (ether-co-ester) polyol, poly (ether-co-hydrocarbon) polyol, poly (ether-co-siloxane) polyol, poly (ester-co-siloxane) polyol, poly (ether-co-carbonate) polyol, poly (ester-co-carbonate) polyol, poly (ester-co-hydrocarbon) polyol, or mixtures thereof.

Higher concentrations may be used, up to over 50% by weight of solids. Coatings may also be formed in a similar fashion by first dissolving the polyol, chain extender, crosslinker and catalyst in solvent and then adding the isocyanate, followed by casting and curing. High concentrations are also possible with this method.

Polyurethane coatings may also be prepared from water-based systems (dispersions). Polyurethanes used are ionomers (cationic or anionic) or, less often, from poly urethanes containing hydrophilic chains. Cationic ionomers are synthesized by the reaction of isocyanate-terminated prepolymers with tertiary amines containing hydroxyl groups, followed by quaternization of the tertiary nitrogen atom with, for example, methyl sulphate, alkyl chlorides, benzyl chloride, etc. This is then dispersed in water. Anionic ionomers are synthesized by the reaction of isocyanate-terminated prepolymers with salts of carboxylic or sulfonic acids which incorporate two reactive groups, amine or hydroxyl. The acid groups are first converted into salts to prevent their reaction with isocyanate. The resulting ionomer is also dispersible in water.

Alternatively, if anionic ionomers are prepared using carboxylic acids with amine groups, the reaction may be carried out in water (the amine groups will react with the isocyanate groups much faster than does water). Typical concentrations are in the range of 30-60% solids. In one embodiment, the hydrophilic film or coating for the internal surfaces of the hydrophobic elastomeric material that is used to fabricate the hydrophobic scaffold or an implant can be made from flowable polymeric material such as a polymer solution, emulsion, microemulsion, suspension, dispersion, a liquid polymer, or a polymer melt. For example, the flowable polymeric material can comprise a solution of the polymer in a volatile organic solvent. The coating or the film can have additional capacity to transport or bond to active ingredients that can then be preferentially delivered.

In one embodiment, the polymeric material can comprise a thermoplastic elastomer and the flowable polymeric material can comprise a solution of that thermoplastic elastomer that can also be biodurable. In another embodiment, the polymeric material can comprise a solvent-soluble biodurable thermoplastic elastomer and the flowable polymeric material can comprise a solution of that solvent-soluble biodurable thermoplastic elastomer. The solvent can then be removed or allowed to evaporate to solidify the polymeric material into a film or coating.

Suitable film-forming biodurable biocompatible non-biodegradable polymers to be used for hydrophilic coating include polyamides, polyolefins (e.g., polypropylene, polyethylene), nonabsorbable polyesters (e.g., polyethylene terephthalate), silicones, poly (meth)acrylates, polyesters, polyalkyl oxides (e.g., polyethylene oxide), polyvinyl alcohols, polyethylene glycols and polyvinyl pyrrolidone, as well as hydrogels, such as those formed from crosslinked polyvinyl pyrrolidinone and polyesters. Other polymers, of course, can also be used as the biocompatible polymer provided that they can be dissolved, cured or polymerized.

Suitable polymers and copolymers include polyolefins, polyisobutylene and ethylene-a-olefin copolymers; acrylic polymers (including methacrylates) and copolymers; vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile; polyvinyl ketones; polyvinyl aromatics such as polystyrene; polyvinyl esters such as polyvinyl acetate; copolymers of vinyl monomers with each other and with a-olefins, such as etheylene-methyl methacrylate copolymers and ethylene-vinyl acetate copolymers; acrylomitrile-styrene copolymers; ABS resins; polyamides, such as nylon 66 and polycaprolactam; alkyd resins; polycarbonates; polyoxymethylenes; polyimides; polyethers; epoxy resins; polyurethanes; rayon; rayon-triacetate; cellophane;cellulose and its derivatives such as cellulose acetate, cellulose acetate butyrate, cellulose nitrate, cellulose propionate and cellulose ethers (e.g., carboxymethyl cellulose and hydroxyalkyl celluloses); and mixtures thereof.

Suitable film-forming biodurable biocompatible biodegradable polymers to be used for hydrophilic coating include bioabsorbable aliphatic polyesters (e.g., homopolymers and copolymers of lactic acid, glycolic acid, lactide, glycolide, para-dioxanone, trimethylene carbonate, s-caprolactone and blends thereof). Further, biocompatible polymers include film-forming bioabsorbable polymers; these include aliphatic polyesters, poly (amino acids), copoly (ether-esters), polyalkylenes oxalates, polyamides, poly (iminocarbonates), polyorthoesters, polyoxaesters including polyoxaesters containing amido groups, polyamidoesters, polyanhydrides, polyphosphazenes, biomolecules and blends thereof. For the purpose of this disclosure aliphatic polyesters include polymers and copolymers of lactide (which includes lactic acid d-, 1-and meso lactide), s-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one and blends thereof.

In one embodiment, a biodurable matrix or the scaffold of the implant can provide a vehicle for the delivery of and/or the controlled release of a pharmaceutically-active agent, for example, a drug or a microspheres containing drug.

In another embodiment, the pharmaceutically-active agent is admixed with, covalently bonded to and/or adsorbed in or on the coating of reticulated elastomeric biodurable matrix to provide a pharmaceutical composition or by incorporating the pharmaceutically-active agent into additional hydrophilic coatings.

In another embodiment, the coating polymer or the coating foam and pharmaceutically-active agent or microspheres containing pharmaceutically-active agent have a common solvent. This can provide a coating that is a solution. In another embodiment, the pharmaceutically-active agent can be present as a solid dispersion in a solution of the coating polymer in a solvent. Alternatively, a pharmaceutically-active agent can be coated onto the foam, in one embodiment, using a pharmaceutically-acceptable carrier. If melt-coating is employed, then, in another embodiment, the pharmaceutically-active agent withstands melt processing temperatures without substantial diminution of its efficacy.

In another embodiment, a top coating can be applied to delay release of the pharmaceutically-active agent or microspheres containing pharmaceutically-active agent. In another embodiment, a top coating can be used as the matrix for the delivery of a second pharmaceutically-active agent. A layered coating, comprising respective layers of fast- and slow-hydrolyzing polymer, can be used to stage release of the pharmaceutically-active agent or to control release of different pharmaceutically-active agents placed in the different layers. Polymer blends may also be used to control the release rate of different pharmaceutically-active agents or to provide a desirable balance of coating characteristics (e.g., elasticity, toughness) and drug delivery characteristics (e.g., release profile). Polymers with differing solvent solubilities can be used to build-up different polymer layers that may be used to deliver different pharmaceutically-active agents or to control the release profile of a pharmaceutically-active agents.

A reticulated elastomeric biodurable matrix or the scaffold of the implant comprising a pharmaceutically-active agent may be formulated by mixing one or more pharmaceutically-active agent with the polymer used to make the scaffold, with the solvent or with the polymer-solvent mixture and foamed. In another embodiment, the components, polymers and/or blends used to form the foam comprise a pharmaceutically-active agent. To form these foams, the previously described components, polymers and/or blends are admixed with the pharmaceutically-active agent prior to forming the foam or the pharmaceutically-active agent is loaded into the foam after it is formed.

A preferred drug delivery implant material is a resiliently compressible composite polyurethane foam comprising a hydrophilic polymer foam coated on and throughout the pore surfaces of a nonabsorbable hydrophobic foam scaffold. One suitable such material is a composite polyurethane foam product as disclosed in Thomson, U.S. Pat. No. 6,617,014, incorporated herein by reference, which is both compressible and water absorbent or liquid absorbent. The hydrophobic foam provides tensile strength, support and resilient compressibility enabling the desired collapsing of the drug delivery implant for delivery and reconstitution in situ. The hydrophilic foam coated on the interior pore surfaces of the hydrophobic foam can support useful quantities of a drug for release in situ. A particular material of this nature is identified by the trademark CO-FOAM) (Hydrophilix, LLC, Portland, Me. (USA)) and is referenced herein as the "CO-FOAMJ composite" or the "CO-FOAMJ foam composite".

Useful, flexible, at least partially hydrophobic polyurethane foams and hydrophilic polymeric coatings would be known to those skilled in the art. Representative and preferred embodiments of such porous drug-bearing materials and composites suitable for use as implant materials are set forth in U.S. provisional patent application Ser. No. 60/471,518, filed May 15, 2003, and Ser. No. 60/471,520, filed May 15, 2003, both of which are incorporated herein by reference in their entirety.

Preferred composite foams have a composition that allows relatively free flow of urine through the foam implant. Additionally the resiliency of the foam composite helps retain the drug delivery implant in place as bladder naturally contracts and expands.

Desired drugs may be incorporated into an implant in any suitable manner. In a preferred embodiment an implant such as a cylinder, sphere, bullet, football, irregular shape, or another suitable shape comprises a porous or apertured structural scaffold coated with therapeutic agent-bearing material that releases one or more therapeutic agents.

The therapeutic agent or agents, or therapeutic agent-bearing structures, may be adhered, incorporated in a hydrophilic foam or other coating on the hydrophobic scaffold, or, possibly covalently bonded to the hydrophobic scaffold or the coating.

More specifically, embodiments enable the delivery of therapeutic and other biologically useful molecules from micro drug delivery systems such as microspheres, microcapsules, microspherules and other such micropackages, liposomes, nanoparticles, biodegradable controlled release polymer matrices, and other such drug or biologic agent micropackaging systems, as are known, or may become known, to those skilled in the art which are collectively referenced herein as "microspheres." Preferred microspheres can be charged with a biologically useful agent and will biodegrade or bioerode to release the agent in a controlled manner.

The agents to be delivered may include one or more small molecules, macromolecules, liposomal encapsulations of molecules, micro-drug delivery system encapsulation of therapeutic molecules, covalent linking of carbohydrates and other molecules to therapeutic molecules, and gene therapy preparations. The microspheres or microcapsules may contain therapeutic agents, enzymes, or other compounds for the purpose of delayed, sustained, or otherwise controlled release.

There are several general types of controlled release systems that can be employed. For example, therapeutic agent release can be diffusion controlled, meaning that the diffusion of the agent trapped within a polymer matrix is the rate-determining factor for the overall release rate. Erosion based systems also exist in which a polymer degrades over time and releases a therapeutic agent in an amount proportional to the gradual erosion. An osmotic pumping device uses osmotic pressure as the driving force for release. A fourth system is based on the swelling of a polymeric matrix, such as a hydrogel. Hydrogels are polymers that absorb and swell in an aqueous environment. The release of the agent is dependent on the volume increase of the gel upon swelling and is then diffusion controlled.

In a preferred embodiment, microspheres are embedded within a layer of hydrophilic polyurethane matrix or a layer or other hydrophilic degradable and non-degradable polymer matrix or layer applied to the surface of a reticulated polyurethane scaffold or other stable support. It is contemplated that the embedding of microspheres may be within any hydrophilic polyurethane or other hydrophilic degradable and non-degradable polymer, whether it is alone or applied to any stable surface.

In one embodiment of preparing the microsphere-bearing composite foam material, microspheres can be mixed with the free polymer components of the hydrophilic polyurethane, in the prepolymer phase. In another embodiment, of preparing the microsphere-bearing composite foam material, microspheres can be mixed with the film or coating forming hydrophilic polymer during the solution preparing process. In another embodiment, polyurethane, solvent, and a therapeutic agent are added as a coating, and then the solvent is evaporated, leaving behind a coating with embedded microspheres. The resultant mixture can then be used to coat hydrophobic scaffold, fixedly embedding microspheres within a hydrophilic layer, as it cures. By mixing microspheres within the hydrophilic layer, a dispersion of microspheres throughout the hydrophilic layer coated on the surfaces of pores of the hydrophobic support can be obtained.

Beneficially, microspheres are substantially held in place within hydrophilic polyurethane surface layer through covalent or other chemical bonding, or mechanical restraint. Substantial amounts of therapeutic agent may be incorporated within hydrophilic layer as compared to merely covalently binding agent directly to carrier.

Furthermore, the inclusion of microspheres in polyurethane coating exposes microspheres to whatever solution carrier was immersed within or exposed to. With both an aqueous solution and a lipid solution, microspheres are exposed to hydrated hydrophilic polyurethane layer of carrier and eluted into a liquid environment thereby allowing microspheres to be degraded and release agent in a controlled fashion from the hydrophilic polyurethane. This is in direct contrast to covalently binding or adsorbing these drugs to the hydrophilic layer, which may result in unexpected or uncontrollable release of therapeutic agent. The reticulated array of struts of carrier allows quick and easy fluidic transmission of therapeutic agent. Such therapeutic agents may include, but are not limited to, pharmaceuticals, therapeutic substances, vaccines, prophylactics and other substances depending on the intended use or result.

Immobilization of microspheres in the hydrophilic layer of carrier is thus achieved without adhesive. The hydrophilic layer acts as a binder and when the layer becomes fully hydrated, it remains attached to the underlying scaffold, it does not impede the release of drugs or compounds from microspheres as they degrade, or utilize another mechanism to release an agent over time, based on their own internal characteristics.

The composition of the hydrophilic layer is selected for its permeability to the particular agent being dispersed. Such materials are well-known.

Such materials are generally of a molecular structure which includes interstices, i.e., pores or voids, large enough to quickly allow absorption and relatively free movement of water molecules through the hydrophilic materials. In addition, the material, of which hydrophilic coating is made, should have interstices large enough to allow transmission of agent being dispersed, typically as a solution in an aqueous medium that has permeated contents of the bladder in the coating, for example, the case of a medication dispersing from device 10 situated in the human bladder.

Delivering agent locally generally results in a very small amount of agent being required to treat a specific location within the tissue, which has substantial benefits, such as less side effects. Smaller doses of agent will minimize the need to replace the device as often and will reduce the systemic effects that result from large drug doses as well as the effects that the agents will have on normally functioning tissue.

Examples of anticholinergic agents are propantheline bromide, imipramine, mepenzolate bromide, isopropamide iodide, clidinium bromide, anisotropine methyl bromide, scopolamine hydrochloride, and their derivatives. Examples of antimuscarinic agents include, but are not limited to, hyoscyamine sulfate, atropine, methantheline bromide, emepronium bromide, anisotropine methyl bromide, and their derivatives. Examples of polysynaptic inhibitors include baclofen and its derivatives.

Examples of beta-adrenergic stimulators include terbutaline and its derivatives.

Examples of calcium antagonists include terodiline and its derivatives. Examples of musculotropic relaxants include, but are not limited to, dicyclomine hydrochloride, flavoxate hydrochloride, papaverine hydrochloride, oxybutynin chloride, and their derivatives. Examples of an antineoplastic agents include, but are not limited to, carmustine levamisole hydrochloride, flutamide, (w-methyl-N-[4-nitro-3-(trifluoromethyl) phenyl]), adriamycin, doxorubicin hydrochloride, idamycin, fluorouracil, cytoxan, mutamycin, mustargen and leucovorin calcium. Examples of antispasmodic agents are hexadiphane, magnesium gluconate, oktaverine, alibendon, butamiverine, hexahydroadiphane, 2-piperidinoethyl 3-methylflavone-8-carboxylate, 4-methylumbelliferone 0,0-diethyl phosphorothiate. Examples of potassium channel openers include pinacidil and N-[(2-Nitrooxy) ethyl]-3-pyridinecarboxamide.

Additionally, a potential significant use of the therapeutic agent delivery implant is as a delivery system for chemotherapeutic agents to treat bladder cancer.

By delivering the therapeutic agent continuously to the tumor, more of the tumor cells can be exposed to the therapeutic agent during their proliferative phase when they are most sensitive to the chemotherapy. Additionally, the dose of the therapeutic agents can be kept lower then in the usual interrupted, short-term treatment, thus minimizing irritation and discomfort to the patient. Further, the fact that one minor procedure is needed for insertion and one for removal provides less inconvenience to the patient and better cost efficiency then with the usual interrupted, short-term treatment.

Therapeutic agents that do not readily cross to the plasma barrier offered by the wall of the urothelium may be employed for local usage, for example, to treat bladder-related conditions, while therapeutic agents that readily cross to the plasma barrier may be systemically administered via bladder implantation of the implants.

Some therapeutic agents may have dual functionality, being locally useful and also being systemically absorbable.

A therapeutic agent delivery implant can be useful in the delivery of antibiotics to the urinary tract, and especially bladder. Methods of treating such cases can comprise implantation of a therapeutic agent delivery implant containing an antibiotic into the bladder as a prophylactic measure to preempt possible urinary tract infection.

Other therapeutic agents that may be delivered to the bladder include antispasmodics to treat overactive or spastic bladders with desensitizing or antispasmodic agents. Overactive bladder and spastic bladder conditions area significant problem, and the possibility of placing an implant such as domical implant in the bladder that does not impinge on the bladder neck (the dome-shaped implant) while allowing the chronic delivery of a desensitizing agent for comfort or an antispasmodic agent is another benefit. Additionally, systemically acting therapeutic agents may be delivered by an implant. There are many therapeutic agents that require injection on a regular basis, for example, growth hormone. Proteins of which growth hormones are exemplary are fragile and cannot be taken orally due to destruction in the stomach due to the action of stomach acid and of proteolytic enzymes. Accordingly, they are delivered by daily injection. Such daily injections can be entirely avoided or reduced by delivering such labile therapeutic agents through the bladder mucus membrane employing the implants described herein.

Other suitable material for the implant and other biologically active agents for delivery by or impregnation of implants are listed in U.S. provisional application No. 61/200,147 filed Nov. 25, 2008, which is incorporated herein by reference.

Having thus described certain embodiments of the present invention, various alterations, modifications and improvements will be apparent to those of ordinary skill in the art. Such alterations, variations and improvements are intended to be within the spirit and scope of the present invention. Accordingly, the foregoing description is by way of example and is not intended to be limiting. In addition, any dimensions that appear in the foregoing description and/or the figures are intended to be exemplary and should not be construed to be limiting on the scope of the present invention described herein.

What is claimed is:

1. An implant delivery system configured to deliver an inflatable implant into a bladder via a urethra, the delivery system comprising:
    an elongate tubular body sized to pass through a urethra into a bladder, the tubular body comprising:
        a central lumen configured to hold an inflatable implant in an initial un-inflated state for delivery of the implant into the bladder;
        an atraumatic tip at a distal most end; and
        a lateral opening in a sidewall of the elongate tubular body, the lateral opening positioned proximally from the atraumatic tip and operable to deliver the inflatable implant laterally from the central lumen and into the bladder away from a wall of the bladder;
    an inflation tube positioned within the central lumen of the tubular body, the inflation tube configured to couple with the inflatable implant to allow inflation of the inflatable implant from within the tubular body; and
    an implant decoupler positioned within the central lumen of the tubular body around the inflation tube, the implant decoupler configured to decouple the inflatable implant from the inflation tube after inflation of the inflatable implant from the un-inflated state to an inflated state.

2. The implant delivery system of claim 1, further comprising a syringe in fluid communication with the inflation tube.

3. The implant delivery system of claim 2, further comprising a quantity of gas within the syringe.

4. The implant delivery system of claim 3, further comprising a quantity of liquid within the syringe.

5. The implant delivery system of claim 4, wherein the liquid is at least one of a high vapor pressure medium and a therapeutic agent.

6. The implant delivery system of claim 4, wherein the liquid is a high vapor pressure medium that is a mixture of one or more PFCs.

7. The implant delivery system of claim 1, further comprising the inflatable implant.

8. The implant delivery system of claim 7, wherein when in the initial un-inflated state within the central lumen, the inflatable implant is compressed, folded and coupled to the inflation tube.

9. The implant delivery system of claim 1, further comprising at least one of a flap, door or retractable cover configured to be positioned over the lateral opening.

10. The implant delivery system of claim 1, further comprising a depth stop configured to provide visual and/or tactile feedback of when the lateral opening in the elongate tubular body is within the bladder.

11. The implant delivery system of claim 1, further comprising a slit in the atraumatic tip.

12. The implant delivery system of claim 1, wherein the inflation tube has an end configured to couple with the inflatable implant to allow inflation of the inflatable implant while the end is positioned within the central lumen.

13. The implant delivery system of claim 12, wherein the implant decoupler is configured to decouple the inflatable implant from the end of the inflation tube within the central lumen after inflation of the inflatable implant from the un-inflated state to an inflated state.

14. A method of delivering an inflatable implant into a bladder via a urethra comprising:
- inserting an elongate tubular body of a delivery device within a urethra, the elongate tubular body comprising a central lumen holding an inflatable implant in an initial un-inflated state for delivery of the implant into a bladder;
- passing a distal tip of the elongate tubular body into the bladder;
- inflating the implant while it is positioned in the central lumen, inflating the implant causes the implant to expand outward from the central lumen and into the bladder;
- disengaging the inflatable implant within the bladder from said delivery device; and
- removing the delivery device from the bladder.

15. The method of claim 14, wherein inflating the implant while it is positioned in the central lumen further comprises expanding the implant laterally from the central lumen out of a lateral opening of the elongate tubular body.

16. The method of claim 15, wherein expanding further comprises expanding the implant out of the lateral opening in a direction substantially opposite to that of a trigone of the bladder.

17. The method of claim 15, wherein expanding further comprises expanding the implant out of the lateral opening so that the entire implant moves in a direction towards a dome of the bladder.

18. The method of claim 15, wherein expanding further comprises opening a flap covering the lateral opening.

19. The method of claim 15, further comprising removing a covering over the lateral opening.

20. The method of claim 14, wherein inflating the implant further comprises injecting at least one of a liquid and a gas into the implant.

21. The method of claim 20, wherein the liquid injected into the implant comprises at least one of a high vapor pressure medium and a therapeutic agent.

22. The method of claim 20, wherein inflating the implant further comprises injecting gas into the implant after injecting liquid.

23. The method of claim 14, wherein passing the distal tip further comprises passing the distal tip of the elongate tubular body into the bladder until there is at least one of visual and tactile feedback that the distal tip is within the bladder.

24. A method of delivering an inflatable implant into a bladder via a urethra comprising:
- inserting an elongate tubular body of a delivery device within a urethra, the elongate tubular body comprising a central lumen holding an inflatable implant in an initial un-inflated state for delivery of the implant into a bladder;
- passing a distal tip of the elongate tubular body into the bladder;
- inflating the implant and thereby advancing the implant from within the central lumen to outside of the central lumen and into the bladder, wherein inflating the implant comprises injecting a gas into the implant after injecting a liquid;
- disengaging the inflatable implant within the bladder from said delivery device; and
- removing the delivery device from the bladder.

25. The method of claim 24, wherein inflating the implant comprises injecting the gas and the liquid into the implant from a single syringe.

26. An implant delivery system configured to deliver an inflatable implant into a bladder via a urethra, the delivery system comprising:
- an elongate tubular body sized to pass through a urethra into a bladder, the tubular body extending along a longitudinal axis and comprising:
  - a central lumen configured to hold an inflatable implant in an initial un-inflated state for delivery of the implant into the bladder; and
  - a lateral opening operable to deliver the inflatable implant out of a side of the central lumen substantially perpendicular to the longitudinal axis and into the bladder away from a wall of the bladder;
- an inflation tube positioned within the central lumen of the tubular body, the inflation tube configured to couple with the inflatable implant to allow inflation of the inflatable implant from within the tubular body; and
- an implant decoupler positioned within the central lumen of the tubular body around the inflation tube, the implant decoupler configured to decouple the inflatable implant from the inflation tube after inflation of the inflatable implant from the un-inflated state to an inflated state.

27. The implant delivery system of claim 26, wherein the inflation tube has an end configured to couple with the inflatable implant to allow inflation of the inflatable implant while the end is positioned within the central lumen.

* * * * *